US011751942B2

(12) United States Patent
Greeley et al.

(10) Patent No.: US 11,751,942 B2
(45) Date of Patent: Sep. 12, 2023

(54) SURGICAL DEVICE

(71) Applicant: Medtronic Advanced Energy LLC, Minneapolis, MN (US)

(72) Inventors: Roger D. Greeley, Portsmouth, NH (US); Brian M. Conley, South Berwick, ME (US); David J. Flanagan, Somersworth, NH (US); Aaron J. Gifford, Lake Elsinore, CA (US); Steven G. Miller, West Newbury, MA (US); Blaine T. Murakami, Corona del mar, CA (US); Thomas P. Robinson, Addison, TX (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1318 days.

(21) Appl. No.: 14/689,794

(22) Filed: Apr. 17, 2015

(65) Prior Publication Data
US 2015/0238256 A1 Aug. 27, 2015

Related U.S. Application Data

(63) Continuation of application No. 12/877,400, filed on Sep. 8, 2010, now Pat. No. 9,345,541.
(Continued)

(51) Int. Cl.
*A61B 18/18* (2006.01)
*A61B 18/14* (2006.01)
*A61B 18/00* (2006.01)

(52) U.S. Cl.
CPC .............. *A61B 18/18* (2013.01); *A61B 18/14* (2013.01); *A61B 2018/0063* (2013.01);
(Continued)

(58) Field of Classification Search
CPC ... A61B 18/18; A61B 18/14; A61B 2218/002; A61B 2018/0063; A61B 2018/00178; A61B 2018/00589; A61M 2205/12
See application file for complete search history.

(56) References Cited

U.S. PATENT DOCUMENTS 2,888,928 A 6/1959 Seiger
3,223,088 A 12/1965 Barber et al.
(Continued)

FOREIGN PATENT DOCUMENTS

EP 0 544 274 11/1992
EP 0 544 247 8/1993
(Continued)

OTHER PUBLICATIONS

Reexam Cert 4794 for U.S. Pat. No. 5,697,536, Jun. 10, 2003, Eggers, et al.
(Continued)

*Primary Examiner* — Michael F Peffley
*Assistant Examiner* — Yasamin Ekrami
(74) *Attorney, Agent, or Firm* — Patterson Thuente IP

(57) ABSTRACT

The invention provides a cartridge assembly to couple a tissue treatment device with an electrosurgical unit, with the cartridge assembly operable with a power delivery apparatus and a fluid delivery apparatus of the electrosurgical unit. The invention also provides an electrosurgical unit comprising a power delivery apparatus and a fluid delivery apparatus operable with the cartridge assembly and a system thereof.

44 Claims, 41 Drawing Sheets

Related U.S. Application Data

(60) Provisional application No. 61/240,562, filed on Sep. 8, 2009.

(52) U.S. Cl.
CPC .............. *A61B 2018/00178* (2013.01); *A61B 2018/00589* (2013.01); *A61B 2018/00601* (2013.01); *A61B 2218/002* (2013.01)

(56) References Cited

U.S. PATENT DOCUMENTS

| | | |
|---|---|---|
| 3,682,130 A | 8/1972 | Jeffers |
| 3,750,650 A | 8/1973 | Ruttgers |
| 3,955,284 A | 5/1976 | Balson |
| 4,014,342 A | 3/1977 | Staub et al. |
| 4,060,088 A | 11/1977 | Morrison, Jr. et al. |
| 4,195,637 A | 4/1980 | Gruntzig et al. |
| 4,207,897 A | 6/1980 | Loyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |
| 4,278,090 A | 7/1981 | Van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Sorochenko |
| 4,708,126 A | 11/1987 | Toda et al. |
| 4,736,749 A | 4/1988 | Lundback |
| 4,779,611 A | 10/1988 | Grooters et al. |
| 4,802,475 A | 2/1989 | Weshahy |
| 4,878,493 A | 11/1989 | Pasternak et al. |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,112,299 A | 5/1992 | Pascaloff |
| 5,167,659 A | 12/1992 | Dhtomo et al. |
| 5,190,541 A | 3/1993 | Abele et al. |
| 5,195,959 A | 3/1993 | Smith |
| 5,230,704 A | 7/1993 | Moberg et al. |
| 5,234,428 A | 8/1993 | Kaufman |
| 5,246,422 A | 9/1993 | Favre |
| 5,254,117 A | 10/1993 | Rigby et al. |
| 5,275,609 A | 1/1994 | Pingleton et al. |
| 5,281,215 A | 1/1994 | Midler |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowler |
| 5,330,521 A | 7/1994 | Cohen |
| 5,334,181 A | 8/1994 | Rubinsky et al. |
| 5,334,193 A | 8/1994 | Nardella |
| 5,336,220 A * | 8/1994 | Ryan .................. A61B 17/3203 138/108 |
| 5,348,554 A | 9/1994 | Imran et al. |
| 5,349,482 A | 9/1994 | Park |
| 5,352,222 A | 10/1994 | Rydell et al. |
| 5,353,783 A | 10/1994 | Nakao et al. |
| 5,354,258 A | 10/1994 | Dory |
| 5,361,752 A | 11/1994 | Moll et al. |
| 5,376,078 A | 12/1994 | Dinger et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,348 A | 4/1995 | Anspach et al. |
| 5,405,376 A | 4/1995 | Mulier et al. |
| 5,409,483 A | 4/1995 | Campbell et al. |
| 5,413,556 A | 5/1995 | Whittingham |
| 5,417,709 A | 5/1995 | Slater |
| 5,423,807 A | 6/1995 | Mlilder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stem et al. |
| 5,443,470 A | 8/1995 | Stem et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,492,527 A | 2/1996 | Glowa et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,500 A | 4/1996 | Webb et al. |
| 5,505,700 A | 4/1996 | Leone et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,540,708 A | 7/1996 | Lim et al. |
| 5,542,196 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,560,373 A | 10/1996 | DeSantis |
| 5,562,702 A | 10/1996 | Huitema et al. |
| 5,562,720 A | 10/1996 | Stem et al. |
| 5,569,241 A | 10/1996 | Edwards |
| 5,569,243 A | 10/1996 | Kortenbach et al. |
| 5,569,254 A | 10/1996 | Carlson et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |

(56) References Cited

U.S. PATENT DOCUMENTS

| | | |
|---|---|---|
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,462 A | 3/1997 | Imran |
| 5,609,573 A | 3/1997 | Sandock |
| 5,617,854 A | 4/1997 | Munsif |
| 5,620,415 A | 4/1997 | Lucey et al. |
| 5,620,447 A | 4/1997 | Smith et al. |
| 5,630,837 A | 5/1997 | Crowley |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,637,090 A | 9/1997 | McGee et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,702,390 A | 12/1997 | Austin et al. |
| 5,712,543 A | 1/1998 | Sjostrom |
| 5,713,942 A | 2/1998 | Stem |
| 5,716,389 A | 2/1998 | Walinsky et al. |
| 5,718,241 A | 2/1998 | Ben-Haim et al. |
| 5,718,701 A | 2/1998 | Shai et al. |
| 5,720,775 A | 2/1998 | Lanard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,743,903 A | 4/1998 | Stern et al. |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,792,167 A | 8/1998 | Kablik et al. |
| 5,797,905 A | 8/1998 | Fleischman et al. |
| 5,797,960 A | 8/1998 | Stevens et al. |
| 5,735,290 A | 9/1998 | Nelson et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,810,809 A | 9/1998 | Rydell |
| 5,814,044 A | 9/1998 | Hooven |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,023 A | 12/1998 | Mericle |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,873,886 A | 2/1999 | Larsen et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier |
| 5,897,554 A | 4/1999 | Chia et al. |
| 5,899,898 A | 5/1999 | Arless et al. |
| 5,899,899 A | 5/1999 | Arless et al. |
| 5,899,915 A | 5/1999 | Saadat |
| 5,902,289 A | 5/1999 | Swartz et al. |
| 5,904,681 A | 5/1999 | West, Jr. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,928,191 A | 9/1999 | Houser et al. |
| 5,954,661 A | 9/1999 | Greenspon et al. |
| 5,971,980 A | 10/1999 | Sherman |
| 5,971,983 A | 10/1999 | Lesh |
| 5,975,919 A | 11/1999 | Arnett et al. |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,042,593 A | 3/2000 | Storz et al. |
| 6,048,333 A | 4/2000 | Lennox et al. |
| 6,053,923 A | 4/2000 | Veca et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,063,081 A | 5/2000 | Mulier |
| 6,065,744 A | 5/2000 | Edwards |
| 6,066,139 A | 5/2000 | Ryan et al. |
| 6,068,653 A | 5/2000 | LaFontaine |
| 6,071,279 A | 6/2000 | Whayne et al. |
| 6,074,386 A | 6/2000 | Goble et al. |

(56) References Cited

U.S. PATENT DOCUMENTS

| | | | |
|---|---|---|---|
| 6,083,237 A | 7/2000 | Huitema et al. |
| 6,086,585 A | 7/2000 | Hovda et al. |
| 6,088,894 A | 7/2000 | Oakley |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,528 B1 | 4/2001 | Koblish et al. |
| 6,217,576 B1 | 4/2001 | Tu et al. |
| 6,217,598 B1 | 4/2001 | Berman et al. |
| 6,221,088 B1 | 4/2001 | Bays |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 | 9/2001 | Laufer et al. |
| 6,293,943 B1 | 9/2001 | Panescu et al. |
| 6,296,619 B1 | 10/2001 | Brisken et al. |
| 6,296,638 B1 | 10/2001 | Davison et al. |
| 6,299,633 B1 | 10/2001 | Laufer |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carver et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,956 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,494,892 B1 | 12/2002 | Ireland et al. |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,575,969 B1 * | 6/2003 | Rittman, III ....... A61B 18/1482 128/898 |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David et al. |
| 6,736,810 B2 | 5/2004 | Hoey |
| 6,752,816 B2 | 6/2004 | Culp et al. |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier et al. |
| 6,915,806 B2 | 7/2005 | Pacek et al. |
| 6,916,318 B2 | 7/2005 | Francischelli |
| 6,918,404 B2 | 7/2005 | Dias da Silva |

(56) References Cited

U.S. PATENT DOCUMENTS

| | | | |
|---|---|---|---|
| 6,936,046 B2 | 8/2005 | Hissong | |
| 6,942,661 B2 | 9/2005 | Swanson | |
| 6,949,097 B2 | 9/2005 | Stewart et al. | |
| 6,949,098 B2 | 9/2005 | Mulier | |
| 6,953,461 B2 | 10/2005 | Bloom et al. | |
| 6,960,205 B2 | 11/2005 | Jahns | |
| 6,962,589 B2 | 11/2005 | Mulier | |
| 6,979,332 B2 | 12/2005 | Adams | |
| 7,018,241 B2 | 3/2006 | Caveney et al. | |
| 7,048,687 B1 | 5/2006 | Reuss et al. | |
| 7,066,586 B2 | 6/2006 | da Silva | |
| 7,156,845 B2 | 1/2007 | Mulier et al. | |
| 7,166,106 B2 | 1/2007 | Bartel et al. | |
| 7,179,255 B2 | 2/2007 | Lettice et al. | |
| 7,207,471 B2 | 4/2007 | Heinrich et al. | |
| 7,232,440 B2 | 6/2007 | Dumbauld et al. | |
| 7,237,990 B2 | 7/2007 | Deng | |
| 7,247,155 B2 | 7/2007 | Hoey et al. | |
| 7,247,161 B2 | 7/2007 | Johnston et al. | |
| 7,261,711 B2 | 8/2007 | Mulier et al. | |
| 7,276,074 B2 | 10/2007 | Adams et al. | |
| 7,309,325 B2 | 12/2007 | Mulier et al. | |
| 7,311,708 B2 | 12/2007 | McClurken | |
| 7,322,974 B2 | 1/2008 | Swoyer et al. | |
| 7,361,175 B2 | 4/2008 | Suslov | |
| 7,364,579 B2 | 4/2008 | Mulier et al. | |
| 7,416,539 B2 | 8/2008 | Johnston et al. | |
| 7,442,191 B2 | 10/2008 | Hovda et al. | |
| 7,445,436 B2 | 11/2008 | Mittelstein et al. | |
| 7,537,595 B2 | 5/2009 | McClurken | |
| 7,604,635 B2 | 10/2009 | Bloom et al. | |
| 7,608,072 B2 | 10/2009 | Swanson | |
| 7,645,277 B2 | 1/2010 | Bloom et al. | |
| 7,651,494 B2 | 1/2010 | Bloom et al. | |
| 7,674,263 B2 | 3/2010 | Ryan | |
| 7,691,050 B2 | 4/2010 | Gellman | |
| 7,736,361 B2 | 6/2010 | Palanker | |
| 7,776,014 B2 | 8/2010 | Visconti et al. | |
| 7,811,282 B2 * | 10/2010 | McClurken | A61B 18/12 606/49 |
| 7,815,634 B2 | 10/2010 | Bloom et al. | |
| 7,909,820 B2 | 3/2011 | Lipson | |
| 7,918,852 B2 | 4/2011 | Tullis et al. | |
| 7,942,872 B2 | 5/2011 | Ein-Gal | |
| 7,976,544 B2 | 7/2011 | McClurken | |
| 7,993,337 B2 | 8/2011 | Lesh | |
| 7,997,278 B2 | 8/2011 | Utley et al. | |
| 7,998,140 B2 | 8/2011 | McClurken | |
| 8,034,071 B2 | 10/2011 | Scribner et al. | |
| 8,038,670 B2 | 10/2011 | McClurken | |
| 8,048,070 B2 | 11/2011 | O'Brien | |
| 8,083,736 B2 | 12/2011 | Bloom et al. | |
| 8,105,323 B2 | 1/2012 | Buysse et al. | |
| 8,109,956 B2 | 2/2012 | Shadek | |
| 8,172,828 B2 | 4/2012 | Chang et al. | |
| 8,177,783 B2 | 5/2012 | Davison et al. | |
| 8,202,288 B2 | 6/2012 | Adams et al. | |
| 8,216,233 B2 | 7/2012 | McClurken | |
| 8,323,276 B2 | 12/2012 | Palanker et al. | |
| 8,348,946 B2 | 1/2013 | McClurken | |
| 8,361,068 B2 | 1/2013 | McClurken | |
| 8,388,642 B2 | 3/2013 | Muni et al. | |
| 8,414,572 B2 | 4/2013 | Davison et al. | |
| 8,475,455 B2 | 7/2013 | McClurken | |
| 8,562,598 B2 | 10/2013 | Falkenstein et al. | |
| 8,568,409 B2 | 10/2013 | O'Brien et al. | |
| 8,632,533 B2 | 1/2014 | Greeley et al. | |
| 8,882,756 B2 | 11/2014 | Greeley et al. | |
| 8,906,012 B2 | 12/2014 | Conley et al. | |
| 8,920,417 B2 | 12/2014 | Conley et al. | |
| 8,979,842 B2 | 3/2015 | McNall, III et al. | |
| 9,113,896 B2 | 8/2015 | Mulier et al. | |
| 9,381,061 B2 | 7/2016 | McClurken et al. | |
| 9,445,858 B2 | 9/2016 | Conley et al. | |
| 9,486,283 B2 | 11/2016 | Greeley et al. | |
| 9,770,282 B2 | 9/2017 | Hoey et al. | |
| 2001/0018918 A1 | 9/2001 | Burnside et al. | |
| 2001/0032002 A1 | 10/2001 | McClurken et al. | |
| 2001/0038512 A1 | 11/2001 | Thomas, III | |
| 2001/0047183 A1 | 11/2001 | Privitera et al. | |
| 2002/0038129 A1 | 3/2002 | Peters et al. | |
| 2002/0049483 A1 | 4/2002 | Knowlton | |
| 2002/0058933 A1 * | 5/2002 | Christopherson | A61B 18/14 606/34 |
| 2002/0062131 A1 | 5/2002 | Gallo, Sr. | |
| 2002/0081871 A1 * | 6/2002 | Swayze | A61B 18/22 439/76.1 |
| 2002/0082643 A1 | 6/2002 | Kammerer et al. | |
| 2002/0165541 A1 * | 11/2002 | Whitman | A61B 18/1442 606/48 |
| 2002/0165549 A1 | 11/2002 | Owusu-Akyaw et al. | |
| 2002/0198519 A1 | 12/2002 | Qin et al. | |
| 2003/0004510 A1 * | 1/2003 | Wham | A61B 18/1445 606/51 |
| 2003/0014050 A1 | 1/2003 | Sharkey et al. | |
| 2003/0032954 A1 | 2/2003 | Carranza et al. | |
| 2003/0045872 A1 | 3/2003 | Jacobs | |
| 2003/0073993 A1 | 4/2003 | Ciarrocca | |
| 2003/0097129 A1 | 5/2003 | Davison et al. | |
| 2003/0144656 A1 | 7/2003 | Ocel | |
| 2003/0191462 A1 | 10/2003 | Jacobs | |
| 2003/0204185 A1 | 10/2003 | Sherman et al. | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0024395 A1 | 2/2004 | Ellman et al. | |
| 2004/0044340 A1 | 3/2004 | Francischelli | |
| 2004/0049179 A1 | 3/2004 | Francischelli | |
| 2004/0055860 A1 * | 3/2004 | Huseman | H01H 13/7006 200/406 |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0111136 A1 | 6/2004 | Sharkey et al. | |
| 2004/0111137 A1 | 6/2004 | Shankey et al. | |
| 2004/0116923 A1 | 6/2004 | Desinger | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0186465 A1 | 9/2004 | Francischelli | |
| 2004/0202561 A1 | 10/2004 | Hershberger et al. | |
| 2004/0204679 A1 | 10/2004 | Visconti et al. | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0243163 A1 | 12/2004 | Casiano et al. | |
| 2004/0267326 A1 | 12/2004 | Ocel | |
| 2005/0010095 A1 | 1/2005 | Stewart et al. | |
| 2005/0033280 A1 | 2/2005 | Francischelli | |
| 2005/0037672 A1 | 2/2005 | Caveney et al. | |
| 2005/0069437 A1 | 3/2005 | Mittelstein et al. | |
| 2005/0090815 A1 | 4/2005 | Francischelli | |
| 2005/0090816 A1 | 4/2005 | McClurken et al. | |
| 2005/0143729 A1 | 6/2005 | Francischelli | |
| 2005/0165392 A1 | 7/2005 | Francischelli | |
| 2005/0171525 A1 | 8/2005 | Rioux et al. | |
| 2005/0203497 A1 * | 9/2005 | Speeg | A61B 18/24 606/15 |
| 2005/0209564 A1 | 9/2005 | Bonner | |
| 2005/0222566 A1 | 10/2005 | Nahahira | |
| 2005/0267454 A1 | 12/2005 | Hissong | |
| 2005/0277970 A1 | 12/2005 | Norman et al. | |
| 2005/0283148 A1 * | 12/2005 | Janssen | A61B 90/30 606/34 |
| 2006/0009756 A1 | 1/2006 | Francischelli | |
| 2006/0009759 A1 | 1/2006 | Christian | |
| 2006/0064085 A1 | 3/2006 | Schechter et al. | |
| 2006/0073048 A1 * | 4/2006 | Malackowski | A61M 3/0258 417/474 |
| 2006/0095032 A1 * | 5/2006 | Jackson | A61B 5/4233 606/41 |
| 2006/0106375 A1 | 5/2006 | Werneth et al. | |

(56) References Cited

U.S. PATENT DOCUMENTS

| | | | |
|---|---|---|---|
| 2006/0149225 A1* | 7/2006 | McClurken | A61B 18/12 606/34 |
| 2006/0245964 A1 | 11/2006 | Koslov | |
| 2006/0264921 A1* | 11/2006 | Deutsch | A61B 18/14 606/32 |
| 2007/0016185 A1 | 1/2007 | Tullis et al. | |
| 2007/0049920 A1 | 3/2007 | Bloom et al. | |
| 2007/0093808 A1 | 4/2007 | Mulier et al. | |
| 2007/0112343 A1 | 5/2007 | Mische et al. | |
| 2007/0118114 A1 | 5/2007 | Miller et al. | |
| 2007/0142775 A1 | 6/2007 | Visconti et al. | |
| 2007/0149965 A1 | 6/2007 | Gallo, Sr. et al. | |
| 2007/0173813 A1 | 7/2007 | Odom | |
| 2007/0208332 A1 | 9/2007 | Mulier et al. | |
| 2008/0004656 A1 | 1/2008 | Livneh | |
| 2008/0015490 A1 | 1/2008 | Hershberger et al. | |
| 2008/0015563 A1 | 1/2008 | Hoey et al. | |
| 2008/0058796 A1 | 3/2008 | O'Brien et al. | |
| 2008/0071270 A1 | 3/2008 | Desinger et al. | |
| 2008/0082097 A1* | 4/2008 | McPherson | A61B 18/16 606/35 |
| 2008/0103494 A1 | 5/2008 | Rioux et al. | |
| 2008/0114372 A1 | 5/2008 | Edwards et al. | |
| 2008/0207208 A1 | 8/2008 | Schutz | |
| 2008/0262489 A1 | 10/2008 | Steinke | |
| 2009/0138010 A1* | 5/2009 | DeCarlo | F16L 37/098 606/41 |
| 2009/0157075 A1* | 6/2009 | Wham | A61B 18/1206 606/40 |
| 2009/0222001 A1 | 9/2009 | Greeley et al. | |
| 2009/0248007 A1* | 10/2009 | Falkenstein | A61B 18/1445 606/33 |
| 2009/0264879 A1 | 10/2009 | Bloom et al. | |
| 2009/0270896 A1 | 10/2009 | Sullivan et al. | |
| 2009/0306639 A1* | 12/2009 | Nevo | G16H 40/67 705/2 |
| 2009/0306655 A1 | 12/2009 | Stangeness | |
| 2010/0069904 A1 | 3/2010 | Cunningham | |
| 2010/0100095 A1 | 4/2010 | Bloom et al. | |
| 2010/0160906 A1 | 6/2010 | Jarrard | |
| 2010/0168743 A1 | 7/2010 | Stone et al. | |
| 2010/0204560 A1 | 8/2010 | Salahieh et al. | |
| 2010/0241178 A1 | 9/2010 | Tilson et al. | |
| 2010/0256624 A1* | 10/2010 | Brannan | A61B 18/1815 606/33 |
| 2010/0298763 A1 | 11/2010 | Adams et al. | |
| 2011/0009856 A1 | 1/2011 | Jorgensen et al. | |
| 2011/0028965 A1 | 2/2011 | McClurken | |
| 2011/0125146 A1 | 5/2011 | Greeley et al. | |
| 2011/0137298 A1 | 6/2011 | Nguyen et al. | |
| 2011/0178515 A1 | 7/2011 | Bloom et al. | |
| 2011/0196367 A1 | 8/2011 | Gallo | |
| 2011/0295249 A1 | 12/2011 | Bloom et al. | |
| 2011/0301578 A1 | 12/2011 | Muniz-Medina et al. | |
| 2011/0319889 A1 | 12/2011 | Conley et al. | |
| 2012/0004657 A1 | 1/2012 | Conley et al. | |
| 2012/0221035 A1 | 2/2012 | Harvey | |
| 2012/0071712 A1 | 3/2012 | Manwaring et al. | |
| 2012/0095461 A1 | 4/2012 | Herscher et al. | |
| 2012/0101496 A1 | 4/2012 | Davison et al. | |
| 2012/0116397 A1 | 5/2012 | Rencher et al. | |
| 2012/0143293 A1 | 6/2012 | Mauch et al. | |
| 2012/0151165 A1 | 6/2012 | Conley et al. | |
| 2012/0157989 A1 | 6/2012 | Stone et al. | |
| 2012/0184983 A1 | 7/2012 | Chang et al. | |
| 2012/0191084 A1 | 7/2012 | Davison et al. | |
| 2012/0191117 A1 | 7/2012 | Palmer et al. | |
| 2012/0253343 A1 | 10/2012 | McClurken et al. | |
| 2013/0066310 A1 | 3/2013 | Manwaring et al. | |
| 2013/0158535 A1 | 6/2013 | Denis et al. | |
| 2013/0197502 A1 | 8/2013 | Manwaring et al. | |
| 2014/0188105 A1 | 7/2014 | Conley et al. | |
| 2014/0276793 A1 | 9/2014 | Bloom | |

FOREIGN PATENT DOCUMENTS

| | | |
|---|---|---|
| JP | 62/204739 | 9/1987 |
| JP | 2009/504313 | 2/2009 |
| WO | 96/37156 | 11/1996 |
| WO | 97/23169 | 7/1997 |
| WO | 98/38932 | 9/1998 |
| WO | 2007/037785 | 4/2007 |
| WO | WO20070377785 | 4/2007 |
| WO | 2010/141417 | 9/2010 |
| WO | WO2010141417 | 12/2010 |

OTHER PUBLICATIONS

International Search Report and Written Opinion dated Nov. 8, 2010 for PCT Appln No. PCT/US2010/048115, filed Sep. 8, 2010, 10 pages.

Partial Translation of Japanese Patent Laid-Open No. S62-204739.

* cited by examiner

SURGICAL DEVICE

CROSS REFERENCE TO RELATED APPLICATIONS

This application is a continuation application of U.S. Ser. No. 12/877,400, filed Sep. 8, 2010 which claims priority to U.S. Provisional Application Ser. No. 61/240,562 filed Sep. 8, 2009, which are incorporated by reference herein to the extent it is consistent.

FIELD

This invention relates generally to the field of medical devices, systems and methods for use upon a human body during surgery. More particularly, the invention relates to electrosurgical devices, systems and methods that provide for cutting of tissue in addition to coagulation, hemostasis, and sealing of tissue to inhibit blood and other fluid loss during surgery, such as abdominal, orthopedic, head, spine and thoracic surgery as well as general surgery of the body.

BACKGROUND

U.S. Patent Application Publication No. 2002/0198519 A1 published Dec. 26, 2002 in the name of Qin et al. discloses an integrated device having a radio frequency generator 38, controller 52 with I/O device 54, and a fluid delivery apparatus 44 within a single housing 400. Electrical connection of a disclosed treatment device 26a/26b to the integrated device is performed by connecting an electrical connector 408 of the treatment device 26a/26b to electrical connector 402 of the integrated device. Device 26a/26b can also be connected via tubing 12 to the fluid delivery apparatus 44, to convey processing fluid for discharge by or near an operative element 36a/36b.

From Qin et al., since the connection of electrical connector 408 to electrical connector 402 and tubing 12 to fluid delivery apparatus 44 are performed separately and not integrated, the time for preparing the system for use may be increased or delayed if one individual is preparing the system, or two individuals may be required to prepare the system if the electrical connection and fluid connection are to be preformed simultaneously.

In addition, as shown in Qin et al., fluid delivery apparatus 44 includes a pump rotor 428. As indicated, the physician can couple the source of cooling liquid to the appropriate port on the handle of the device 26a/26b and load the tubing leading from the source of cooling liquid in the pump rotor 428. However, it may be possible to install the tubing improperly, for example, in the wrong direction (i.e. backwards) in such a way that the pump rotor 428 pumps fluid towards the source of cooling liquid rather than device 26a/26b. Furthermore, even if the direction of the tubing is proper, it may be possible to misalign the tubing with the pump rotor 428 such that the rotor 428 does not interact properly with the tubing causing a restriction in fluid flow, such as by improperly pinching the tubing, or even damaging the tubing, such as causing a leak. Also, if fluid is introduced into the tubing 12 before the tubing 12 is installed in fluid delivery apparatus 44 it may be possible for the fluid to flow uninhibited through the tubing and leak from treatment device 26a/26b. As a result, the foregoing installation errors, set-up and use of the equipment may be further delayed.

In light of the above, what is needed is a structure, method and system in which a tissue treatment device can be connected to a power delivery apparatus, such as a radio-frequency generator, and a fluid delivery apparatus, such as a pump, while overcoming the aforementioned deficiencies in the art, and may enable a single individual to connect the device to both of the power delivery apparatus and fluid delivery apparatus substantially simultaneously and without installation error to expedite use thereof.

SUMMARY

In one embodiment, the invention may comprise source equipment for use with a tissue treatment device, with the source equipment comprising a power delivery apparatus to deliver power provided from a power source to the tissue treatment device and a fluid delivery apparatus to deliver a fluid provided from a fluid source to the tissue treatment device.

The power delivery apparatus may comprise a radio-frequency power delivery apparatus to deliver radio-frequency power from a radio-frequency power source to the tissue treatment device. The radio-frequency power source may comprise a radio-frequency generator located in an electrosurgical unit.

The fluid delivery apparatus may comprise a pump, more particularly a peristaltic pump and even more particularly a rotary peristaltic pump. The fluid source may comprise a container containing a fluid, such as a bag containing a liquid. More particularly, the fluid source may comprise an I.V. bag containing normal (physiologic or 0.9%) saline solution.

The source equipment may comprise an electrosurgical unit and the tissue treatment device may comprise an electrosurgical tissue treatment device, such as a radio-frequency electrosurgical therapeutic device.

The source equipment may comprise a docking assembly comprising the power delivery apparatus and the fluid delivery apparatus. The docking assembly may be operable with a cartridge assembly configured to couple the tissue treatment device with the source equipment.

The source equipment, and more particularly the docking assembly, may be configured to engage with and disengage from the cartridge assembly. The source equipment, and more particularly the docking assembly, may be configured to engage the cartridge assembly with an interference fit.

The source equipment may include a releasable mechanical engagement mechanism configured to engage with the cartridge assembly. The source equipment may also include a releasable positioning mechanism to position the cartridge assembly.

The power delivery apparatus and/or the fluid delivery apparatus may be capable of being in a use position or a non-use position. The power delivery apparatus and/or the fluid delivery apparatus may be movable, such as by mechanical movement, to engage with the cartridge member or disengage from the cartridge assembly. The power delivery apparatus and/or fluid delivery apparatus may be movable by operation of an actuator (e.g. motor) or manually (e.g. by hand). The power delivery apparatus and fluid delivery apparatus may be simultaneously and/or jointly moveable. The power delivery apparatus and/or the fluid delivery apparatus may be arranged to operate with a cartridge member to be placed in a cartridge receptacle of the source equipment.

In another embodiment, the invention may comprise a cartridge assembly configured to couple a tissue treatment device with source equipment comprising a power delivery apparatus and a fluid delivery apparatus, with the cartridge assembly comprising a cartridge member which may be operable with the power delivery apparatus of the source equipment and the fluid delivery apparatus of the source equipment.

The cartridge assembly may comprise an electrosurgical cartridge assembly, the source equipment may comprise an electrosurgical unit having a radio-frequency power delivery apparatus and a fluid delivery apparatus and the tissue treatment device may comprise an electrosurgical tissue treatment device, such as a radio-frequency electrosurgical therapeutic device.

The cartridge member may be configured to receive a radio-frequency power output from the electrosurgical unit, which may comprise bipolar radio-frequency power or monopolar radio-frequency power. The cartridge member may be electrically coupled to one or more electrodes of the tissue treatment device to provide the radio-frequency power output to the one or more electrodes.

The cartridge member may be configured to mate and releaseably engageable with the electrosurgical unit, wherein the cartridge member and the electrosurgical unit may be configured to engage with and configured to disengage from each other. The cartridge member may be configured to engage with a releasable and/or mechanical engagement mechanism of the electrosurgical unit. The cartridge member may also be configured to engage the electrosurgical unit with an interference fit. The cartridge member may include a cartridge body configured to fit within and otherwise mate with a receptacle of the electrosurgical unit.

The cartridge assembly may include a fluid delivery passage, which may be operable with the fluid delivery apparatus of the electrosurgical unit. The cartridge member may include a valve, with the valve in fluid communication with the fluid delivery passage. The valve may at least partially close the fluid delivery passage when the fluid delivery apparatus is inactive. The valve may comprise a check valve and more precisely a diaphragm check valve.

The cartridge member may include a cartridge body. At least a portion of the fluid delivery passage may be located in and/or defined by the cartridge body.

At least a portion of the fluid delivery passage may be defined by plastic tubing (e.g. a length of the fluid delivery passage may be defined by a length of tubing). At least a portion of the plastic tubing may be may be operable with the fluid delivery apparatus of the electrosurgical unit. More particularly, at least a portion of the plastic tubing may be configured to be compressed by the fluid delivery apparatus of the electrosurgical unit.

At least a portion of the plastic tubing may be located in and/or supported by the cartridge body. The plastic tubing may also be located in a recess formed in an outer surface of the cartridge body.

At least a portion of the plastic tubing may form an enclosed loop with the cartridge body. A length of the plastic tubing forming the loop may be adjustable to adjust a size (e.g. perimeter or diameter) of the loop. In particular, the plastic tubing may be movable at least one of into and out of a tubular aperture which extends through the cartridge body to adjust a size of the loop. The loop may expand as it extends away from the cartridge body.

At least a portion of the plastic tubing may be supported in an arcuate shape by the cartridge body. The arcuate shape may comprise a semi-circular shape.

The cartridge body may include a surface against which the plastic tubing may be compressed during an operation of the fluid delivery apparatus. The surface may comprise an arcuate surface and more particularly comprise a semi-circular surface.

The plastic tubing may be supported on opposing terminal ends by the cartridge body and be unsupported therebetween. A portion of the cartridge body may be located within a lumen of the plastic tubing and form an interference fit therewith to support the tubing on the opposing terminal ends.

The cartridge member may be configured to receive a control signal from the electrosurgical unit, as well as configured to send the control signal back to the electrosurgical unit. The control signal may comprise a signal configured to control a radio-frequency power output of the electrosurgical unit. The cartridge member may be electrically coupled to a radio-frequency power activation switch of the tissue treatment device (e.g. on the hand-piece) to provide the signal to the radio-frequency power activation switch.

The cartridge assembly, and in particular the cartridge member, may include tissue treatment device information, and may be configured provide the tissue treatment device information to the electrosurgical unit, with the tissue treatment device information in a format which may be readable by the electrosurgical unit. The cartridge member may include a tangible storage medium and the tangible storage medium may be configured to store the tissue treatment device information.

The tissue treatment device information may comprise at least one operating parameter operable with a use of the tissue treatment device. The tissue treatment device information may comprise at least one of a radio-frequency power delivery apparatus setting (e.g. power level) and a fluid delivery apparatus setting (e.g. flow rate) operable with a use of the tissue treatment device. The tissue treatment device information may also comprise a plurality of power radio-frequency power delivery apparatus settings operable with a use of the tissue treatment device and at least one fluid delivery apparatus setting corresponding to each of the radio-frequency power delivery apparatus settings.

The tissue treatment device information may also comprise a default setting operable with a use of the tissue treatment device, a time interval operable with a use of the tissue treatment device or at least one identifier unique to the tissue treatment device.

The cartridge member may include a tangible storage medium. The tangible storage medium may comprise an electronic memory, which may further comprise a programmable read only memory.

The cartridge member may comprise an electrical contact connectable with an electrical contact of the electrosurgical unit, which may be located on a printed circuit board. The cartridge member electrical contact may comprise a male or female electrical connector configured to mate with a female or male electrical connector of the electrosurgical unit, respectively. The electrical contact may be comprises at least one of a blade, a pad, a pin, a prong and a strip.

In another embodiment, the invention may comprise a system, such as an electrosurgical system, including any of the source equipment, tissue treatment device and cartridge assembly as set forth herein. For example, the invention may comprise a system, such as an electrosurgical system, with the system comprising an electrosurgical unit comprising a radio-frequency power delivery apparatus and a fluid delivery apparatus; a tissue treatment device; and a cartridge assembly operable with the radio-frequency power delivery apparatus and the fluid delivery apparatus of the electrosurgical unit to provide radio-frequency power and a fluid to the tissue treatment device.

In another embodiment, the invention may comprise a method, such as a method of operating an electrosurgical system, with the method comprising providing an electrosurgical unit, with the unit comprising a radio-frequency power delivery apparatus and a fluid delivery apparatus, wherein the radio-frequency power delivery apparatus and the fluid delivery apparatus are operable with a cartridge assembly configured to couple a tissue treatment device with the electrosurgical unit; providing the cartridge assembly; engaging the cartridge assembly with the radio-frequency power delivery apparatus of the electrosurgical unit; and engaging the cartridge assembly with the fluid delivery apparatus of the electrosurgical unit.

Engaging the cartridge assembly with the radio-frequency power delivery apparatus of the electrosurgical unit may comprise contacting an electrical contact of the cartridge assembly with an electrical contact of the radio-frequency power delivery apparatus.

Engaging the cartridge assembly with the fluid delivery apparatus of the electrosurgical unit may comprise contacting a plastic tubing of the cartridge member with an element of the fluid delivery apparatus.

Engaging the cartridge assembly with the radio-frequency power delivery apparatus of the electrosurgical unit may comprise moving the radio-frequency power delivery apparatus from a non-use position to a use position, and engaging the cartridge assembly with the fluid delivery apparatus of the electrosurgical unit may comprise moving the fluid delivery apparatus from a non-use position to a use position.

In another embodiment, the invention may provide another method, such as a method of operating an electrosurgical system, with the method comprising providing an electrosurgical unit having a power delivery apparatus and a fluid delivery apparatus, wherein the power delivery apparatus and the fluid delivery apparatus are arranged to operate with a cartridge member to be placed in a cartridge receptacle of the electrosurgical unit; providing the cartridge member; placing the cartridge member in the cartridge receptacle of the electrosurgical unit; engaging the cartridge member with the power delivery apparatus of the electrosurgical unit; and engaging the cartridge member with the fluid delivery apparatus of the electrosurgical unit.

Engaging the cartridge member with the power delivery apparatus of the electrosurgical unit may comprise contacting an electrical contact of the cartridge member with an electrical contact of the power delivery apparatus.

Engaging the cartridge member with the fluid delivery apparatus of the electrosurgical unit may comprise compressing a fluid delivery tubing segment of the cartridge member with a compression element of the fluid delivery apparatus.

Engaging the cartridge member with the power delivery apparatus of the electrosurgical unit may comprise moving the power delivery apparatus from a non-use position to a use position; and engaging the cartridge member with the fluid delivery apparatus of the electrosurgical unit may comprise moving the fluid delivery apparatus from a non-use position to a use position. The power delivery apparatus and fluid delivery apparatus may be moved simultaneously and/or jointly.

In the foregoing manner, it may be possible for a single individual to connect a tissue treatment device to both of a power delivery apparatus and fluid delivery apparatus substantially simultaneously and without installation error to expedite use thereof.

BRIEF DESCRIPTION OF THE DRAWINGS

The invention may be more completely understood in consideration of the following detailed description of various embodiments of the invention in connection with the accompanying drawings, in which.

DETAILED DESCRIPTION

Figure 1:
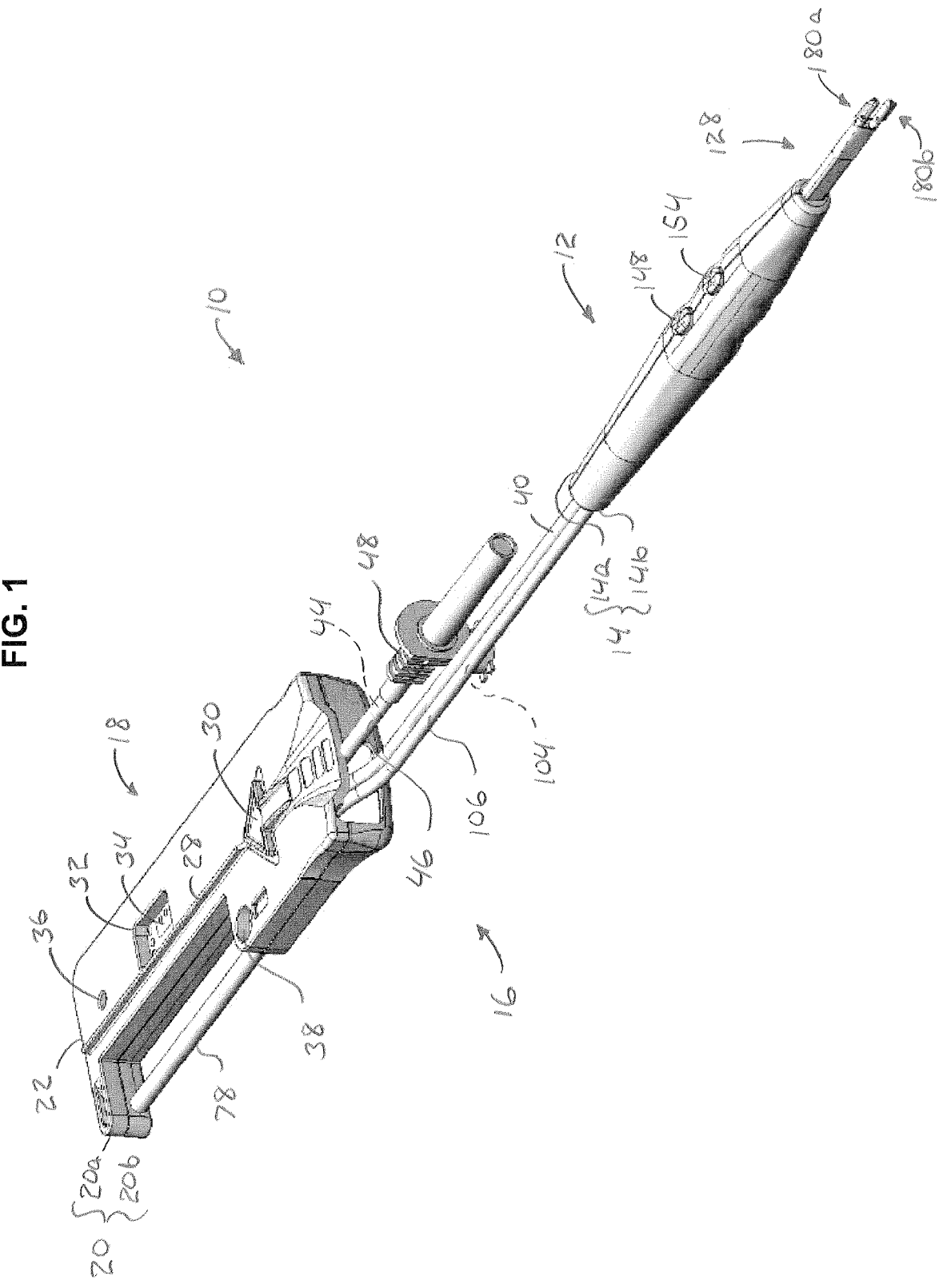
FIG. 1 is a perspective view of an electrosurgical tissue treatment device and a cartridge assembly having a cartridge member to connect a hand-piece of the device to an electrosurgical unit according to one embodiment of the invention.

Throughout the description, like reference numerals and letters indicate corresponding structure as may also be shown in the figures. Also, any particular feature(s) of a particular embodiment may be equally applied to any other embodiment(s) of this specification as suitable. In other words, features between the various embodiments described herein are interchangeable as suitable, and not exclusive. From the specification, it should be clear that any use of the terms "distal" and "proximal" are made in reference from the user of the device, and not the patient.

The inventions disclosed herein provide devices, systems and methods for treating tissue at a tissue treatment site during an electrosurgical procedure. Among other features, the inventions disclosed herein are particularly useful for procedures where it may be desirable to cut tissue, as well as shrink, coagulate and seal tissue against blood and other fluid loss, for example, by shrinking lumens of blood vessels (e.g., arteries, veins).

The invention will now be discussed with reference to the figures, with FIG. 1 showing an exemplary handheld electrosurgical device 10 to treat tissue according to one embodiment of the present invention, which may be used in conjunction with a system of the present invention. Accordingly, it should be understood that the structure of device 10 is not intended to be limiting as to the scope of devices, particularly tissue treatment (therapeutic) devices, which can be used with the system of the invention. As may be understood, therapeutic devices pertain to devices which treat tissue to cure diseases, relieve pain or for other medical purposes.

As shown in FIG. 1, exemplary device 10 may comprise an elongated hand-piece 12 having a handle 14 provided by mating handle portions 14a, 14b. Hand-piece 12 may be slender to enable a user of device 10 to hold and manipulate device 10 between the thumb and index finger like a writing instrument such as a pen. Hand-piece 12 may comprise a sterilizable, rigid, electrically insulative material, such as a plastic material. Exemplary plastic materials may comprise polycarbonate (PC) and acrylonitrile-butadiene-styrene (ABS).

Figure 2:
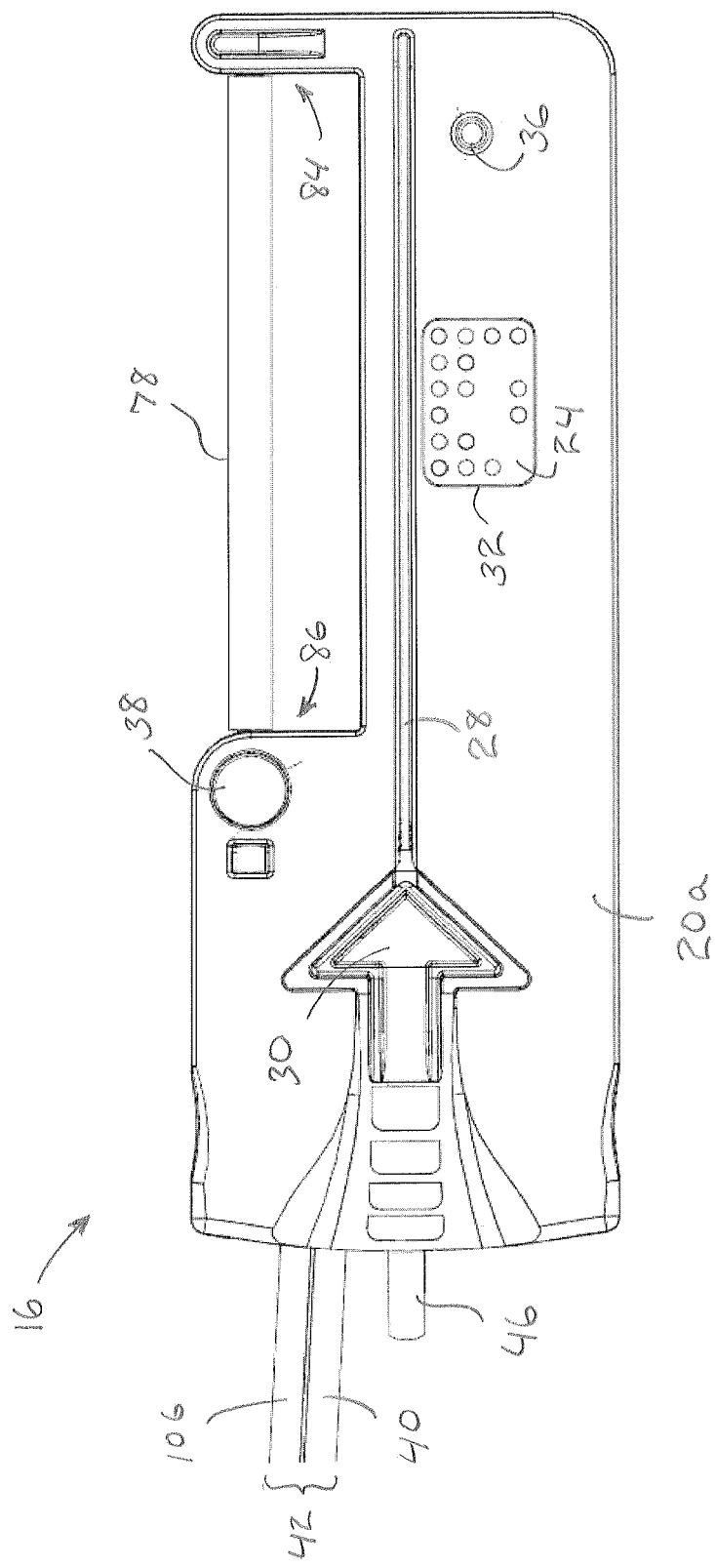
FIG. 2 is a top view of the cartridge member.
Figure 3:
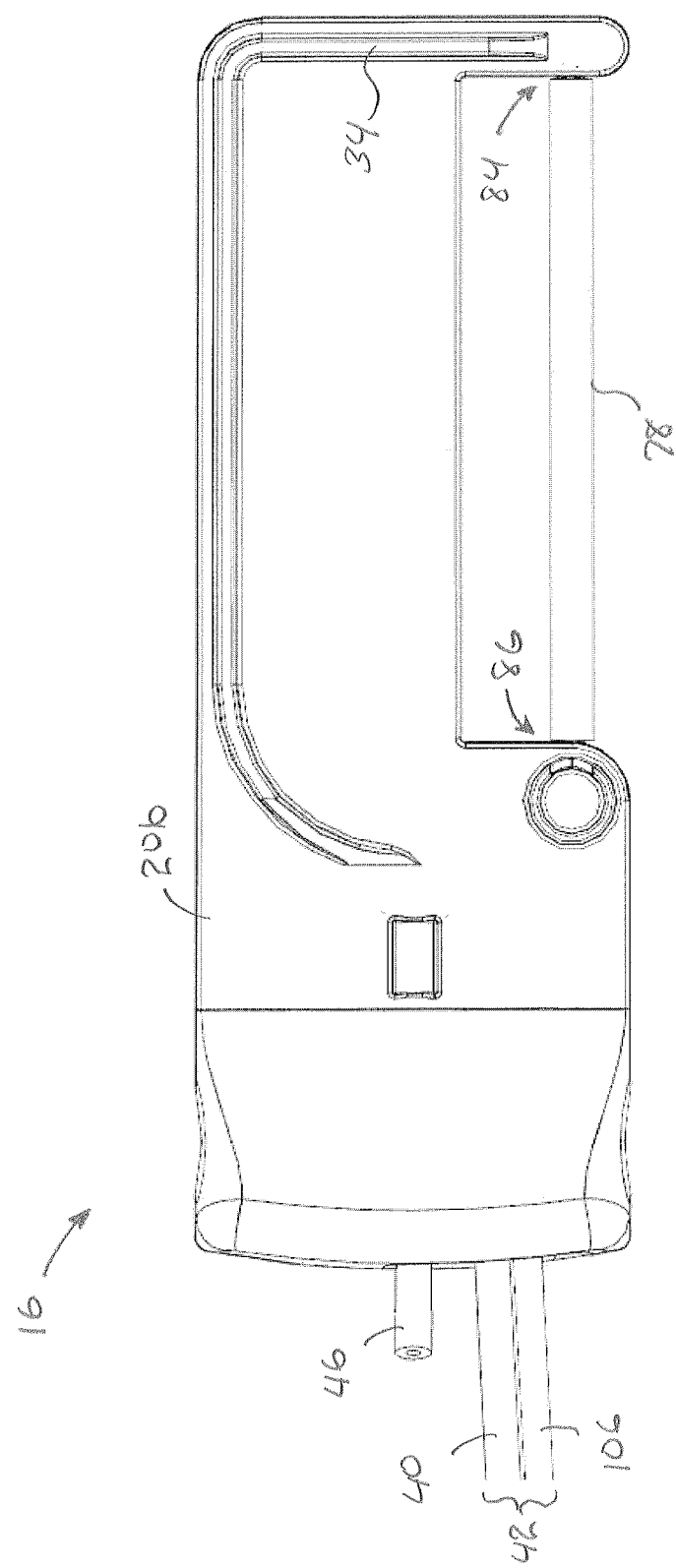
FIG. 3 is a bottom view of the cartridge member.

Device 10 may be coupled to an electrosurgical unit 300 (shown in FIG. 16) by a cartridge assembly 16 operable with electrosurgical unit 300. Cartridge assembly 16 may comprise a cartridge member 18 which, as shown in FIGS. 2 and 3, may comprise a substantially planar, elongated, rectangular cartridge body 20 comprising mating cartridge body portions 20a, 20b. To facilitate proper installation of cartridge member 18 with electrosurgical unit 300, cartridge body 20a may include a directional indicator 30 to show the direction in which cartridge member 18 is to be installed in electrosurgical unit 300, as well as which side of the cartridge member 18 is the top surface. Furthermore, cartridge body 20a may include a protruding element 28, shown in the form of an elongated rib, to physically prevent installation of the cartridge assembly 16 upside down. Cartridge body 20 may be made of a sterilizable, rigid, electrically insulative material, such as a plastic material. Exemplary plastic materials may comprise polycarbonate (PC) and acrylonitrile-butadiene-styrene (ABS).

Figure 37:
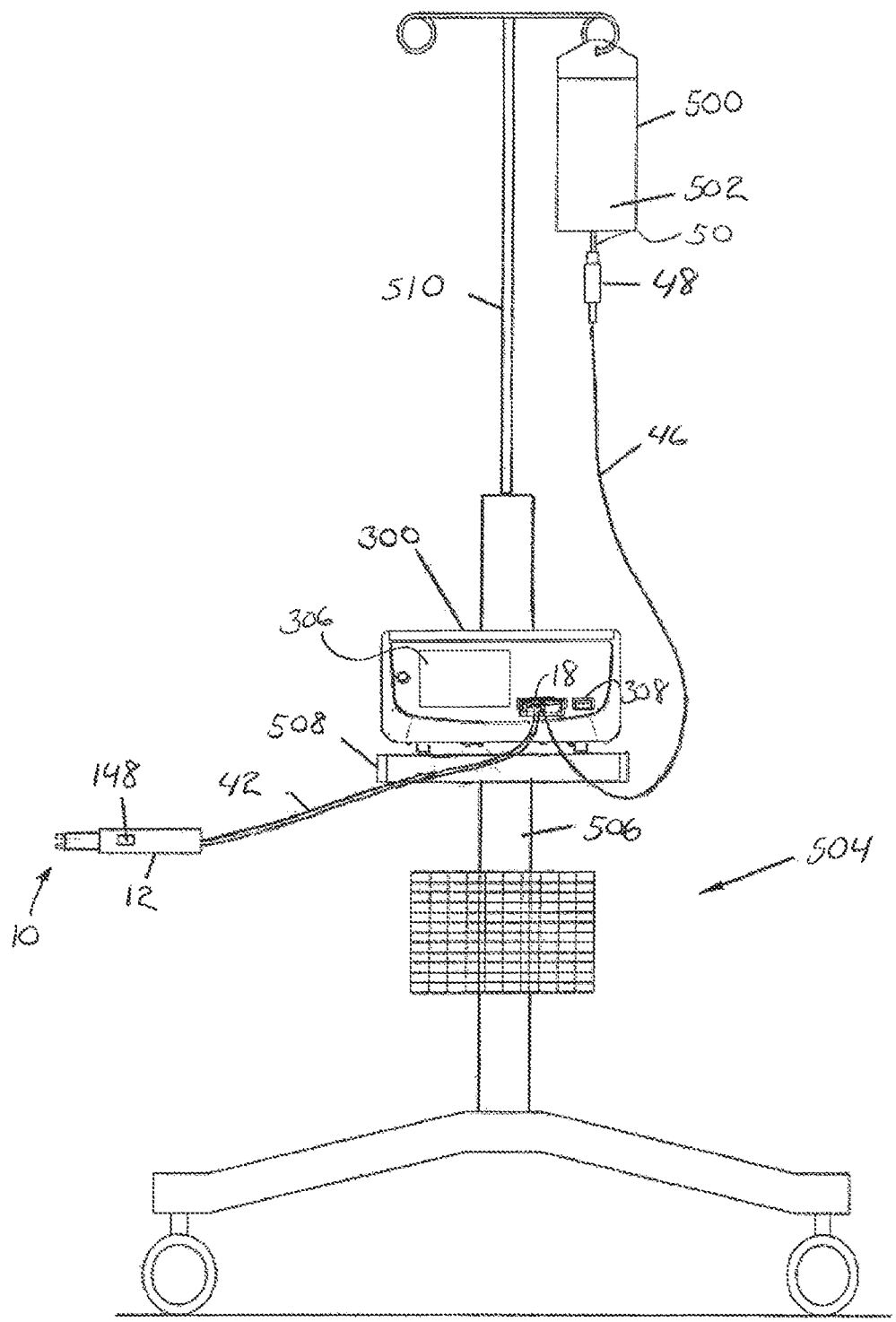
FIG. 37 is a front view of one embodiment of a system of the present invention having electrosurgical unit in combination with a fluid source and handheld electrosurgical tissue treatment device.

Referring briefly to FIG. 37, when device 10 is connected to other components as part of a system, fluid 502 from a fluid source 500, such as a bag of saline solution, may be communicated through an enclosed fluid passage provided by various structures. Fluid 502 may flow from the fluid source 500 into cartridge member 18 of cartridge assembly 16 through lumen 44 of flexible fluid delivery tubing segment 46. At one end, fluid delivery tubing segment 46 may particularly couple to fluid source 500 through a drip chamber 48 after the fluid source 500 may be penetrated with a spike 50 located at the end of the drip chamber 48 in a known manner. In other embodiments, drip chamber 48 may be eliminated and tubing segment 46 may be attached directly to a spike 50. Fluid delivery tubing segment 46 may be made of a plastic material, such as flexible polyvinyl chloride (PVC) or other flexible material such as an elastomer.

Figure 4:
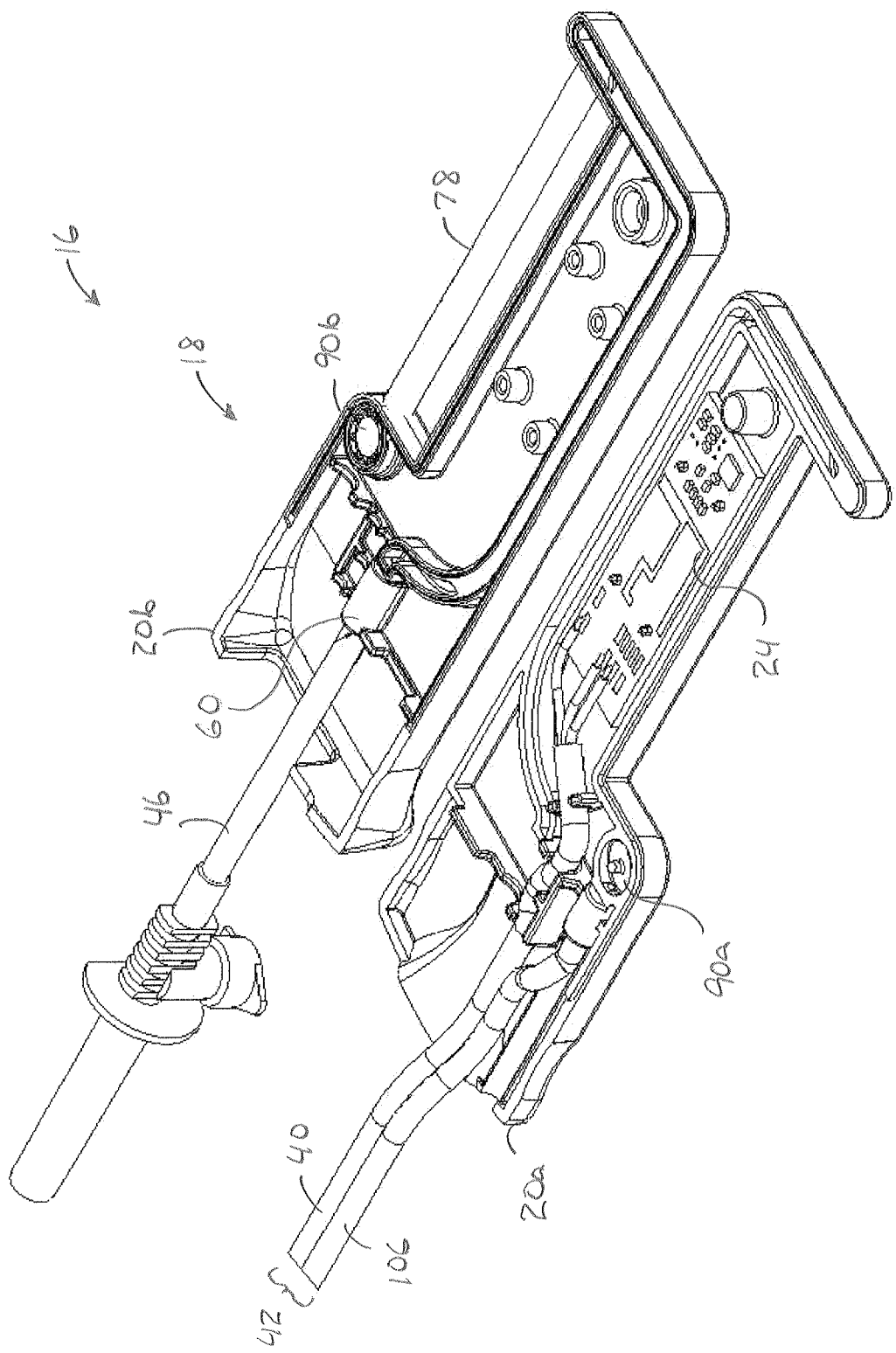
FIG. 4 is a perspective view of the cartridge assembly showing the inner components of the cartridge member.
Figure 5:
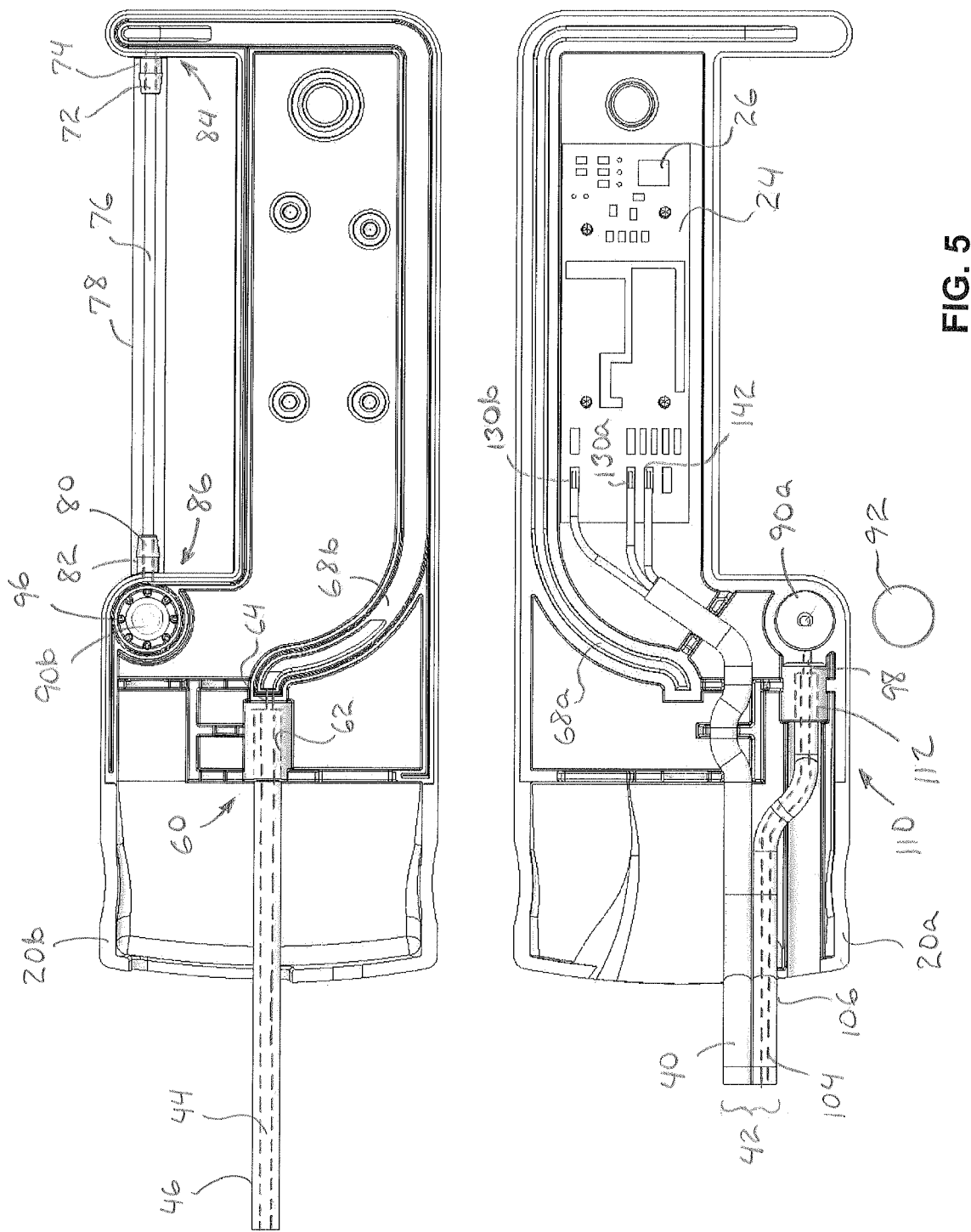
FIG. 5 is a plan view of the cartridge assembly showing the inner components of the cartridge member.

Referring now to FIGS. 4 and 5, at its opposite end, fluid delivery tubing segment 46 may be coupled and tightly fastened with a fluid tight connection to cartridge body 20b of cartridge member 18 via a female connector portion 60. More particularly, fluid delivery tubing segment 46 may be coupled to cartridge body 20b via a distal end portion of the tubing segment 46 extending into a cylindrical cavity 62 formed in cartridge body 20b to provide a cylindrical receptacle. The outer surface of fluid delivery tubing segment 46 may be configured to mate against and form a press (interference) fit seal with corresponding inner surfaces of connector portion 60 to provide a fluid tight seal there between. An adhesive or solvent bonding may be used there between to further strengthen the seal, or in lieu of the press fit.

Continuing with FIG. 5, from lumen 44 of fluid delivery tubing segment 46, the fluid passage may extend through a through hole 64 provided at the base of cavity 62 and may be next provided and defined by an elongated enclosed channel 68 formed by overlying portions of cartridge bodies 20a, 20b. More particularly, channel 68 may be formed by mating a channel portion 68a of cartridge body 20a with a channel portion 68b of cartridge body 20b and forming a continuous hermetic seal there between, particularly by vibration, ultrasonic or other plastic welding method. In the foregoing manner, a portion of the fluid delivery passage may be located in the cartridge assembly 16, and more particularly the cartridge member 18 (provided by tubing segment 46 and channel 68), and more particularly defined thereby (channel 68).

From channel 68, the fluid passage thereafter may extend through a through hole 72 formed in male connector portion 74, into lumen 76 of fluid delivery tubing segment 78 and thereafter through hole 80 formed in male connector portion 82. As shown in FIG. 5, fluid delivery tubing segment 78 may be coupled and tightly fastened with a fluid tight connection to cartridge body 20b of cartridge member 18 via male connector portions 74 and 82 provided by two spaced, parallel, fixed supports 84 and 86 at the opposite ends thereof. More particularly, fluid delivery tubing segment 78 may be coupled to cartridge body 20b via male connector portions 74 and 82 which extend into the lumen 76 of delivery tubing segment 78. The inner surface of lumen 76 of fluid delivery tubing segment 78 may be configured to mate against and form a press (interference) fit seal with corresponding outer surfaces of connector portions 74 and 82 to provide a fluid tight seal there between. An adhesive or solvent bonding may be used there between to further strengthen the seal, or in lieu of the press fit. Similar to fluid delivery tubing segment 46, fluid delivery tubing segment 78 may be made of a plastic material, such as flexible polyvinyl chloride (PVC) or other flexible material such as an elastomer.

In the foregoing manner, the cartridge assembly 16, and more particularly the cartridge member 18, supports tubing segment 78. More specifically, tubing segment 78 is supported on opposing ends by the cartridge member 18 with the cartridge member 18 within the lumen of the tubing segment 78.

It may be possible to replace fluid delivery tubing segment 78 to increase or decrease the fluid flow output of fluid delivery apparatus 420 (discussed in greater detail below) by changing the size (diameter) of lumen 76 of delivery tubing segment 78. Furthermore, fluid delivery tubing segment 78 may require a thicker cross-section and durability than the other fluid delivery tubing segments, such as fluid delivery tubing segment 46. For example, in a particular embodiment discussed in greater detail below, fluid delivery tubing segment 78 may be configured to be compressed by a fluid delivery apparatus 422 contained within electrosurgical unit 300, to force fluid 502 through the lumen 76 thereof in a known manner. In such instance, the thicker portion of the fluid delivery tubing for device 10 may be limited to fluid delivery tubing segment 78.

Continuing with FIG. 5, from through hole 80 of connector portion 82, the fluid passage extends into a cylindrical chamber 90 of a one-way (check) diaphragm valve 38 (FIG. 1) provided and defined chamber portions 90a and 90b which are separated by a flat disc shaped plastic membrane 92. With valve 38, fluid 502 only may flow in one direction. In use, when valve 38 is open, membrane 92 may be positioned towards the end of chamber portion 90a and fluid may be allowed to pass through chamber 90 and into through hole 98 to exit chamber 90. In order to inhibit back flow of fluid 502, when valve 38 is closed, membrane 92 may be positioned on seat 96 in a cavity of cartridge body 20b, which closes the fluid passage and fluid communication between the exit port provided by through hole 98 and the inlet port provided by through hole 80. Furthermore, membrane 92 inhibits fluid 502 from flowing through valve 38 if the fluid pressure is less than about 3.5 psi. In the foregoing manner, the cartridge assembly 16, and more particularly the cartridge member 18, may include a valve 38 in fluid communication with the fluid delivery passage. Also in this manner, fluid 502 may not flow through valve 38 to handpiece 12 in the event fluid 502 is introduced to the fluid passage before cassette member 18 may be installed in electrosurgical unit 300, but rather will only open to permit flow there through when a pressure of greater than 3.5 is provided by fluid delivery apparatus 420 after cartridge member 18 has been installed in electrosurgical unit 300.

From through hole 98, the fluid passage may extend into lumen 104 of fluid delivery tubing segment 106. Similar to fluid delivery tubing segment 46, tubing segment 106 may be coupled and tightly fastened with a fluid tight connection to cartridge body 20a of cartridge member 18 via a female connector portion 110. More particularly, fluid delivery tubing segment 106 may be coupled to cartridge body 20a via a distal end portion of the tubing segment 106 extending into a cylindrical cavity 112 formed by cartridge body 20a to provide a cylindrical receptacle. The outer surface of fluid delivery tubing segment 106 may be configured to mate against and form a press (interference) fit seal with corresponding inner surfaces of connector portion 110 to provide a fluid tight seal there between. An adhesive or solvent bonding may be used there between to further strengthen the seal, or in lieu of the press fit. As shown in FIG. 5, tubing segment 106 may be molded and formed unitary with cord 40, such as by plastic co-extrusion, to provide a single cable 42.

Alternatively, female connector portion 110 may be replaced with a male connector portion 74 having a through hole 72 as previously described. Fluid delivery tubing segment 106 may be coupled and tightly fastened with a fluid tight connection to cartridge body 20a of cartridge member 18 via male connector portion 74 being configured to extend into the lumen 104 of delivery tubing segment 106. The inner surface of lumen 104 of fluid delivery tubing segment 106 may be configured to mate against and form a press (interference) fit seal with corresponding outer surfaces of connector portion 74 to provide a fluid tight seal there between. An adhesive or solvent bonding may be used there between to further strengthen the seal, or in lieu of the press fit. In the foregoing manner, fluid may be allowed to pass through chamber 90 and into through hole 72 to exit chamber 90 and into lumen 104 of fluid delivery tubing segment 106.

Figure 6:
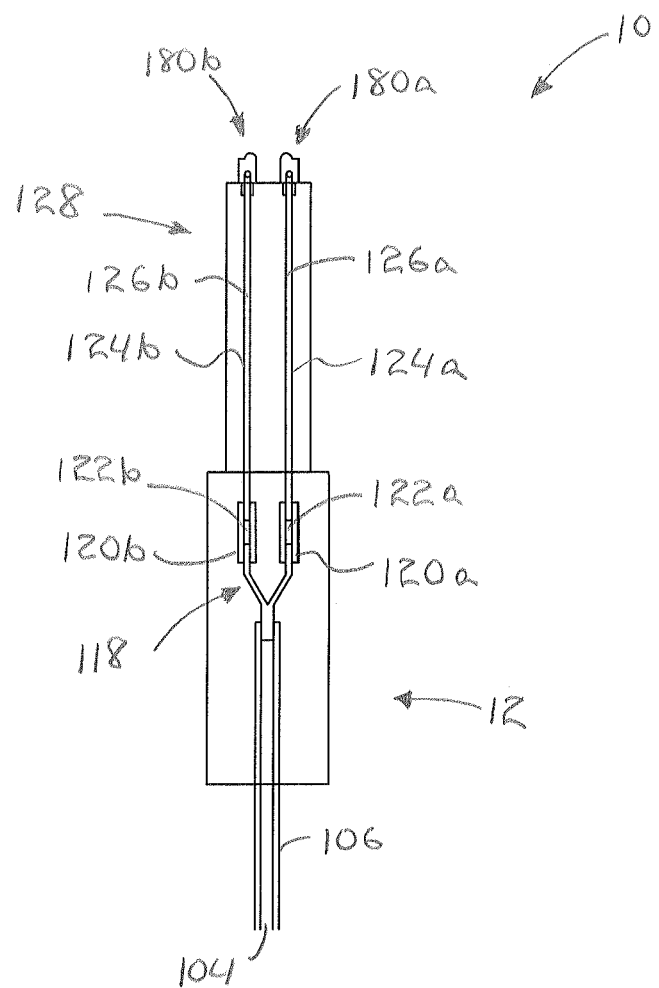
FIG. 6 is a plan view showing certain fluid passages of the electrosurgical tissue treatment device.

Referring to FIG. 6, fluid delivery tubing segment 106 may enter the proximal end of hand-piece 12 of device 10. Within hand-piece 12 of device 10, fluid delivery tubing segment 106 may be connected to the inlet branch of a Y-splitter 118, which thereafter provides two outlet branches which are connected to the proximal ends of fluid delivery tubing segments 120a, 120b. The distal ends of delivery tubing segments 120a, 120b may thereafter be connected to the proximal ends of shafts 124a, 124b. To connect fluid delivery tubing segments 120a, 120b to shafts 124a, 124b, the lumens 122a, 122b of the fluid delivery tubing segments 120a, 120b may be interference fit over the outside diameter of shafts 124a, 124b to provide an interference fit seal there between. An adhesive or solvent bonding may be used there between to further strengthen the seal, or in lieu of the press fit. Fluid 502 may then flow through the lumens 126a, 126b of shafts 124a, 124b and thereafter exit from device 10 as discussed in greater detail below.

Additionally, device 10 may include an aspiration/suction tubing segment to remove fluid 502 from a tissue treatment site. The suction tubing segment may pass through cartridge member 18 and thereafter be connected to a vacuum source.

In addition to operating in conjunction with a fluid delivery apparatus 422 within electrosurgical unit 300, as discussed in greater detail below, cartridge assembly 16 also operates in conjunction with a radio-frequency power delivery apparatus 440 and other electrical components and circuits within electrosurgical unit 300. More particularly, radio-frequency power delivery apparatus 440 and fluid delivery apparatus 420 may be components of a docking assembly 340 of electrosurgical unit 300 which is operable with the cartridge assembly 16 configured to couple device 10 with electrosurgical unit 300.

As shown in FIGS. 1 and 2, as well as FIGS. 4 and 5, cartridge member 18 includes a two layer printed circuit board 24, one side of which may be exposed through an aperture 32 in cartridge body 20a of cartridge member 18 to provide an electrical communication with electrosurgical unit 300. Printed circuit board 24 may comprise a 0.05-0.07 inch thick base insulator with top and bottom conductive layers deposited thereon. The exposed conductive layers may comprise 2-6 microns of gold over 100-300 microns of electroless nickel over copper. Detailed drawings of printed circuit board 24 may be found in FIGS. 7-11.

As shown in FIGS. 7-11, printed circuit board 24 includes a plurality of electrical contacts thereon, which may comprise electrical contact pads to electrically connectable with corresponding electrical contacts of electrosurgical unit 300. Certain of these electrical contacts and their associated function will now be discussed.

Figure 7:
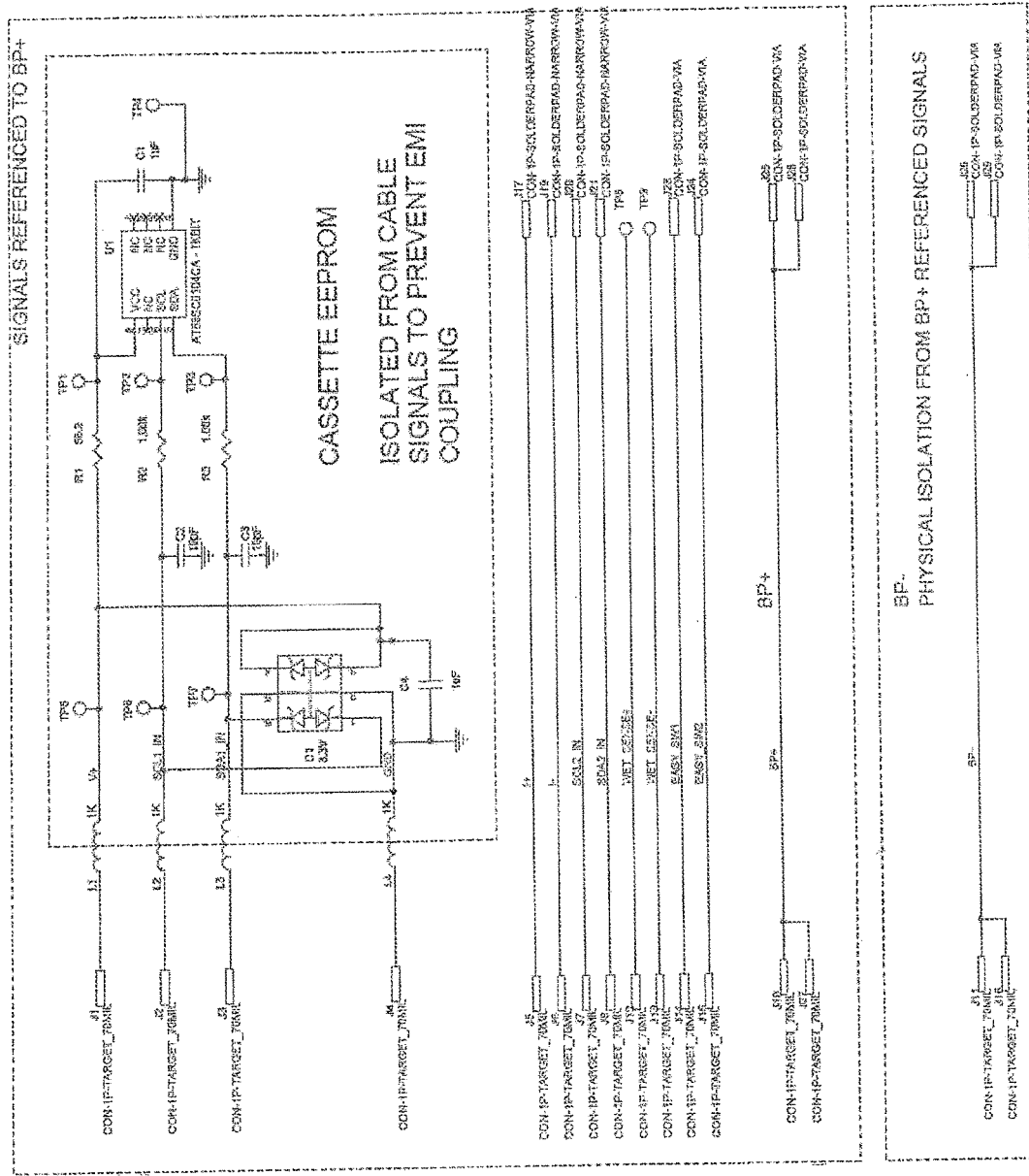
FIG. 7 is a diagram of the various electrical connections of a printed circuit board assembly provided with the cartridge member.
Figure 8:
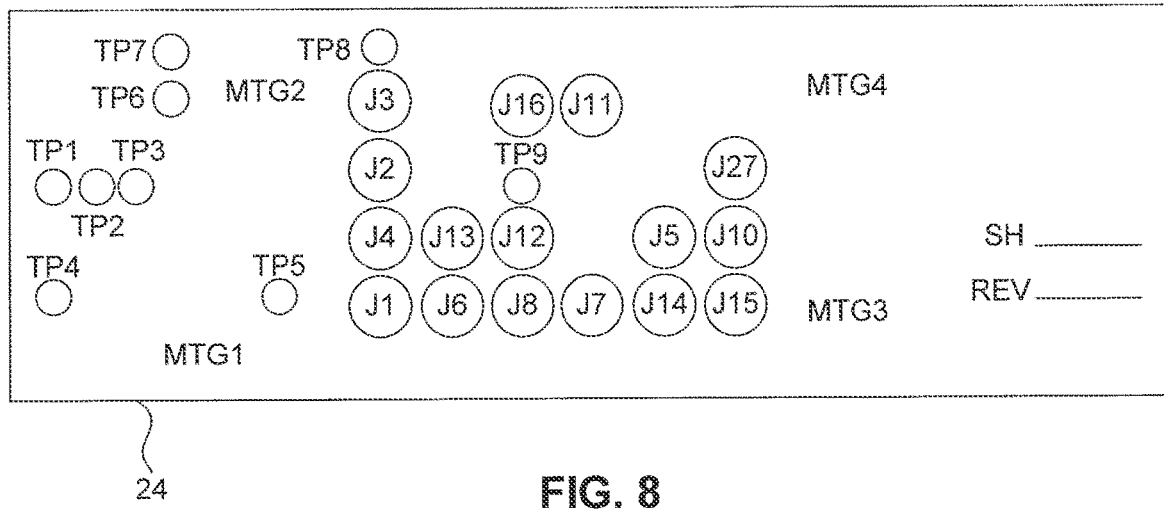
FIG. 8 is a top plan view of the printed circuit board assembly.
Figure 9:
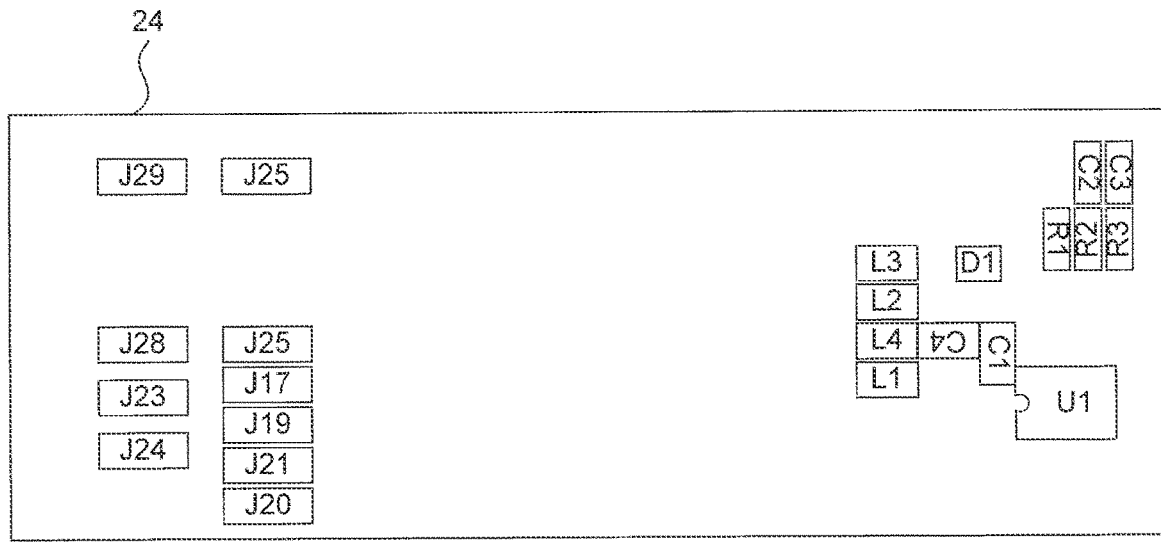
FIG. 9 is a bottom plan view of the printed circuit board assembly.
Figure 10:
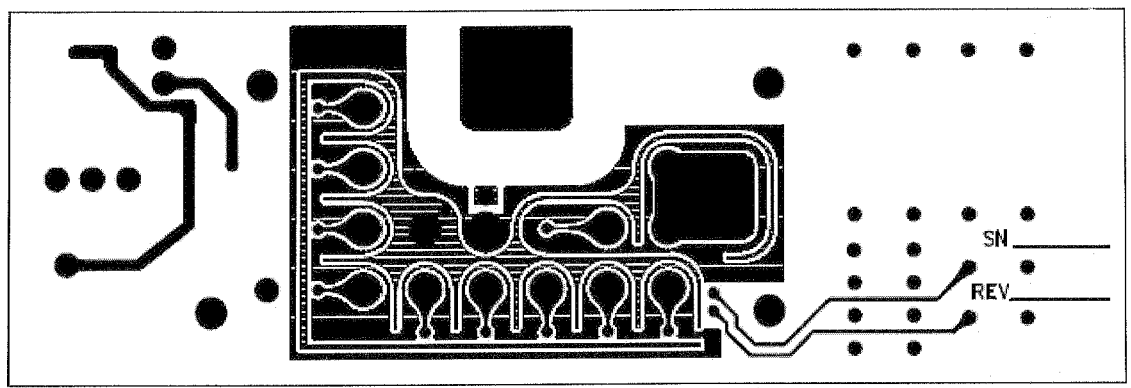
FIG. 10 is a top view of the upper (top) layer of the printed circuit board assembly.
Figure 11:
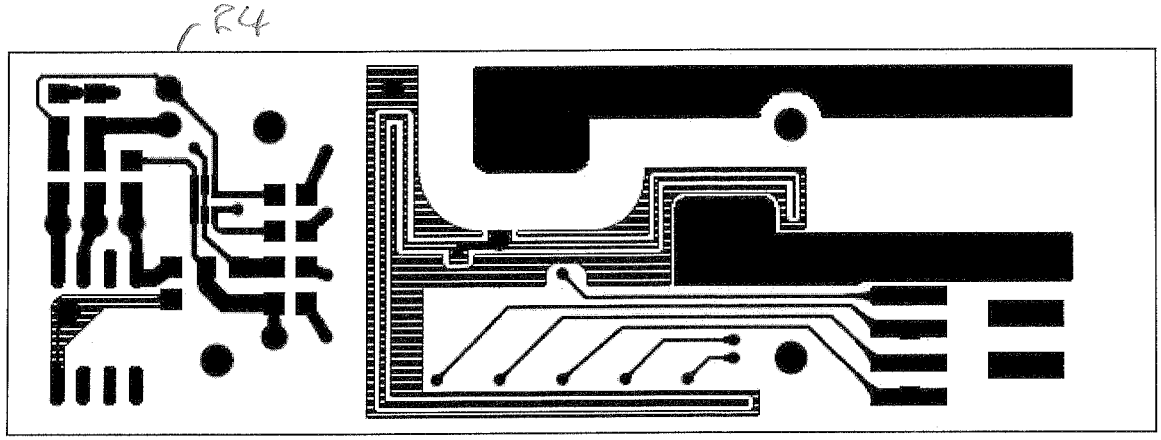
FIG. 11 is a top view of the lower (bottom) layer of the printed circuit board assembly.

Bipolar radio-frequency power from electrosurgical unit 300 may be provided from outputs BP+ and BP− thereof. As shown in FIG. 7, electrical contacts J10/J27 may receive power from bipolar power output BP+ which may then communicated along an electrically conductive pathway to electrical contacts J25/J28. Electrical contacts J11/J16 may receive power from bipolar power output BP− which may then communicated along an electrically conductive pathway to electrical contacts J26/J29. Electrical contacts J10/J27 and J11/J16 are shown in FIG. 8, while electrical contacts J25/J28 and J26/J29 are shown in FIG. 9.

Figure 12:
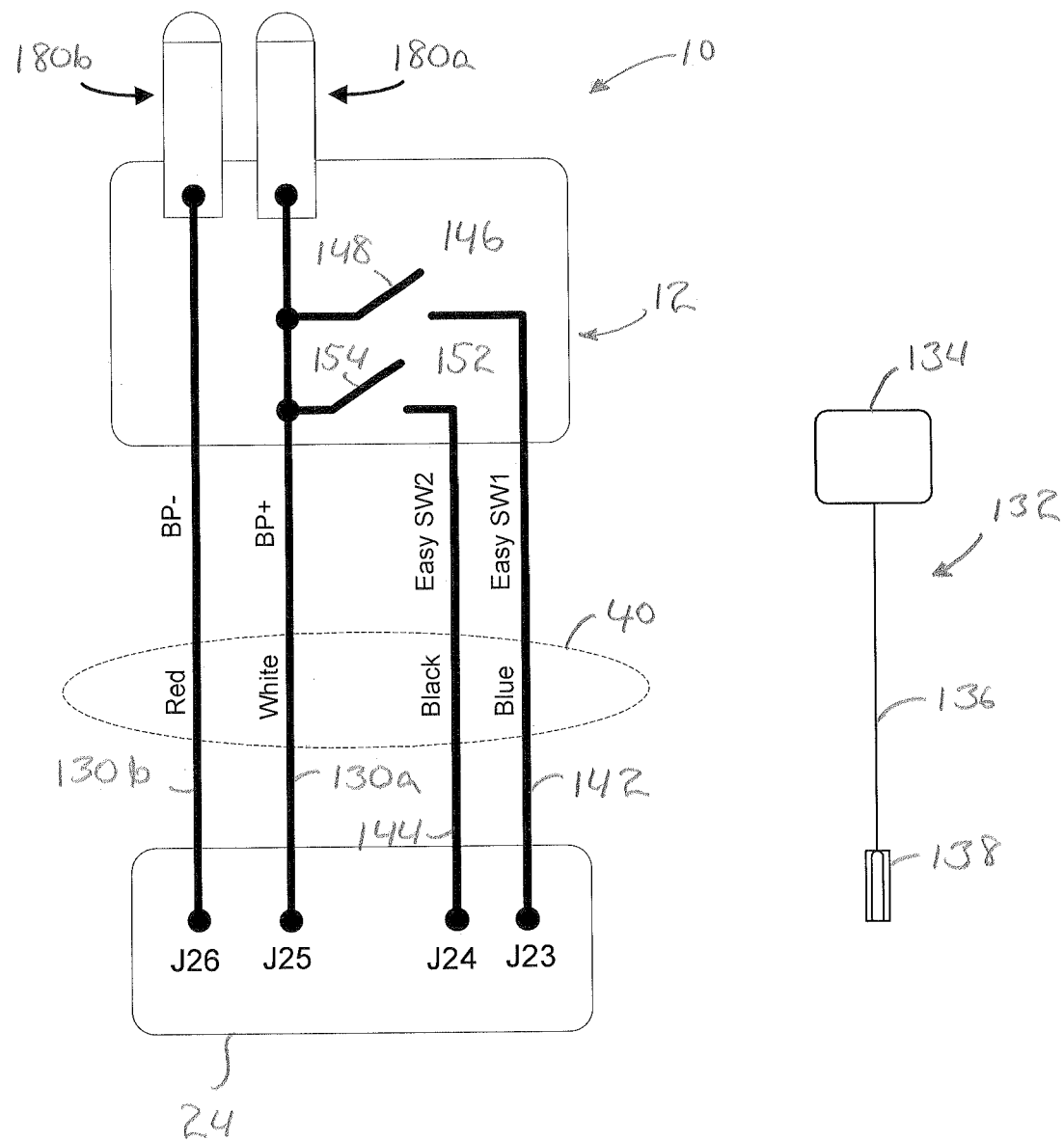
FIG. 12 is a plan view showing certain electrical connections of the electrosurgical tissue treatment device.

As best shown in FIG. 5, electrical contacts J28 and J29 may be coupled to the proximal end of insulated wire conductors 130a and 130b, respectively, of electrical cord 40. As shown in FIG. 12, the distal end of insulated wire conductors 130a, 130b may ultimately couple with the bipolar electrodes 180a, 180b of device 10 as discussed in greater detail below.

Figure 16:
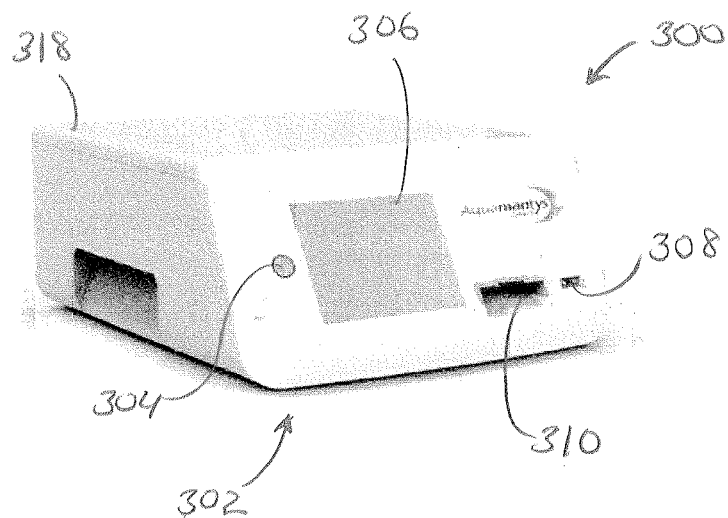
FIG. 16 is a perspective view of an electrosurgical unit according to one embodiment of the invention.
Figure 17:
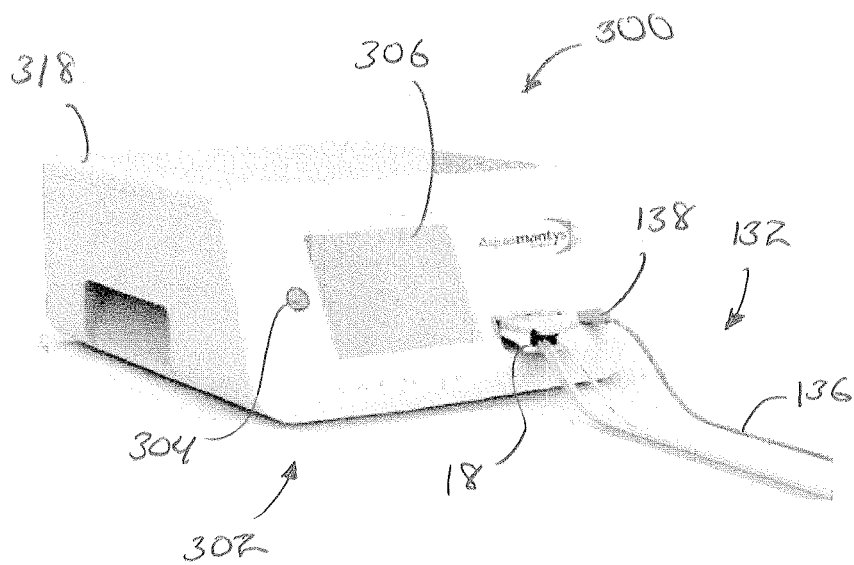
FIG. 17 is a perspective view of the electrosurgical unit with the cartridge member of the cartridge assembly installed.

Additionally, electrosurgical unit 300 may be operated in a monopolar mode with monopolar power provided through power output BP+, in which case power output BP− is no longer utilized. Rather, as shown in FIG. 12, an additional cord 132 may be utilized to connect a ground pad dispersive electrode 134, which is located on the patient, to the electrosurgical unit 300 using wire conductor 136 and plug 138 at the end thereof which connects to the ground pad receptacle 308 (as shown in FIGS. 16 and 17).

During monopolar operation, an electrode of device 10 is used in conjunction with ground pad dispersive electrode 134 which is placed on the patient (also known as a patient return electrode or neutral electrode), typically on the back or other suitable anatomical location. An electrical circuit may then be formed between the electrode of device 10 and ground pad dispersive electrode 134 with electrical current flowing from the device electrode through the patient to ground pad dispersive electrode 134 in a manner known in the art.

During bipolar operation, the ground pad electrode 134 located on the patient is not required, and a second electrode providing an electrical pole may be provided as part of device 10. An alternating current electrical circuit may then be created between the first and second electrical poles of the device. Consequently, alternating current no longer flows through the patient's body to the ground pad electrode 134, but rather through a localized portion of tissue between the poles of the bipolar electrodes. Monopolar and bipolar power may be provided from electrosurgical unit 300 in a manner known in the art.

Returning to FIG. 7, a control signal from electrosurgical unit 300 may be provided to electrical contact J14, which may be configured to receive a control signal from electrosurgical unit 300 as part of a control circuit configured to control bipolar power output. The control signal may then communicated along an electrically conductive pathway to electrical contact J23. As shown in FIG. 5, electrical contact J23 may be coupled to the proximal end of insulated wire conductor 142 of electrical cord 40. As shown in FIG. 12, the distal end of insulated wire conductor 142 may be coupled to a radio-frequency power hand-switch activation assembly 146 within hand-piece 12. Hand-switch assembly 146 may comprise push button 148 which overlies a domed switch on a platform comprising a printed circuit board, with the construction and wiring of the hand-switch assembly 146 known in the art. Upon depression of push button 148, the domed switch beneath push button 148 may form a closed circuit which enables the control signal, here comprising a relatively low voltage direct current, to return and be sensed by electrosurgical unit 300, generally via wire conductor 142, which then accordingly provides bipolar power. When the button 148 is released, the control circuit may open and the electrosurgical unit 300 may no longer receives the control signal to activate radio-frequency power. Consequently, the electrosurgical unit 300 may then deactivate the bipolar radio-frequency power output.

A control signal from electrosurgical unit 300 may be provided to electrical contact J15, which may be configured to receive a control signal from electrosurgical unit 300 as part of a control circuit configured to control monopolar power output. The control signal may then communicated along an electrically conductive pathway to electrical contact J24. While not shown in FIG. 5, electrical contact J24 may be coupled to the proximal end of insulated wire conductor 144 of electrical cord 40. As shown in FIG. 12, the distal end of insulated wire conductor 144 may be coupled to a radio-frequency power hand-switch activation assembly 152 within hand-piece 12. Hand-switch assembly 152 may comprise push button 154 which may overlie a domed switch on a platform comprising a printed circuit board, with the construction and wiring of the hand-switch assembly 152 known in the art. Upon depression of push button 154, the domed switch beneath push button 154 may form a closed circuit which enables the control signal, here comprising a relatively low voltage direct current, to return and be sensed by electrosurgical unit 300, generally via wire conductor 144, which then accordingly provides monopolar power. When the button 154 is released, the control circuit may open and the electrosurgical unit 300 may no longer receive the control signal to activate radio-frequency power. Consequently, the electrosurgical unit 300 may then deactivate the monopolar radio-frequency power output.

Exemplary hand switch assemblies may be found in U.S. Publication No. 2006/0149225, published Jul. 6, 2006, and U.S. Publication No. 2005/0090816, published Apr. 28, 2005, which are assigned to the assignee of the present invention and are hereby incorporated by reference in there entirety to the extent they are consistent.

Electrosurgical unit 300 may also be configured to receive a stream of serial data including certain operating parameters and other information from cartridge assembly 16, and more particularly cartridge member 18, concerning the set-up and/or operation of device 10. In particular, as shown in FIG. 5, cartridge member 18 may be configured to provide tissue treatment device information to the electrosurgical unit 300 from a tangible storage medium configured to store the tissue treatment device information. The tangible storage medium may be in the form of an electronic memory 26 (also shown at U1 in FIG. 7) located on printed circuit board 24, and more particularly an electrically erasable programmable read only memory (EEPROM) in which to store such operating parameters and other information.

For example, the tissue treatment device information provided with memory 26 may include a unique identifier (e.g. model number and serial number) and a fixed time period operable with a use of device 10 (e.g. 24 hours) from the time of first radio-frequency activation which is then stored by electrosurgical unit 300 for future reference. Memory 26 may included at least one operating parameter such as default settings operable with a use of device 10. For example, the tissue treatment device information may comprise at least one of a radio-frequency power delivery apparatus setting and a fluid delivery apparatus setting operable with a use of device 10, such as radio-frequency power level setting and fluid flow level setting for device 10.

Tissue treatment device information may also comprise a plurality of radio-frequency power delivery apparatus settings operable with a use of device 10 and at least one fluid delivery apparatus setting corresponding to each of the radio-frequency power delivery apparatus settings. For example, memory 26 may include settings for a range of radio-frequency power levels and fluid flow levels operable with a use of device 10, which extend from a minimum radio-frequency power level and minimum fluid flow level to a maximum radio-frequency power level and maximum fluid flow level for device 10. Memory 26 may also include operating parameters such as one or more relationships which relate fluid flow level to the radio-frequency power level over a range of fluid flow levels and radio-frequency power levels for device 10. As shown in FIG. 7, data may be received by electrosurgical unit 300 from memory 26 via electrical contacts J1 to J4.

Printed circuit board 24 also may include electrical contacts J12 and J13 which may be configured to detect moisture or wetness on printed circuit board 24. Contacts J12 and J13 may be configured to be part of a moisture monitoring circuit provided with a predetermined impedance. If the impedance between the contacts J12 and J13 decreases, such as may occur if fluid 502 where to form a bridge between the contacts thus electrically coupling the contacts, electrosurgical unit 300 may cease operation until the predetermined impedance value is attained.

Cartridge member 18, and in particular printed circuit board 24, also may include electrical contacts which are configured to receive power for additional features and accessories of device 10 including, for example a light, such as a light emitting diode (LED) or fiber optic light, to illuminate a tissue treatment site during a surgical procedure. The LED may require a relatively low power, such as a magnitude of 4-5 volts DC (direct current).

Cartridge member 18, and in particular printed circuit board 24 may also include electrical contacts which are configured to provide connection and transmit signals to a video recording source to record video, for example, of a tissue treatment site during a surgical procedure, which may be viewed by a video camera, such as a digital or fiber optic video camera, provided with device 10.

Having discussed the electrical and fluid communication of device 10 with electrosurgical unit 300 and fluid source 500, attention will now be directed to end effector of device 10. As previously discussed, the distal end of insulated wire conductors 130a, 130b may be coupled to a proximal portion of shafts 124a, 124b of shaft assembly 128 within hand-piece 12.

Figure 13:
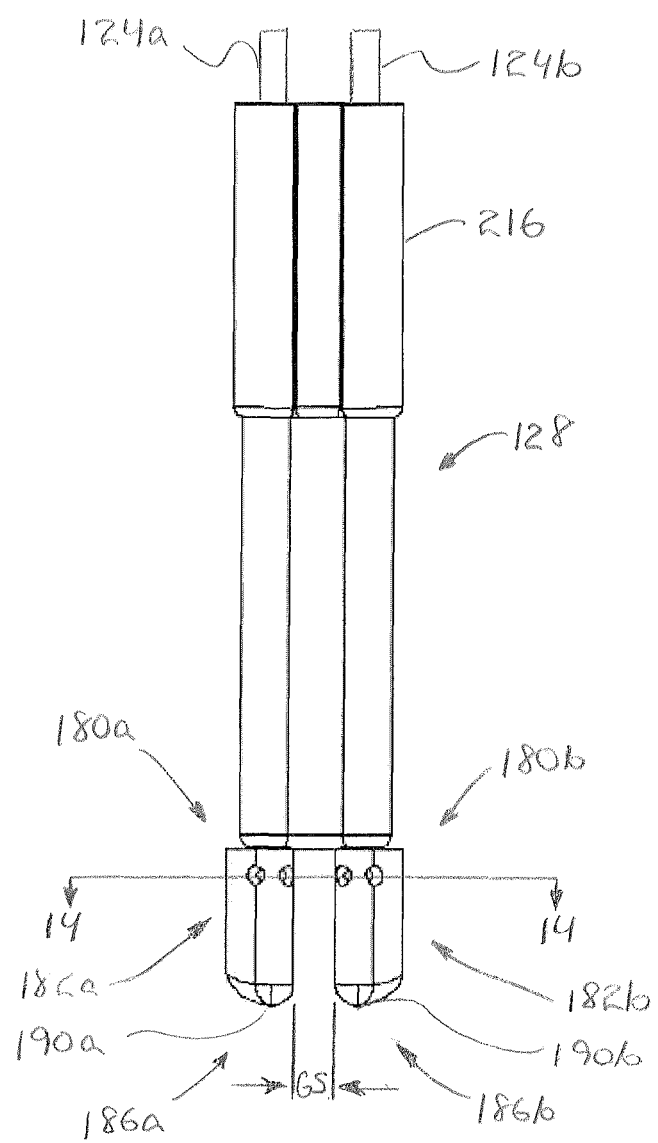
FIG. 13 is a close-up view of the shaft assembly of the device.

Now, referring to FIG. 13, shaft assembly 128 of device 10 may comprise two parallel, self-supporting, electrically conductive hollow shafts 124a, 124b, which comprise metal such as stainless steel tubing. Carried by and connected to the distal ends of shafts 124a, 124b may be two laterally and spatially separated (by empty space) contact elements comprising electrodes 180a, 180b which may be configured as minor images in size and shape, and have a blunt distal end with a surface devoid of edges (to provide a uniform current density) to treat tissue. In the present embodiment electrodes 180a, 180b may comprise an electrically conductive metal, such as stainless steel. Other suitable materials may include titanium, gold, silver and platinum.

In certain embodiments, one or both shafts 124a, 124b may be made of electrically non-conducting material except for the portion at the distal end that comes in contact with electrodes 180*a*, 180*b*. In these embodiment, an insulated wire conductor may extend and be joined to the electrically conducting portion of shaft 124*a*, 124*b*. In still other embodiments, shafts 124*a*, 124*b* may completely comprise electrically non-conducting material, in which case an insulated wire conductor would extend and be joined directly to electrodes 180*a*, 180*b*.

As shown in FIG. 13, each electrode 180*a*, 180*b* may comprise an elongated portion 182*a*, 182*b*. With respect to length, in the present embodiment, elongated portion 182*a*, 182*b* may have a length in the range between and including 2 mm to 6 mm, and more specifically have a length of 3 mm to 5 mm. With respect to spacing, in the present embodiment the spatial gap separation GS between electrodes 180*a*, 180*b* may be in the range between and including 0.1 mm to 4 mm, and more specifically 1 mm to 2.5 mm, and more specifically 1.5 mm to 2.3 mm.

Figure 14:
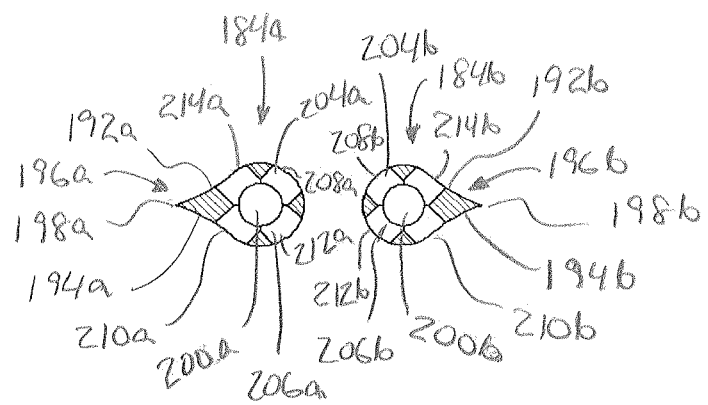
FIG. 14 is a close-up cross-sectional view of the electrodes of the device of FIG. 1 taken along line 14-14 of FIG. 13.

As best shown in FIG. 14, opposing concave sides 192*a*/194*a* of elongated portion 182*a*, and opposing concave sides 192*b*/194*b* of elongated portion 182*b* may converge laterally to provide a wedge shaped blade portion 196*a*, 196*b* which terminates in a lateral cutting edge 198*a*, 198*b* which extends longitudinally along a length of each electrode 180*a*, 180*b*. As shown in FIG. 13, lateral cutting edge 198*a*, 198*b* may transition smoothly onto the distal end of each electrode 180*a*, 180*b* and forms a portion of the distal end of each electrode 180*a*, 180*b*.

Lateral cutting edge 198*a*, 198*b* may be configured to cut tissue electrosurgically in the presence of monopolar radio frequency energy from electrosurgical unit 300, without any fluid 502 being provided from fluid source 500. However, in other embodiments, lateral cutting edge 198*a*, 198*b* may be configured to cut tissue with fluid 502 being provided simultaneously from device 10, or be configured to cut tissue mechanically without electrosurgical energy. Furthermore, while two cutting edges 198*a*, 1988*b* are shown, only one of the edges 198*a* or 198*b* may be configured to cut tissue electrosurgically or mechanically. In such instance, the blade portion of one electrode may be eliminated and the elongated portion may be completely cylindrical.

As shown in FIG. 13, electrodes 180*a*, 180*b* and elongated portions 182*a*, 182*b* may terminate in distal end portion 186*a*, 186*b*. The distal end portion 186*a*, 186*b* of electrodes 180*a*, 180*b* may be configured to move and slide with painting action across a tissue surface in the presence of bipolar radio frequency energy from electrosurgical unit 300 and fluid 502 from the fluid source 500. As shown, the distal end portion 186*a*, 186*b* of each electrode 180*a*, 180*b* has a blunt, rounded shape which provides a smooth contour surface. More specifically, as shown, distal end portion 186*a*, 186*b* of each electrode 180*a*, 180*b* may comprise a spherical portion 190*a*, 190*b*. In the present embodiment, spherical portion 190*a*, 190*b* may have a radius in the range between and including 0.5 mm to 1.5 mm, and more specifically 0.75 mm to 1.15 mm.

Figure 15:
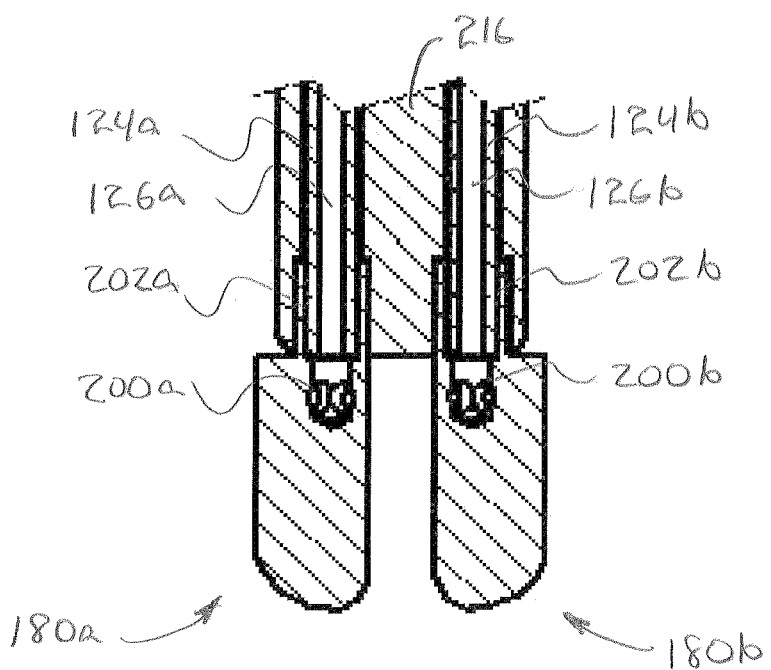
FIG. 15 is a close-up cross-sectional view of a distal end portion of the device of FIG. 1 taken perpendicular to line 14-14 of FIG. 13.

As best shown in FIGS. 14 and 15, within a cylindrical portion 184*a*, 184*b* of each electrode 180*a*, 180*b* proximal to distal end portion 186*a*, 186*b*, each electrode 180*a*, 180*b* may include a longitudinally oriented linear blind bore 200*a*, 200*b* and counter bore 202*a*, 202*b*. As shown in FIG. 15, the outside diameter of a distal end portion of each shaft 124*a*, 124*b* may be configured to extend into counter bore 202*a*, 202*b* of electrodes 180*a*, 180*b* and fit with the diameter of counter bore 202*a*, 202*b*, with the distal end of each shaft 124*a*, 124*b* in contact with the bottom of the counter bore. The electrodes 180*a*, 180*b* and shafts 124*a*, 124*b* may then be welded together. In alternative embodiments, the outside diameter of shafts 124*a*, 124*b* may be configured to fit with the diameter of counter bore 202*a*, 202*b* to form a press (interference) fit to provide a secure connection. In other alternative embodiments, electrodes 180*a*, 180*b* may be assembled to shafts 124*a*, 124*b* by threaded engagement. In still other embodiments, electrodes 180*a*, 180*b* may be detachably assembled to shafts 124*a*, 124*b* such that they may be removed from the shafts 124*a*, 124*b*, particularly manually by human hand.

In addition to blind bore 200*a*, 200*b* and counterbore 202*a*, 202*b*, as shown in FIG. 14, electrodes 180*a*, 180*b* may also include a through bores 204*a*/206*a* and 204*b*/206*b* which perpendicularly intersects bore 200*a*, 200*b* and perpendicularly intersect one another to provide outlets 208*a*/210*a*/212*a*/214*a* and 208*b*/210*b*/212*b*/214*b* for fluid 502. Thus, after fluid 502 flows through the lumens 126*a*, 126*b* of shafts 124*a*, 124*b*, fluid 502 then flows through into the tubular passage provided by blind bore 200*a*, 200*b* and then into the tubular passage provided by through bores 204*a*/206*a* and 204*b*/206*b* where it thereafter exits device 10 from fluid outlets 208*a*/210*a*/212*a*/214*a* and 208*b*/210*b*/212*b*/214*b*, which are all proximal to distal end portion 186*a*, 186*b* of electrodes 180*a*, 180*b*. As shown in FIG. 14, fluid outlets 208*a*/212*a* and 208*b*/212*b* may be defined by the cylindrical portion 184*a*, 184*b* of electrodes 180*a*, 180*b*, while fluid outlets 210*a*/1214*a* and 210*b*/214*b* may be defined by sides of 192*a*/194*a* and 192*b*/194*b* of blade portion 196*a*, 196*b* and adjacent cutting edge 198*a*, 198*b*.

As best shown in FIGS. 13 and 15, a portion of the lengths of shafts 124*a*, 124*b* may be surrounded by and encapsulated in a common outer member 216, which may comprise a flexible plastic material. Outer member 216 may electrically insulate the exposed length of shafts 124*a*, 124*b*.

Outer member 216 may be formed by injection molding. During the injection molding process, a sub-assembly comprising electrodes 180*a*, 180*b* and shafts 124*a*, 124*b* may be placed in an injection mold prior to the introduction of the plastic material. Thereafter, the mold may be closed and a thermoplastic may be injected into the unoccupied portions of the mold cavity to overmold and mold-in place portions of the sub-assembly as shown in FIG. 13. During the injection molding process, retainer clips (not shown) may provide the benefit of retaining shafts 124*a*, 124*b* in position relative to each other to better ensure that the shafts 124*a*, 124*b* are centrally located within the polymer molding.

To be hand shapeable by surgeons and other users of device 10, so that the device 10 may be used in a greater multitude of angles and locations, at least a portion of shafts 124*a*, 124*b* of device 10 may be malleable to provide a malleable shaft assembly 128. Also, in this manner, a distal portion of shafts 124*a*, 124*b* may be bendable at an angle relative to the longitudinal axis of the proximal portion of shafts 124*a*, 124*b* during manufacturing of device 10 so they may be provided to users of device 10 at various angles. For example, angle may range from 5 degrees to 90 degrees, and more particularly, 15 degrees to 45 degrees, and even more particularly 30 degrees. As used herein, malleable means able to be shaped, particularly by bending (without a mechanical mechanism, such as a hinge or joint). It should be understood that shaft assembly 128 may independently maintain the shape associated with the selected bent shape, and does not require additional components (e.g., pull wires, etc.) to maintain the selected bent shape. Furthermore, shaft assembly 128 may maintain the selected shape such that when device 10 is used to treat tissue, and will not overtly deflect from the selected shape. Furthermore, shaft assembly 128 may be constructed such that a user can readily re-shape the shafts back to a straight state and/or other desired bent configurations.

Outer member 216, in addition to electrically insulating shafts 124a, 124b from one another, has been found to be particularly useful in facilitating the hand shaping of shafts 124a, 124b of shaft assembly 128 simultaneously and with a similar contour without cracking and maintaining the tip spacing. In this manner, surgeons and other users of device 10 need not bend the shafts 124a, 124b individually.

To provide malleability, shafts 124a, 124b may have an outer wall diameter of 0.063 inches and an inner wall diameter of 0.032 inches. Shafts 124a, 124b also are particularly made from 304 stainless steel with a temper from ½ to ¾ hard, 130,000 to 150,000 psi. (pounds per square inch) tensile strength) and an elongation at break of 40%. Shafts 124a, 124b with the foregoing properties provide sufficient stiffness as not to be too pliable during normal use of device 10, while at the same time inhibiting the shafts 124a, 124b from kinking or breaking when shaped for application. When the wall thickness may be too thin, shafts 124a, 124b may kink, and when the wall thickness may be too thick, the shafts 124a, 124b may be too stiff. Furthermore, a shaft 124a, 124bb with a larger diameter may also kink more than a shaft of smaller diameter. Shafts 124a, 124b may also be malleable for a portion of the length or full length depending on application. For example, the shafts 124a, 124b can be made with variable stiffness along the length and be malleable only for a distal portion thereof. This may be performed by controlled annealing of the shafts 124a, 124b only in the area where malleability may be desired.

Having discussed device 10 in detail, attention will now be directed to electrosurgical unit 300 shown starting at FIG. 16. As shown in FIGS. 16-17, electrosurgical unit 300 may include a front control panel 302. Front control panel 302 may include a power (on/off) switch 304 and touchscreen graphical user interface (GUI) 306. Front panel 302 also may include a ground pad receptacle 308 as well as a cartridge receptacle 310 configured to receive cartridge member 18 of cartridge assembly 16, which is shown installed in FIG. 17.

Figure 18:
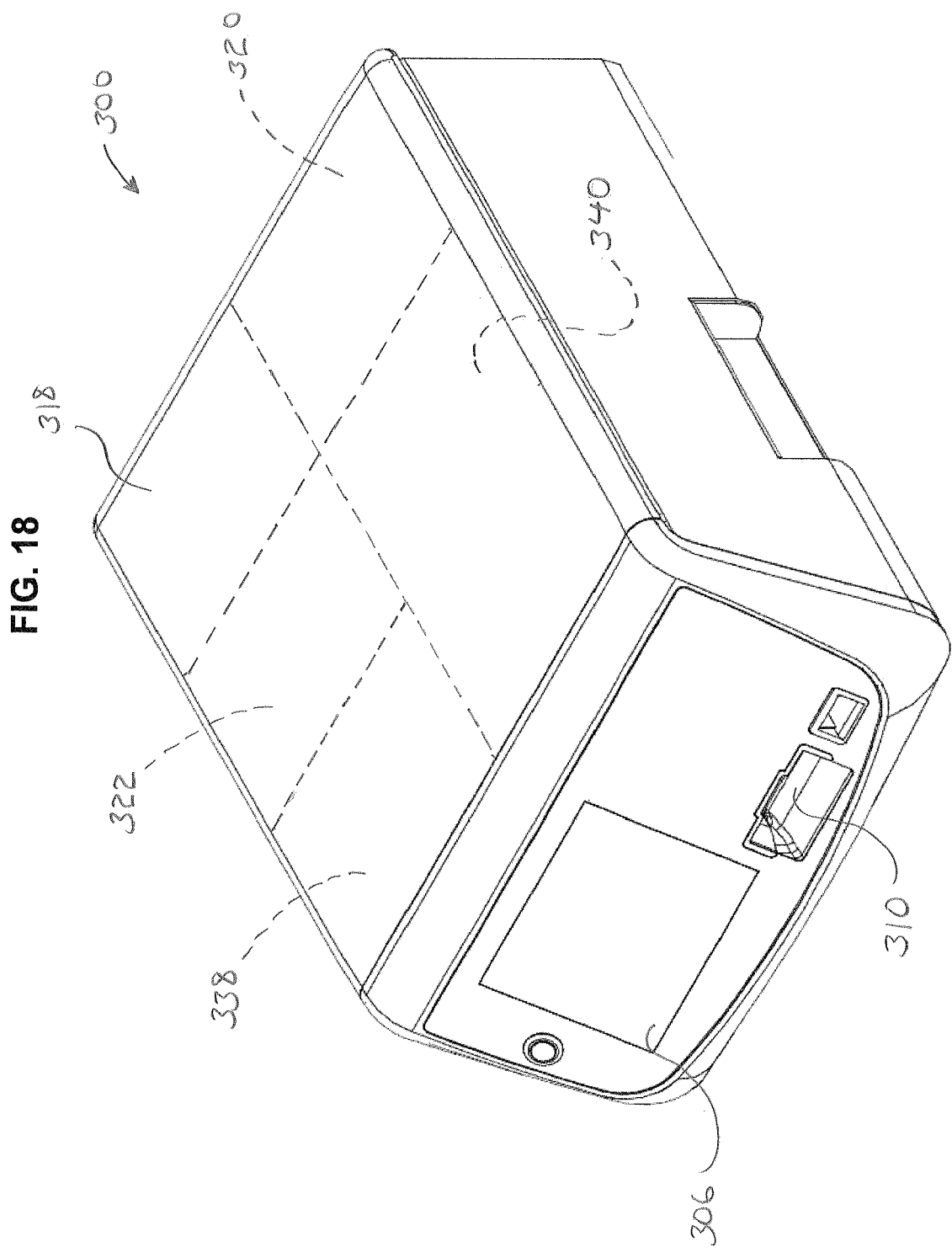
FIG. 18 is a perspective view of the electrosurgical unit.

As shown in FIG. 18, electrosurgical unit 300 may include an AC power supply 320, radio-frequency power source/generator 322, controller 338, including a central processing unit (CPU) and memory, and cartridge docking assembly 340 all interconnected and designed to communicate and function as an electrosurgical unit which provides radio-frequency power in a manner known in the art.

Figure 19:
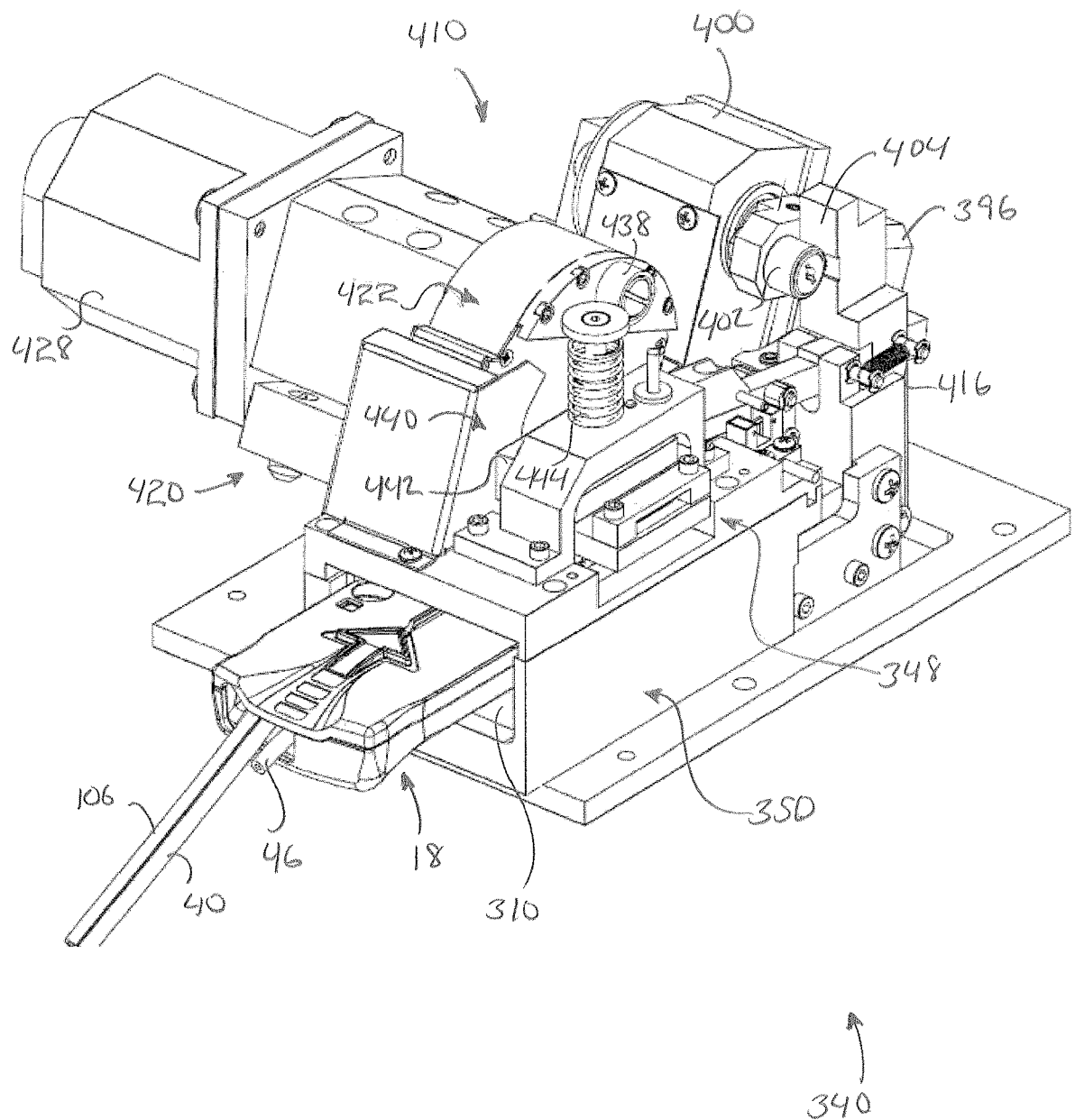
FIG. 19 is a front perspective view of the electrosurgical unit's docking assembly with a movable docking mechanism in the up (non-use) position prior to the docking mechanism engaging with the cartridge member.
Figure 20:
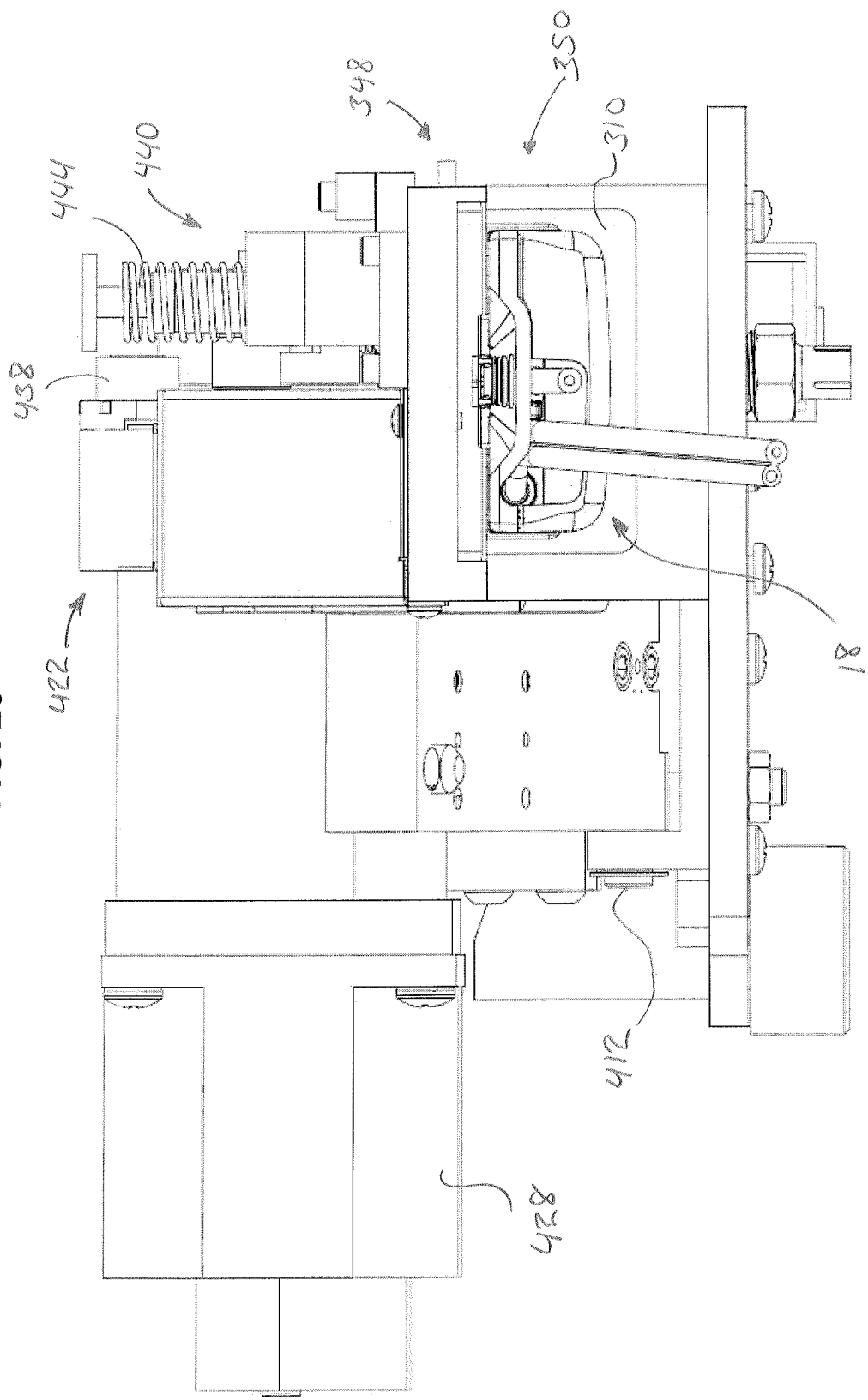
FIG. 20 is a front view of the docking assembly with the docking mechanism in the up position.
Figure 21:
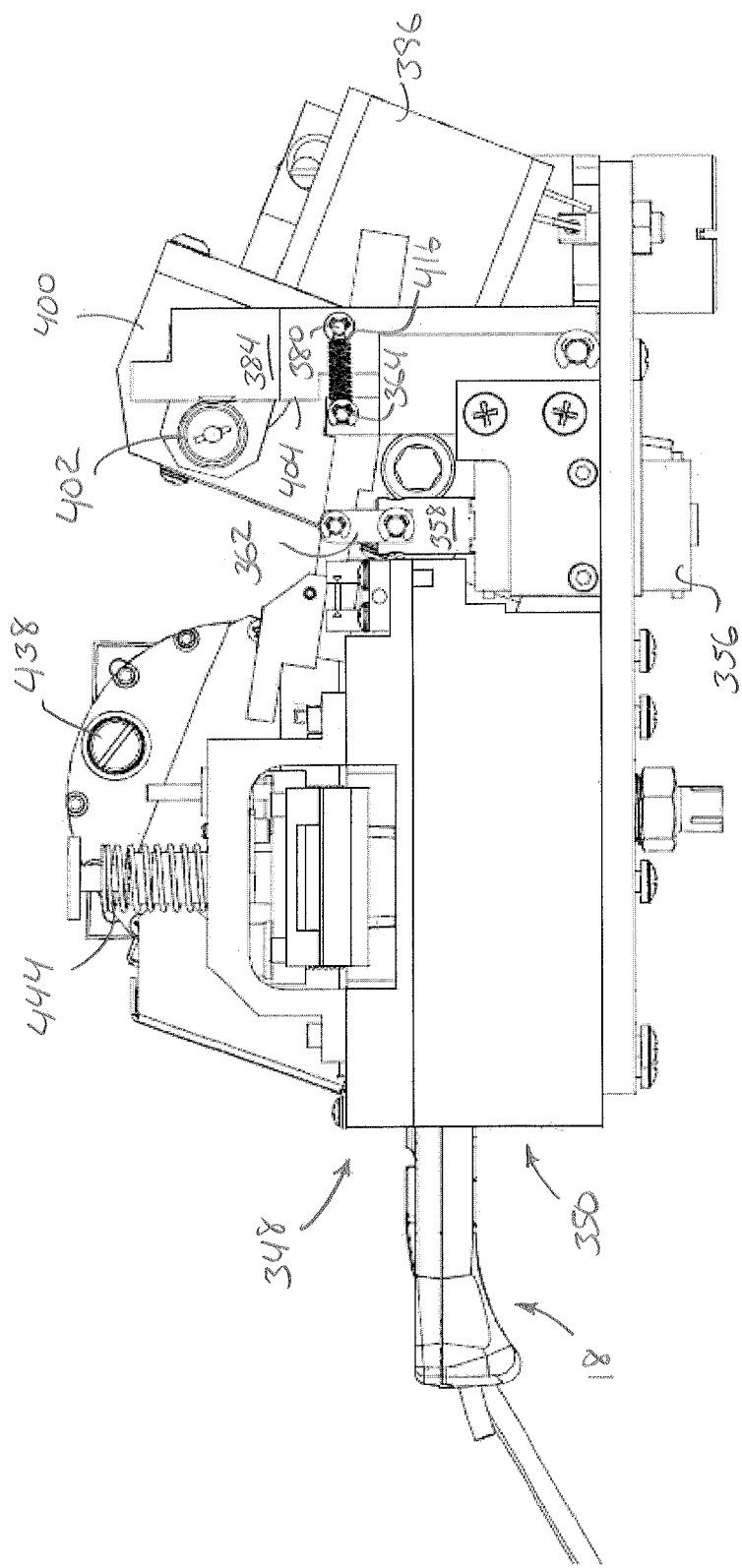
FIG. 21 is a right side view of the docking assembly with the docking mechanism in the up position.
Figure 22:
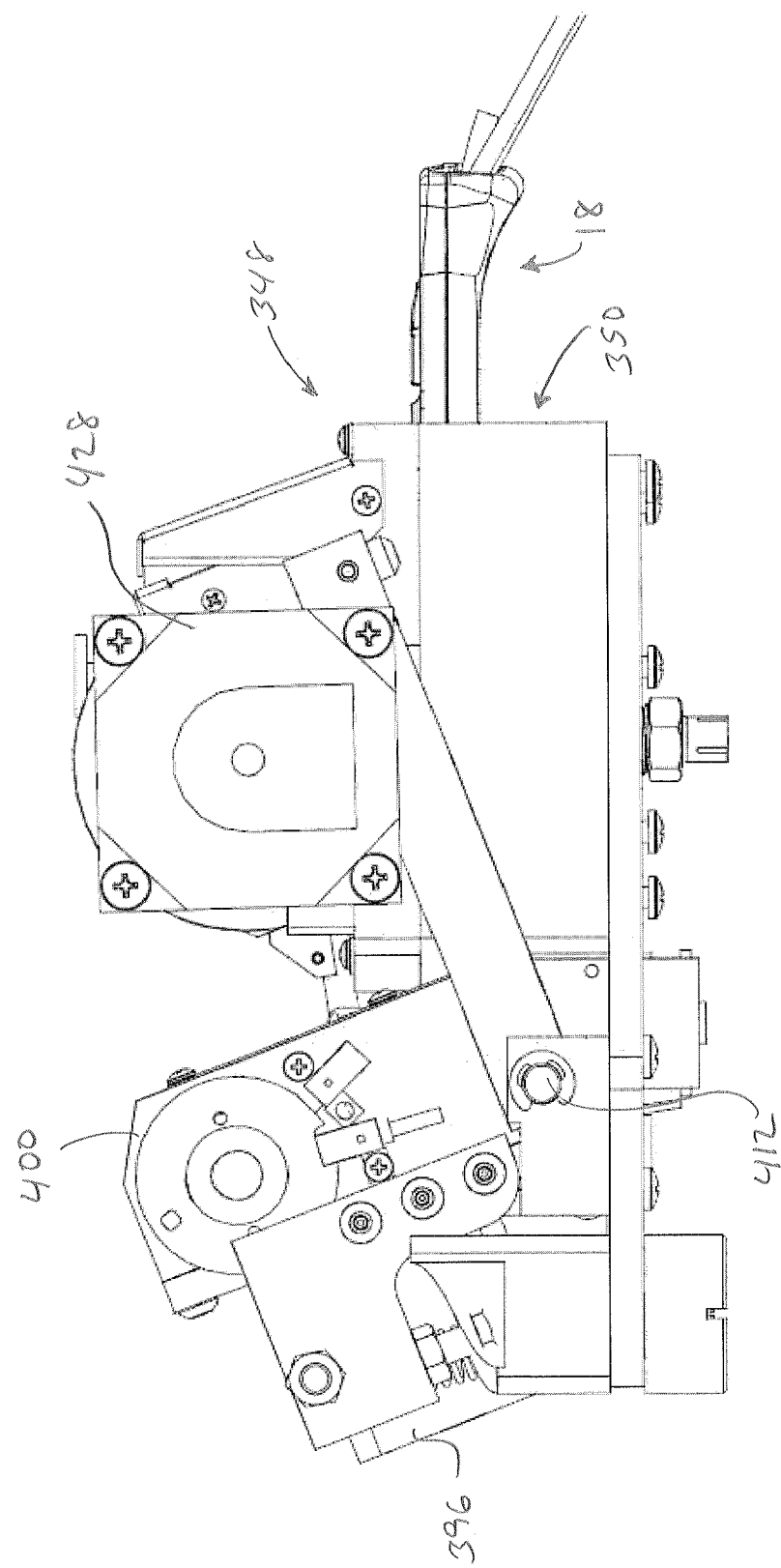
FIG. 22 is a left side view of the docking assembly with the docking mechanism in the up position.
Figure 23:
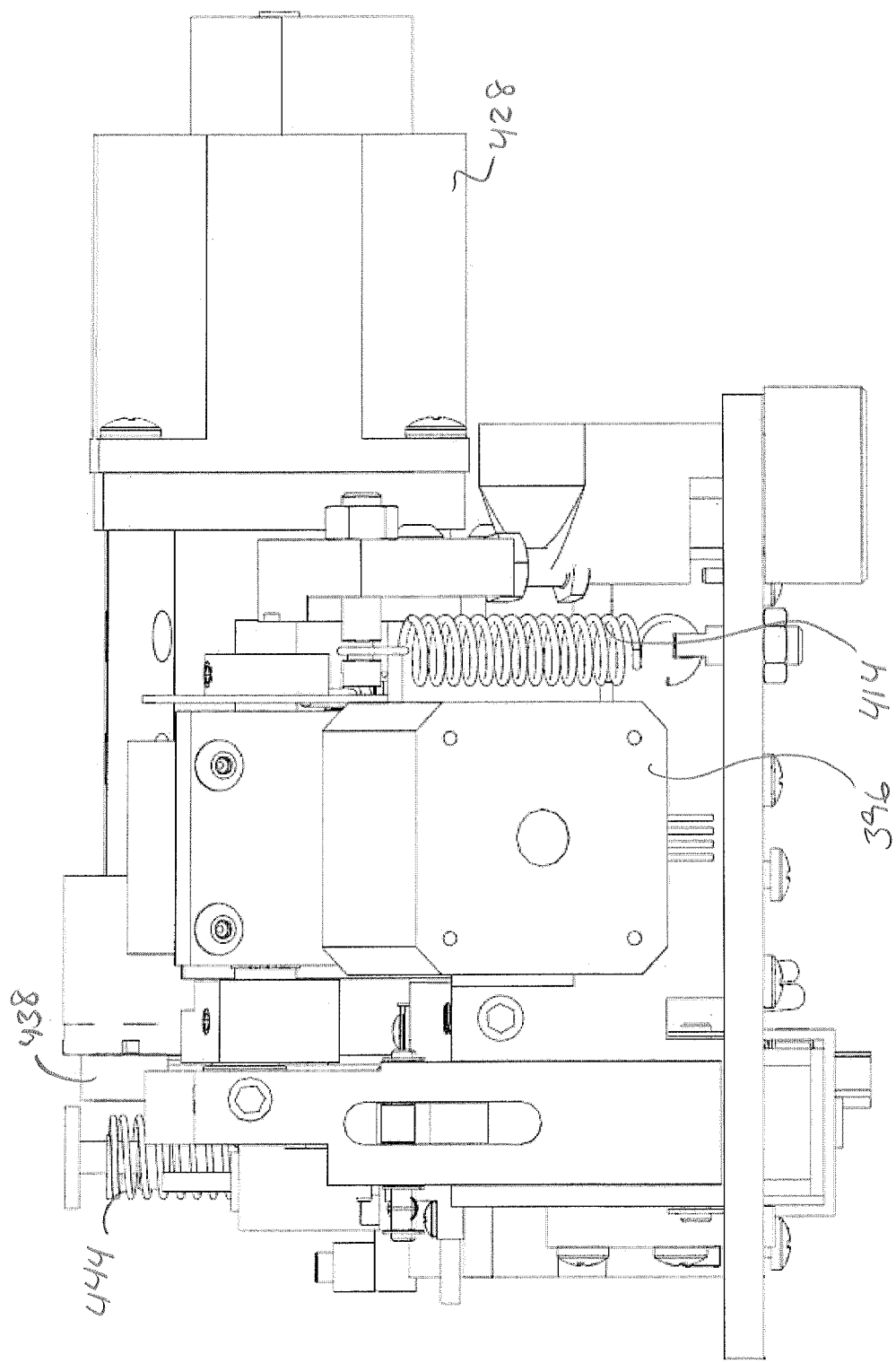
FIG. 23 is a rear view of the docking assembly with the docking mechanism in the up position.
Figure 24:
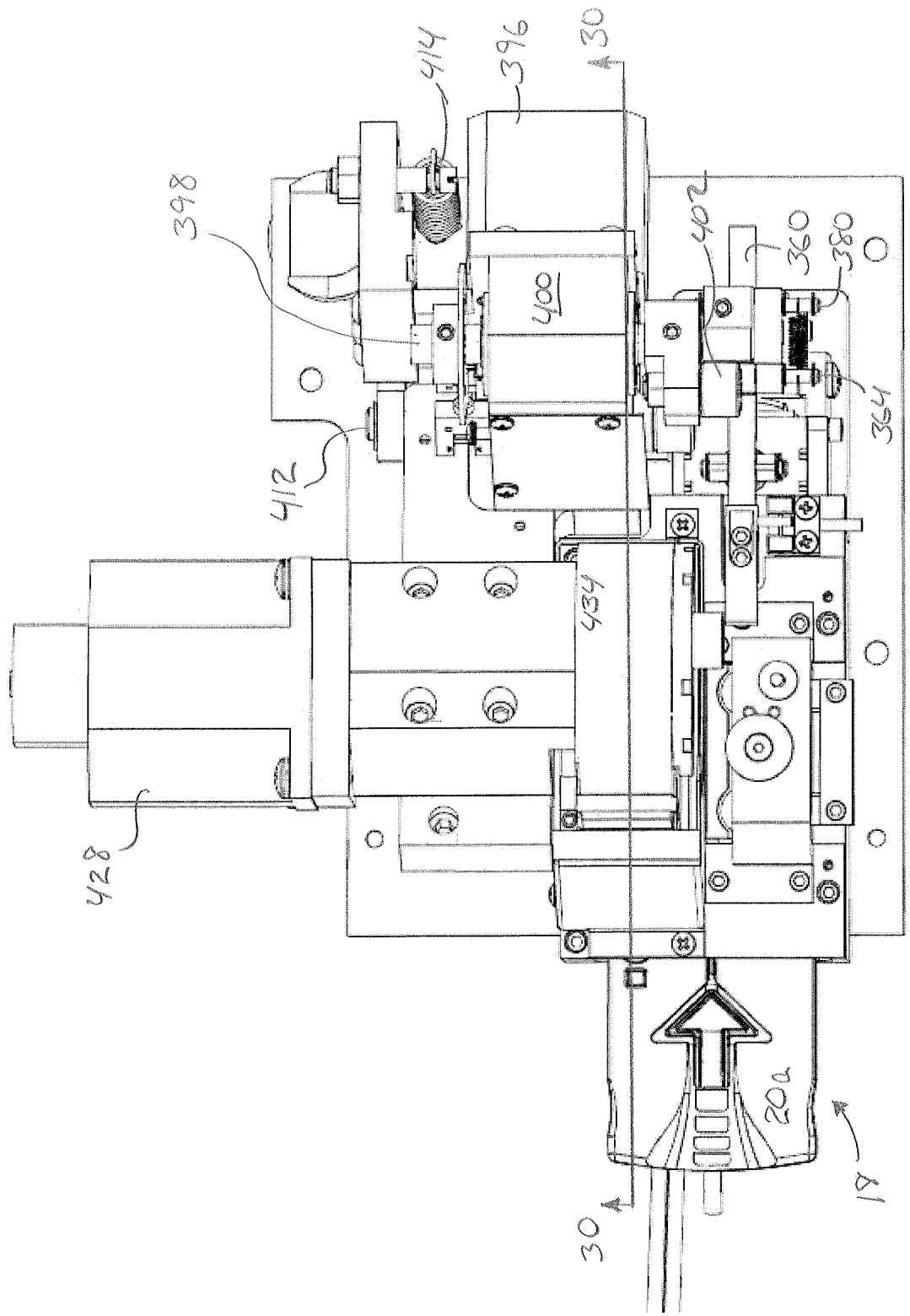
FIG. 24 is a top view of the docking assembly with the docking mechanism in the up position.

As shown in FIG. 19, electrosurgical unit 300 may include a docking assembly 340 with cartridge member 18 placed between upper receptacle enclosure 348 and lower receptacle enclosure 350. Front, right side, left side, rear and top views of the docking assembly 340 with a moveable docking mechanism 410 in the up (non-use) position prior to engaging with cartridge member 18 are shown in FIGS. 20-24, respectively. Operation of the docking assembly 340 will now be discussed in greater detail, with FIGS. 20-24 presented as needed.

Figure 25:
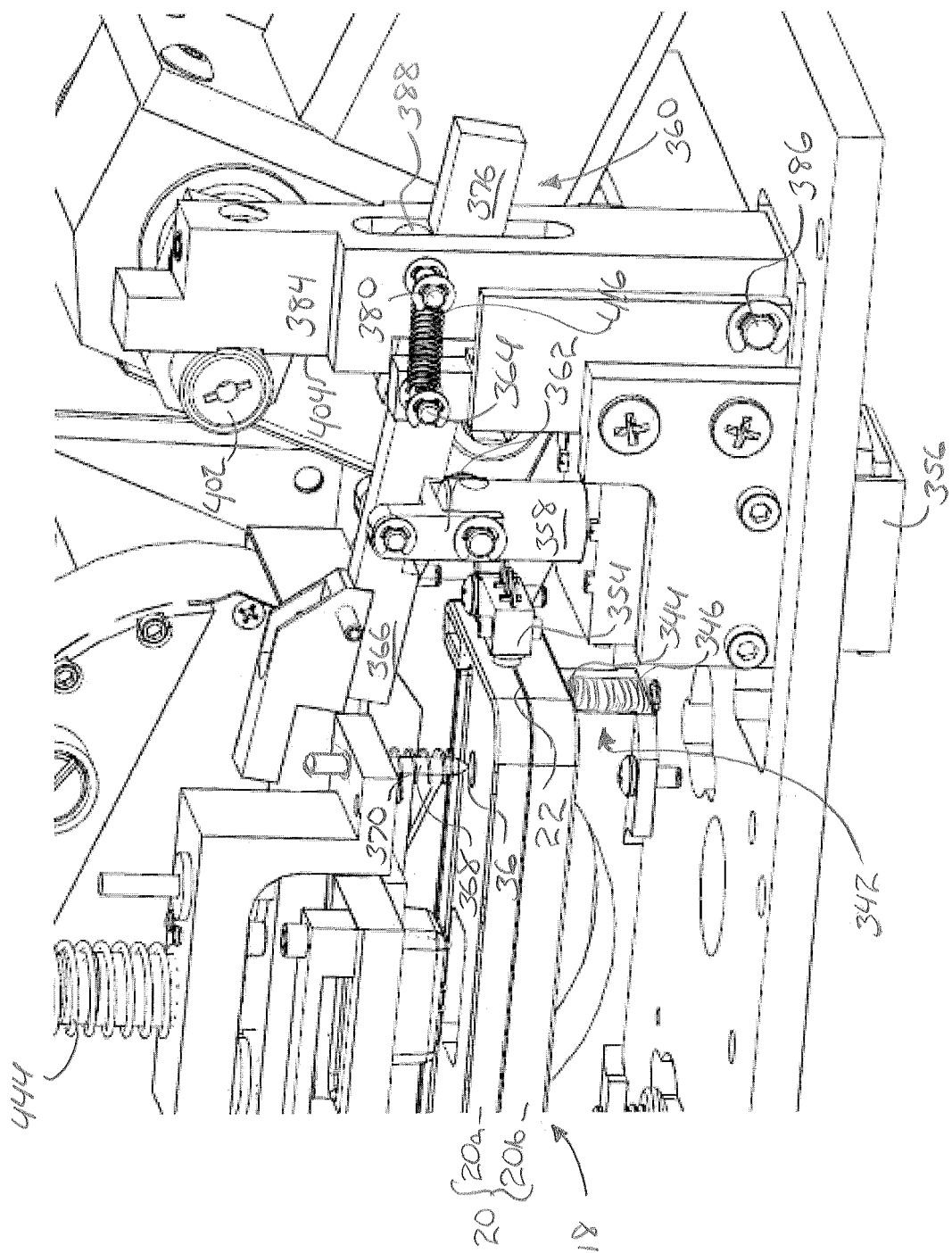
FIG. 25 is a rear perspective view of the docking assembly with the docking mechanism in the up position.

Referring to FIG. 25, upper receptacle enclosure 348 and lower receptacle enclosure 350 have been hidden to better show the operation of docking assembly 340. As shown in FIG. 25, near the end of insertion of cartridge member 18, the distal end 22 of cartridge member 18 may first interact with engagement mechanism 342, which is to inhibit the cartridge member 18 from inadvertently sliding out of receptacle 310 and separating from electrosurgical unit 300, as well as releaseably engage the cartridge member 18 when sufficient removal force may be applied to the engagement mechanism 342 to disengaged the cartridge member 18 and retract it from receptacle 310.

As shown, the engagement mechanism 342 may comprise a spring loaded ball 344 which may enter a detent 34 (shown in FIG. 3) which may be provided as part of the lower cartridge enclosure 350 (not shown). Engagement mechanism 342 may act to hold the cartridge member 18 in a temporary fixed use position relative to the electrosurgical unit 300. As the cartridge member 18 is inserted into receptacle 342, the lower surface of cartridge body 20b slides over the spring loaded ball 344 with a sufficient insertion force to overcome the bias/compression force of the spring 346 and retract the ball 344. As the cartridge member 18 thereafter reaches its use position, the ball 344 may enter a detent 34 formed in cartridge body 20b (shown in FIG. 3) which, under the force of compressed spring 346, now acts to hold the cartridge member 18 and electrosurgical unit 300 at their relative positions. Furthermore, the engagement mechanism 342 may provide the user with tactile feedback that the cartridge member 18 has been properly received by electrosurgical unit 300. Alternately, after ejection may be selected and a removal force is applied to cartridge member 18 sufficient to overcome the retention force applied by the spring 346, the spring 346 may again be compressed and the ball 344 removed from the detent 34 to facilitate removal of the cartridge member 18 from the electrosurgical unit 300.

In the foregoing manner, the cartridge assembly 16, and particularly the cartridge member 18, may be configured to engage with and configured to disengage from the electrosurgical unit 300. Furthermore, the cartridge assembly, and particularly the cartridge member 18 may be configured to engage with a releasable mechanical engagement mechanism (i.e. engagement mechanism 342) of the electrosurgical unit 300. Moreover, the cartridge assembly 16, and particularly the cartridge member 18, may be configured to engage the electrosurgical unit 300 with an interference fit. In other words, a fit made between, for example, the size or shape of two parts such that force is required for assembly or disassembly.

Also in the foregoing manner, the docking assembly 340 is configured to engage with and configured to disengage from the cartridge assembly 16. Furthermore, the docking assembly is configured to engage the cartridge assembly 16 with an interference fit.

As the ball 344 enters detent 34, the distal end 22 of cartridge member 18 may now make contact with a two position contact switch 354 which, when cartridge member 18 is absent, is in the open position. As cartridge member 18 is more fully inserted into cartridge receptacle 310 with an insertion force sufficient to close switch 354, an electrical circuit in the electrosurgical unit 300 may be closed which provides a signal to a controller 338 within electrosurgical unit 300 that a cartridge member 18 has been fully inserted into cartridge receptacle 310. Upon receipt of the signal that a cartridge member 18 has been fully inserted into the cartridge receptacle 310, electrosurgical unit 300 may now energize a solenoid 356.

Figure 26:
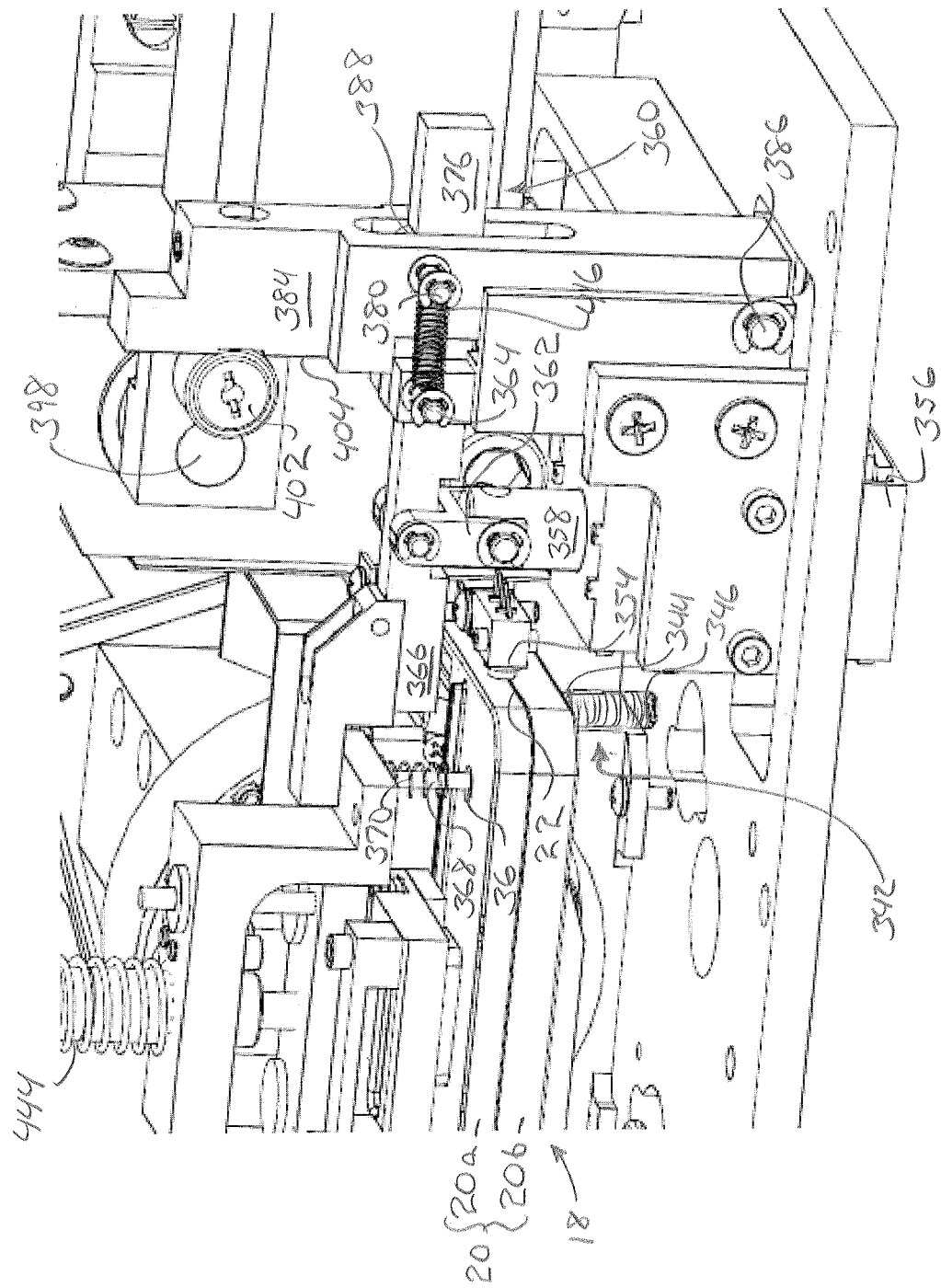
FIG. 26 is a rear perspective view of the docking assembly with the docking mechanism in the down (use) position.

Referring now to FIG. 25 and FIG. 26, solenoid 356 may retract armature 358, which may be coupled to lever 360 by pull bar 362. Consequently, upon retraction of armature 358, lever 360 may be rotated about pivot 364 and lever portion 366 rotates downward from its non-use (unengaged) position, as shown in FIG. 25, to its use (engaged) position, as shown in FIG. 26. As lever portion 366 rotates downward, pin 368 may enter cylindrical cavity 36 formed in cartridge body 20a. Pin 368 may performs multiple functions. First, pin 368 provides a locking mechanism to prevent inadvertent removal or dislodging of cartridge member 18 while electrosurgical unit 300 is ready for operation. Pin 368 may also provides a releasable locating/positioning mechanism to further position cartridge member 18 relative to electrosurgical unit 300 in addition to engagement mechanism 342.

Lever 360 may be pulled downward to its use (engaged) position with sufficient force to overcome the bias/compression force of spring 370, which thereafter returns lever 360 to its non-use position when power is removed from solenoid 356 and armature 358 is free to extend.

Figure 28:
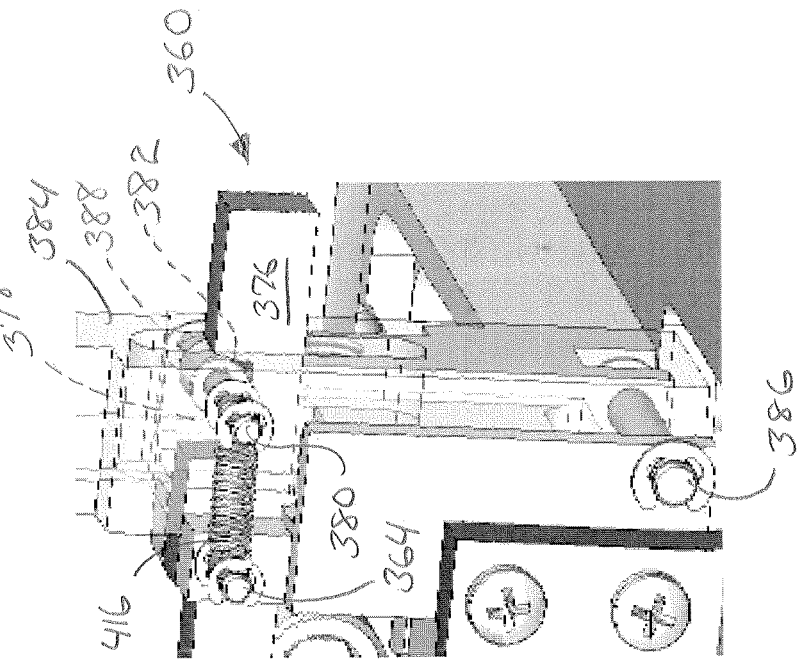
FIG. 28 is rear perspective view of the locking mechanism of with the docking mechanism in the down position.
Figure 27:
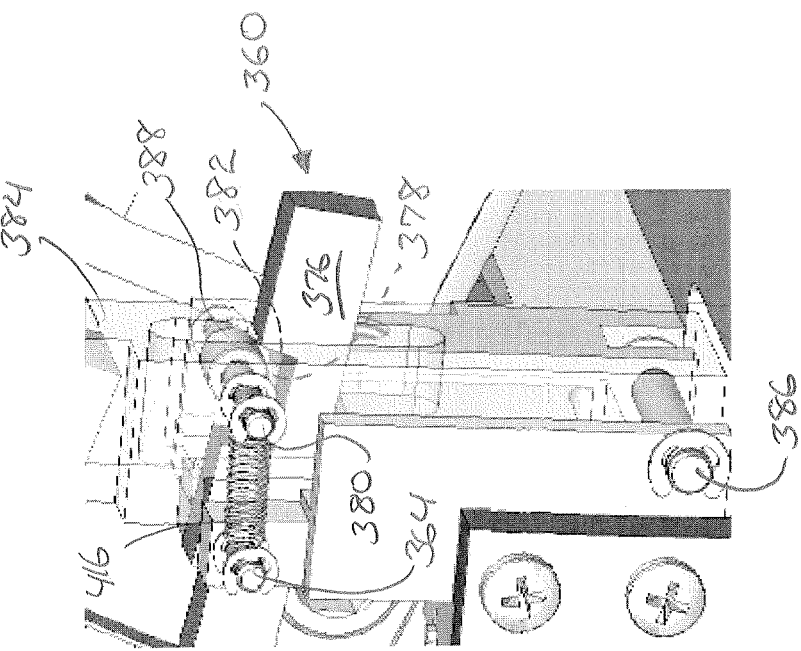
FIG. 27 is a rear perspective view of a locking mechanism with the docking mechanism in the up position.

As lever 360 is rotated about pivot 364, lever portion 376, which is opposite lever portion 366, may rotate upward about pivot 364. As shown in FIG. 27 and FIG. 28, lever portion 376 includes a catch 378 in the form of a notch into which locking pin 380 with roller 388 may enter and be captured as a result of the rotation of lever 360.

As a result of pin 380 and roller 388 entering catch 378 as shown in FIG. 28, lever 384 (shown in phantom in FIGS. 27 and 28), which rotates about pivot 386, may only travel rearward based on the length of catch 378. In other words, once pin roller 388 makes contact with the rearward surface 382 of catch 378, lever 384 may now be prevented from further rearward travel relative to lever 360 due to roller 388 contacting lever 384.

Returning to FIG. 26, once lever 360 is in its use position, an optical sensor may then provide a signal to a controller within the electrosurgical unit 300 that lever 360 is in such position. Upon receipt of the signal that lever 360 is now in its use position, electrosurgical unit 300 may now activate electric motor 396 which turns shaft 398 via a gearbox 400. Shaft 398 may provide an axle for cam 402 which, as a result of the rotation of shaft 398, contacts surface 404 of lever 384.

Upon rotation of cam 402 against surface 404 of lever 384, lever 384 may travel rearward until roller 388 makes contact with the rearward surface 382 of catch 378. As the position of lever 384 may now be fixed against moving rearwards by roller 388 fixated on contacting lever 384, surface 404 now provides a fixed load bearing surface against cam 402. As a result, upon further rotation of cam 402 against surface 404, movable docking mechanism 410 may rotates downward and moves radially about pivot 412 (shown in FIG. 22) against the bias/tension force of spring 414 (shown in FIG. 23) until it reaches its use position as sensed by an optical sensor. Docking mechanism 410 is now in its use (engaged) position. In other words, ready to deliver radio-frequency power and fluid as designed. After use of electrosurgical unit 300 is complete, a user may eject cartridge member 18 from unit 300 by selecting such control on unit 300, and the reverse of the docking procedure may be performed.

Should power be removed from solenoid 356 while docking mechanism 410 is in its use position, for instance if unit 300 is unplugged, electrosurgical unit 300 may be configured to return docking mechanism 410 upward to its non-use position and allow cartridge member 18 to be removed. As indicated above, when power is removed from solenoid 356, armature 358 may be free to extend and lever portion 366 of lever 360 rotates upward about pivot 364 due to the force of spring 370 to remove pin 368 from cylindrical cavity 36 formed in cartridge body 20a. Simultaneously, lever portion 376 of lever 360 may rotate downward about pivot 364 to disengage locking pin 380 with roller 388 from catch 378. Upon the disengaging of locking pin 380 and roller 388 from catch 378, lever 384 may now be free to move rearward about pivot 386. The force of spring 414 may then overcomes the force of spring 416 and move lever 384 rearward, releasing cam 402 from acting on surface 404. As cam 402 releases from surface 404, docking mechanism 410 may be rotated upwards about pivot 412 due to the force of spring 414. As docking mechanism 410 returns to its non-use position, and cam 402 rotates back to the not in use position, lever 384 moves forward about pivot 386 due to the force of spring 416. In this manner, locking pin 380 and roller 388 may now be positioned to be received by catch 378.

Figure 29:
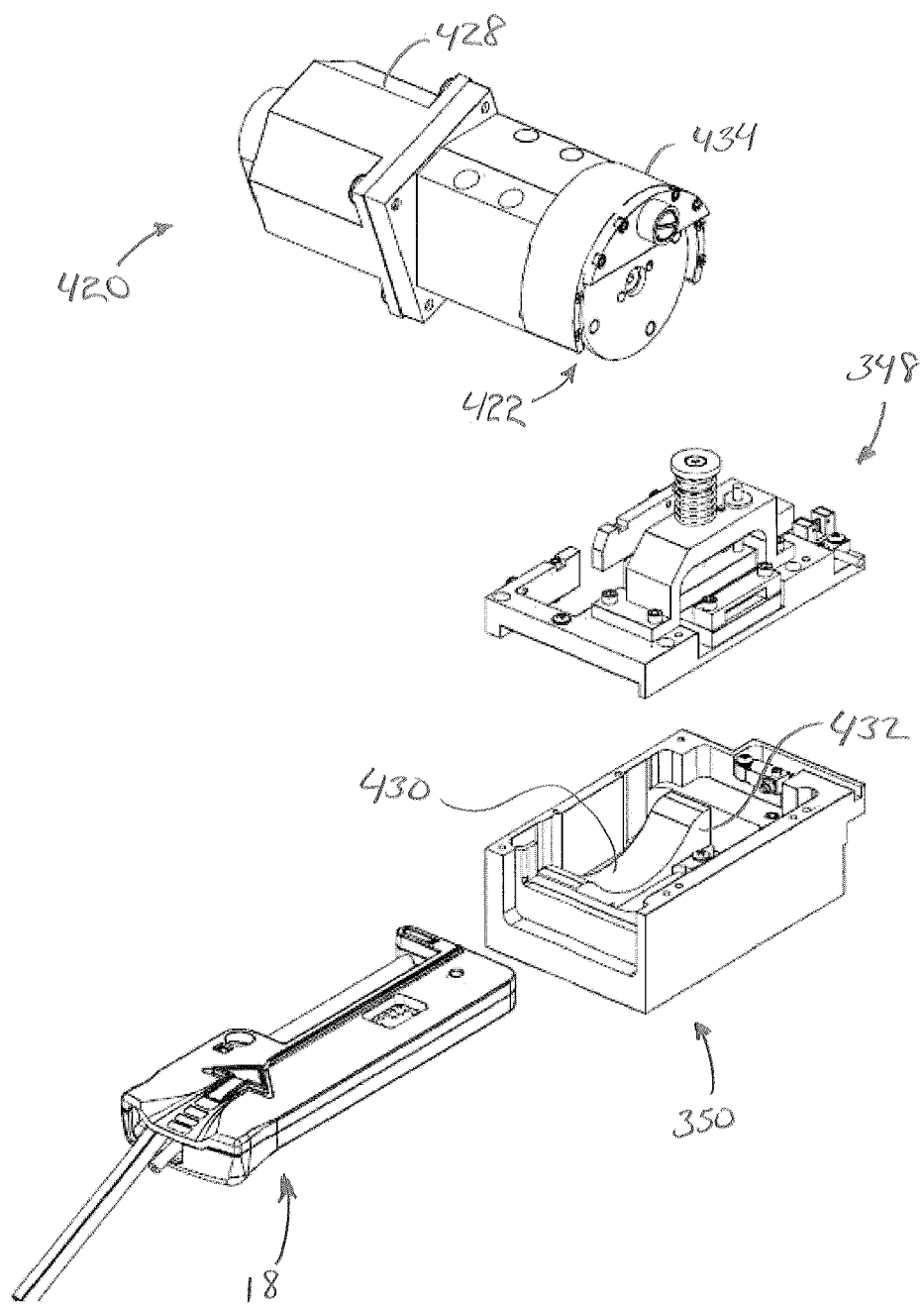
FIG. 29 is an exploded view of the cartridge member, upper receptacle enclosure, lower receptacle enclosure and a fluid delivery apparatus.
Figure 30:
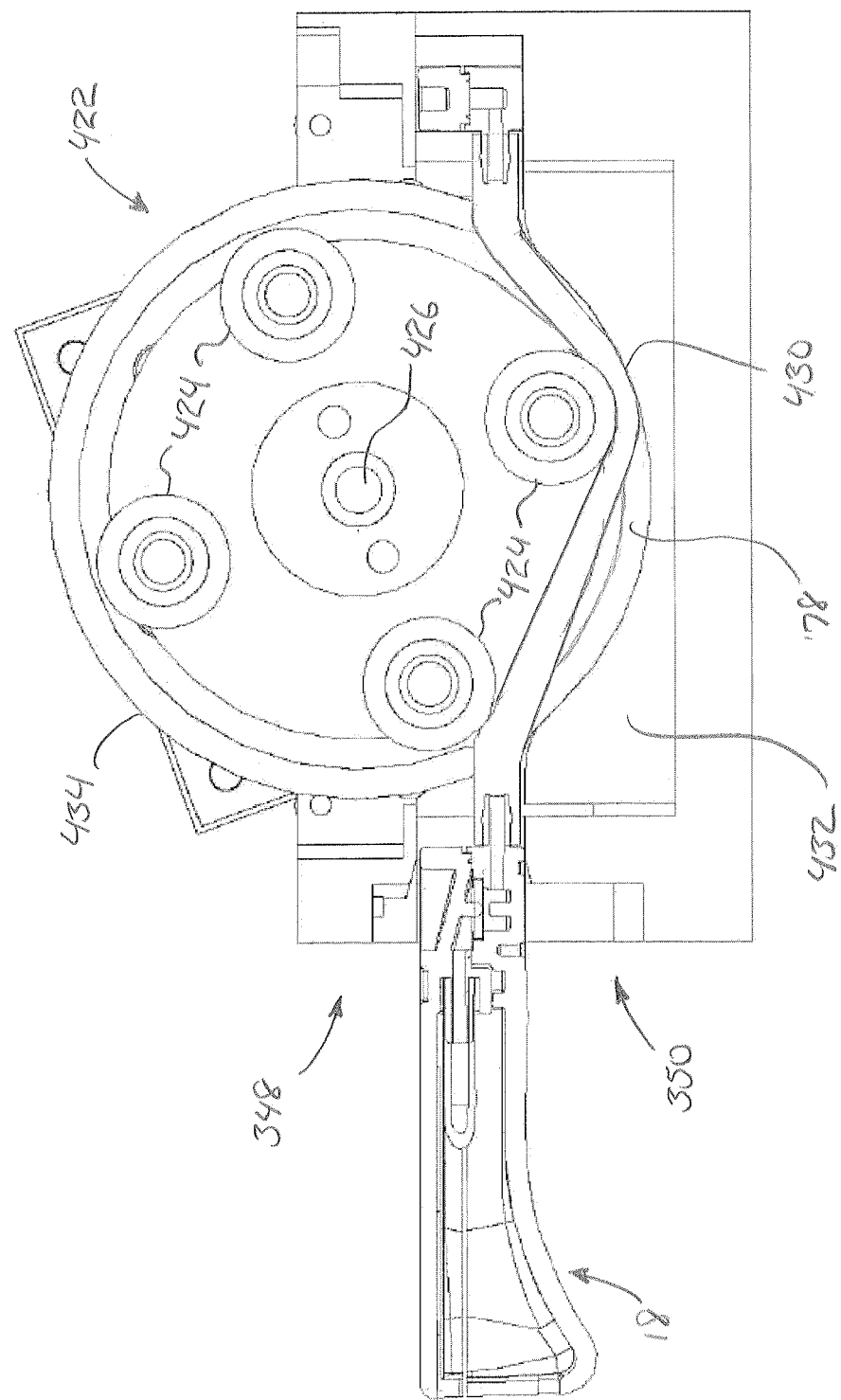
FIG. 30 is a cross sectional view taken through cartridge member, upper receptacle enclosure, lower receptacle enclosure and a fluid delivery apparatus at line 30-30 of FIG. 24.

Referring now to FIG. 29, FIG. 29 shows an exploded view of the cartridge member 18, upper receptacle enclosure 348, lower receptacle enclosure 350 and a fluid delivery apparatus 420. Fluid delivery apparatus 420 may comprise a peristaltic pump assembly 422, and more specifically a rotary peristaltic pump assembly. As shown in FIG. 30, compression elements shown as pinch rollers 424 of pump head 434 rotate about shaft 426 which may be turned by motor 428. As shown, when assembly is in its use position, rollers 424 may engage and compress pump tubing segment 78 in a known manner against opposing load bearing surface 430 of semi-circular shoe or base compression member 432 to pump fluid 502 from the fluid source 500 to the hand-held device 10.

Fluid 502 may be conveyed by peristaltic pump assembly 422 by waves of contraction placed externally on the delivery tubing segment 78 which are produced mechanically by rotating pinch rollers 424 which rotate on drive shaft 426 and intermittently compress the delivery tubing segment 78 against support surface 430. Peristaltic pumps are generally preferred, as the electro-mechanical force mechanism, here rollers 424 driven by electric motor 428, does not make contact with the fluid 502, thus reducing the likelihood of inadvertent contamination.

In the foregoing manner, a portion of the fluid delivery passage is defined by the delivery tubing segment 78, and delivery tubing segment 78 may be operable with the fluid delivery apparatus 420 of the electrosurgical unit 300. More particularly, delivery tubing segment 78 is configured to be compressed by the fluid delivery apparatus 420 of the electrosurgical unit 300.

Figure 31:
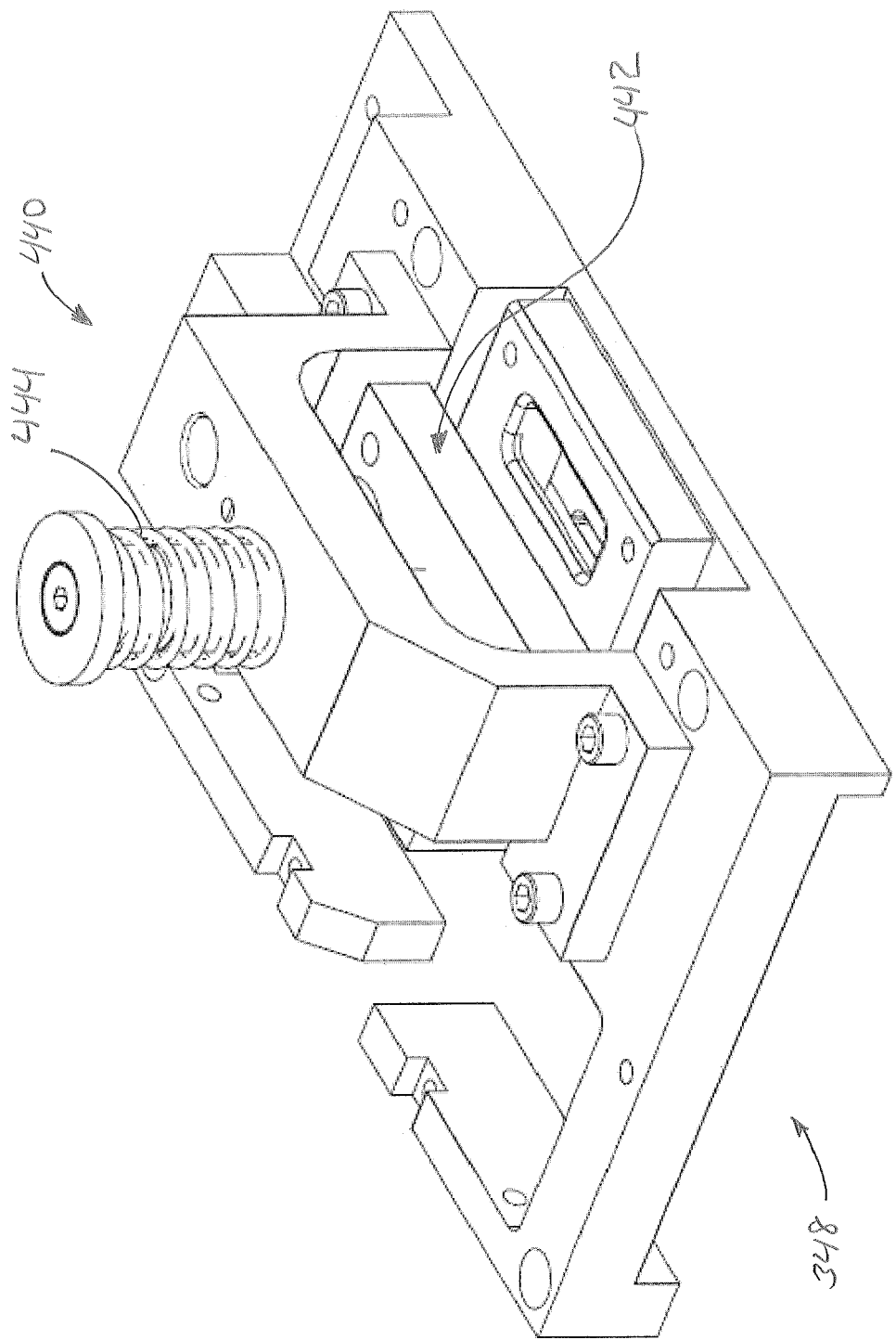
FIG. 31 is a perspective view of the upper receptacle enclosure with a radio-frequency power delivery apparatus.

Referring to FIG. 19 and FIG. 31, as docking mechanism 410 rotates downwards towards its use position, drive coupling 438 contacts radio-frequency power delivery apparatus 440 and pushes an electrical contact assembly 442 linearly downwards towards printed circuit board 24 of cartridge member 18 against the bias/compression force of spring 444. Conversely, upon docking mechanism 410 rotating upwards towards its non-use position, spring 444 raises electrical contact assembly 442 away from printed circuit board 24 and to its non-use position.

In the above manner, both power delivery apparatus 440 and fluid delivery apparatus 420 move simultaneously to save time as compared to if they were to move sequentially, as well jointly, thus requiring only one shared drive mechanism, here comprising motor 396, rather than two separate drive mechanisms.

Figure 32:
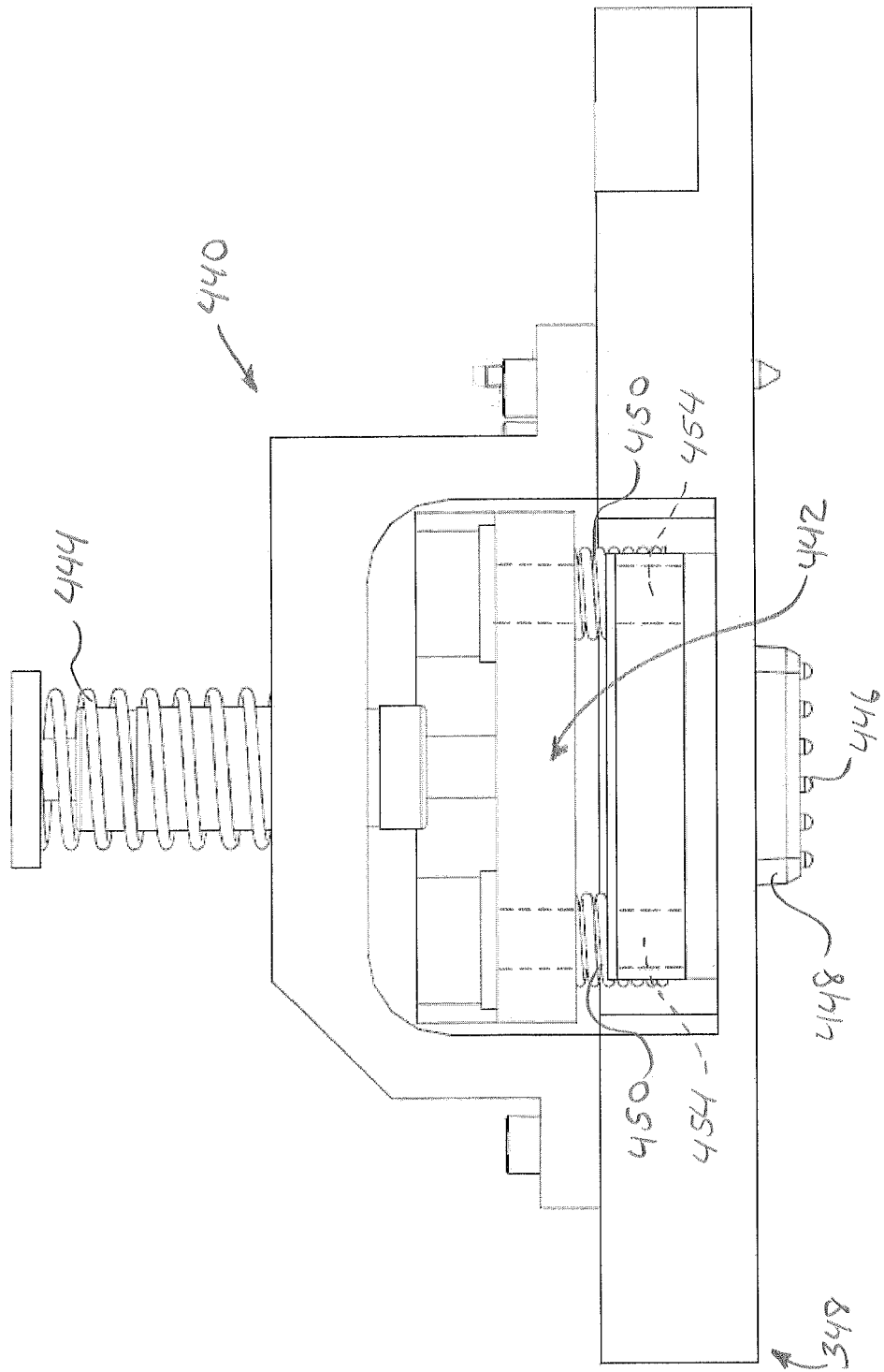
FIG. 32 is a side view of the upper receptacle enclosure with the radio-frequency power delivery apparatus.
Figure 33:
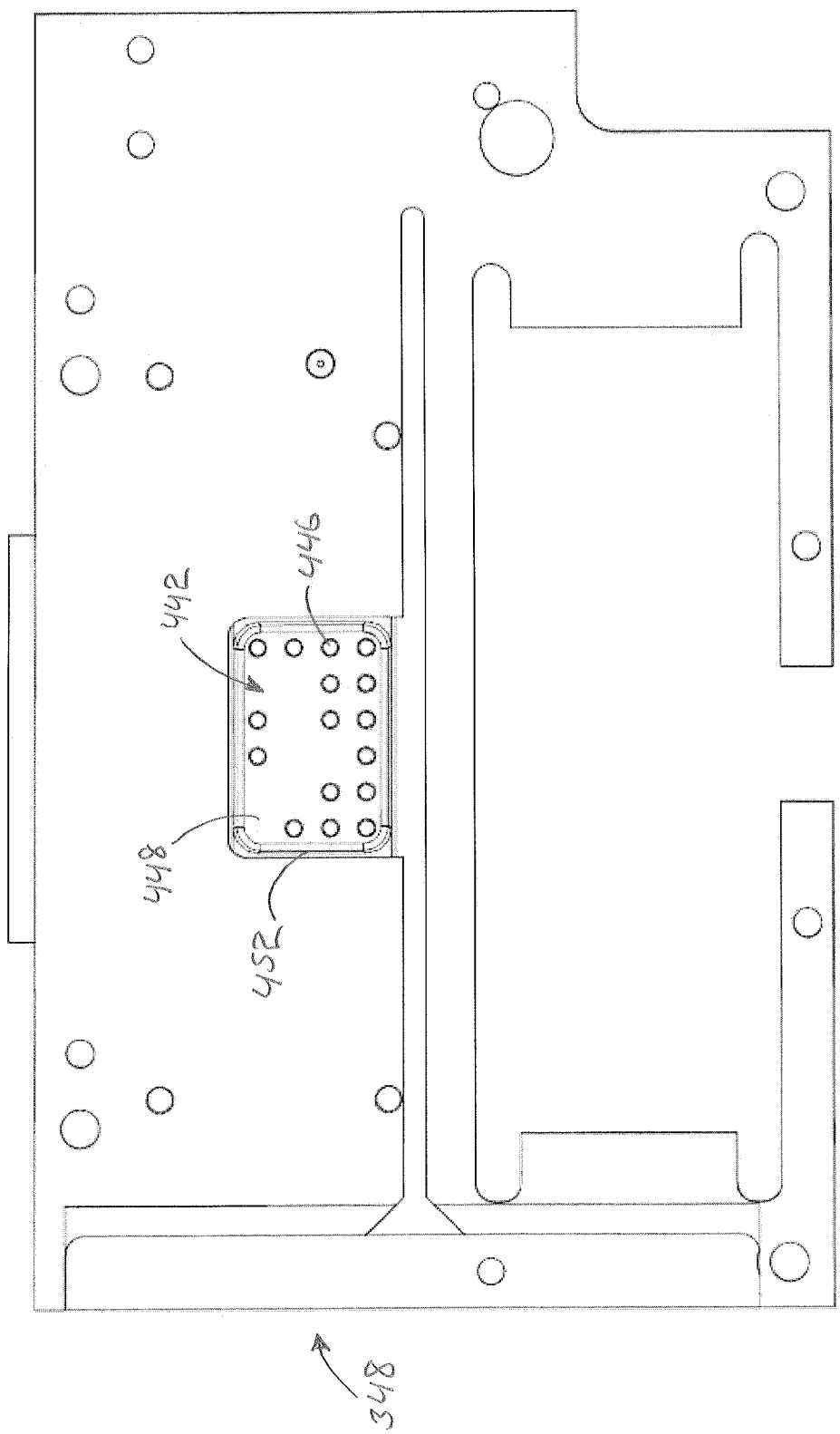
FIG. 33 is a bottom view of the upper receptacle enclosure with a radio-frequency power delivery apparatus.
Figure 34:
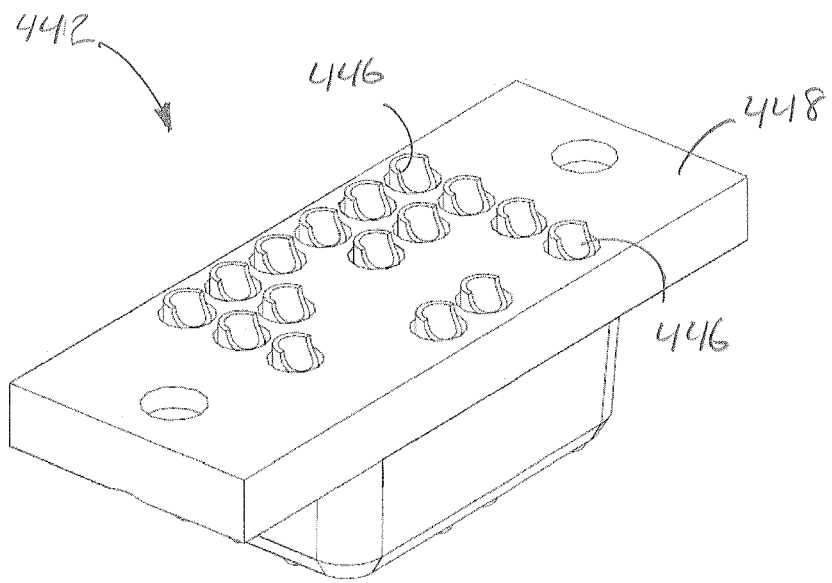
FIG. 34 is a perspective view of an electrical contact assembly for the radio-frequency power delivery apparatus comprising an electrical insulator/carrier and electrical contacts.
Figure 35:
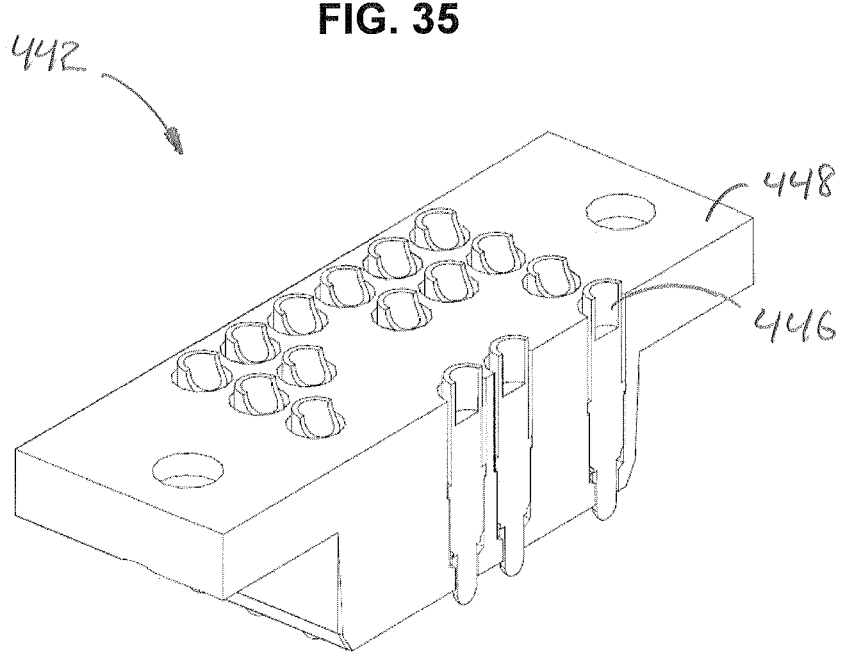
FIG. 35 is a cross sectional perspective view of the electrical contact assembly of FIG. 34.

As shown in FIG. 32 and FIG. 33, electrical contact assembly 442 may extend through an aperture 452 in upper receptacle enclosure 348. As shown in FIG. 34 and FIG. 35, electrical contact assembly 442 may comprise a plurality of electrical contacts 446 which extend through an electrical insulator/carrier 448.

Figure 36:
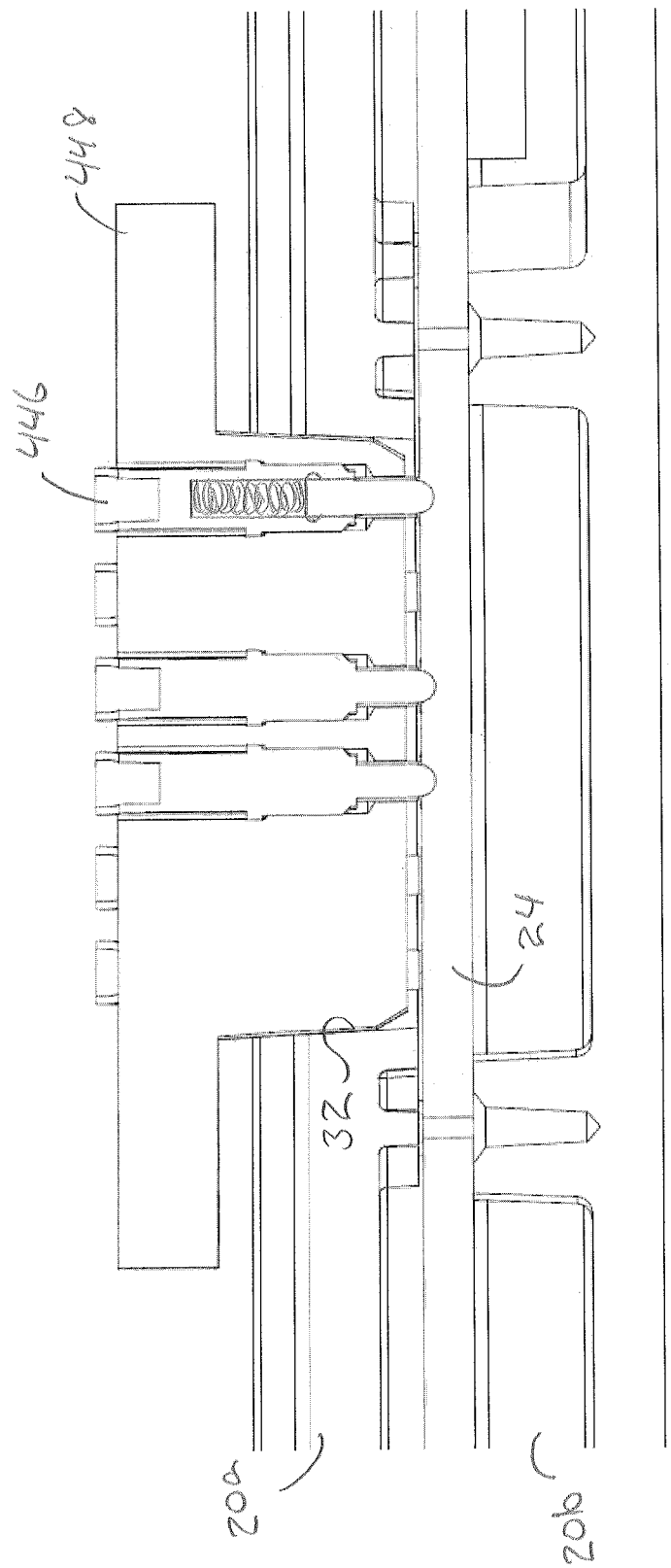
FIG. 36 is a cross sectional view of the electrical contact assembly and cartridge member.

As shown in FIG. 36, electrical contacts 446 may be configured to mate and electrically communicate with the electrical contacts of printed circuit board 24, as well as the electric components and circuitry of electrosurgical unit 300 in a manner known in the art.

Electrical contacts 446 may comprise a plurality of pogo (spring loaded) pins. As the pogo pins 446 make contact with printed circuit board 24, the pins 446 retract under load in a known manner until electrical insulator/contact carrier 448 may be positioned in contact with printed circuit board 24 and the pins 446 substantially retract into carrier 448. As shown in FIG. 36, an end portion of electrical contact carrier 448 may be configured to fit within aperture 32 of cartridge member 18.

Returning to FIG. 32, should electrical contact carrier 448 make contact with printed circuit board 24, radio-frequency power delivery apparatus 440 includes springs 450 which will compress upon reaching a load sufficient to overcome the bias/compression force of springs 450, with such force being lower than the force which may damage printed circuit board 24. In this manner, printed circuit board 24 may be protected from damage upon engagement with electrical contact assembly 442. Apparatus 440 also has the function of aligning contact carrier 448 to aperture 32 of cartridge member 18. In particular, the springs 450 and pins 454 (shown in phantom) are designed to allow the contact carrier 448 to float and align to the aperture 32 of cartridge member 18 as carrier 448 enters aperture 32, then return the contact carrier 448 to a straight position when retracted.

In the foregoing manner, cartridge assembly 16, and in particular cartridge member 18 may be operable with the radio-frequency power delivery apparatus 440 and fluid delivery apparatus 420 of electrosurgical unit 300.

Having discussed electrosurgical unit 300 in detail, attention will now be directed to a system in which device 10 and electrosurgical unit 300 may be arranged and used, with FIG. 37 showing a view of one embodiment of a system of the present invention having exemplary electrosurgical unit 300 in combination with a fluid source 500 and a handheld device 10. FIG. 37 shows a movable cart 504 having a support member 506 comprising a hollow cylindrical post which carries a platform 508 comprising a pedestal table to provide a flat, stable surface for location of the electrosurgical unit 300.

As shown, cart 504 further comprises a fluid source carrying pole 510 having a height which may be adjusted by sliding the carrying pole 510 up and down within the support member 506 and thereafter secured in position with a set screw. On the top of the fluid source carrying pole 510 is a cross support provided with loops at the ends thereof to provide a hook for carrying fluid source 500.

As shown in FIG. 37, fluid source 500 may comprise a bag of fluid from which the fluid 502 flows through drip chamber 48 after the bag is penetrated with a spike 50 located at the end of the drip chamber 48. In other embodiments, drip chamber 48 may be eliminated and tubing segment 46 may be attached directly to a spike 50. Thereafter, fluid 502 flows through flexible delivery tubing segment 46, cartridge member 18 and delivery tubing segment 106 of cable 42 to hand-piece 12 of device 10.

In the present embodiment the fluid 502 comprises saline solution, and even more specifically, normal (physiologic) saline. Although the description herein may make reference to saline as the fluid 502, other electrically conductive fluids can be used in accordance with the invention.

While an electrically conductive fluid having an electrically conductivity similar to normal saline is preferred, as will become more apparent with further reading of this specification, fluid 502 may also comprise an electrically non-conductive fluid. The use of a non-conductive fluid, while not providing all the advantage of an electrically conductive fluid, still provides certain advantages over the use of a dry electrode including, for example, reduced occurrence of tissue sticking to the electrodes 180a, 180b of device 10 and cooling of the electrodes and/or tissue. Therefore, it is also within the scope of the invention to include the use of a non-conducting fluid, such as, for example, deionized water.

As indicated above, electrosurgical unit 300 is configured to provide both monopolar and bipolar power output. However, electrosurgical unit 300 may particularly include a lock out feature which prevents both monopolar and bipolar output from being activated simultaneously.

Figure 38:
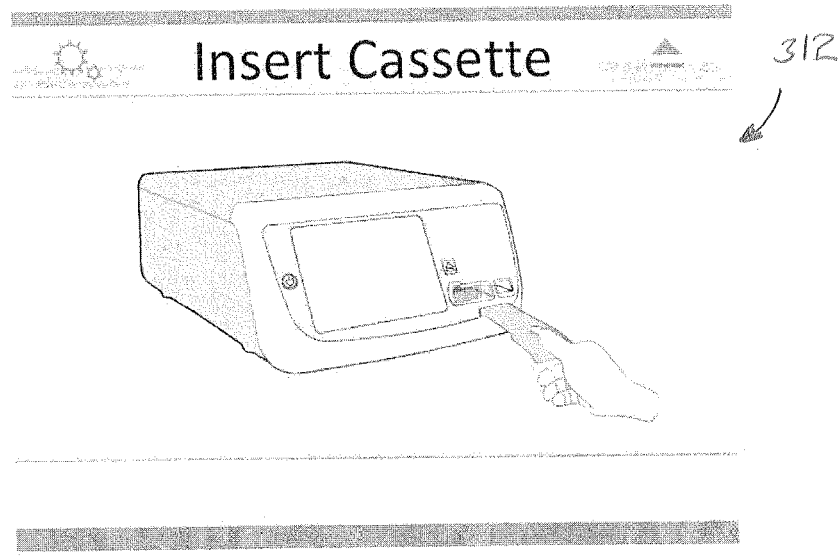
FIG. 38 is a display screen for the electrosurgical unit requesting insertion of the cartridge member.

When the power switch 304 is turned on electrosurgical unit 300, a number of touch control screens are presented to the user from the graphical user interface 306 to set up the use of device 10. As shown in FIG. 38, after performing an initial system check, a display 312 is presented to the user requesting insertion of cartridge member 18. Upon cartridge member 18 being placed in cartridge receptacle 310, controller 338 receives a signal of the presence thereof from a sensor. Controller 338 then initiates the movement of docking mechanism 410 from its non-use (unengaged) position to its use (engaged) position.

Upon reaching its use (engaged) position, controller 338 receives another signal to indicate such from another sensor. After receiving the signal, controller 338 now may access the memory 26 of cartridge member 18 for certain information stored thereon concerning device 10.

As indicated above, electrosurgical unit 300 may be configured to receive and read a stream of serial data including certain process parameters and other information from device 10. Controller 338 may determine if memory 26 includes a unique identifier such as a serial number for device 10. If so, the controller 338 may read and store the serial number to its own memory. Controller 338 may also determine if a fixed time period (e.g. 24 hours) for use of device 10 is included in memory 26. If so, controller 338 may apply the time period to an internal countdown clock, which may begin counting the time period down after the first radio-frequency power activation of unit 300 with device 10 therein. Thereafter, once the time period has expired, controller 338 may be programmed to associate the serial number with an expired device 10 and no longer operate device 10. In this manner, use of device 10 with cartridge 18 may be limited as intended to a single use disposable to better assure patient safety.

Figure 39:
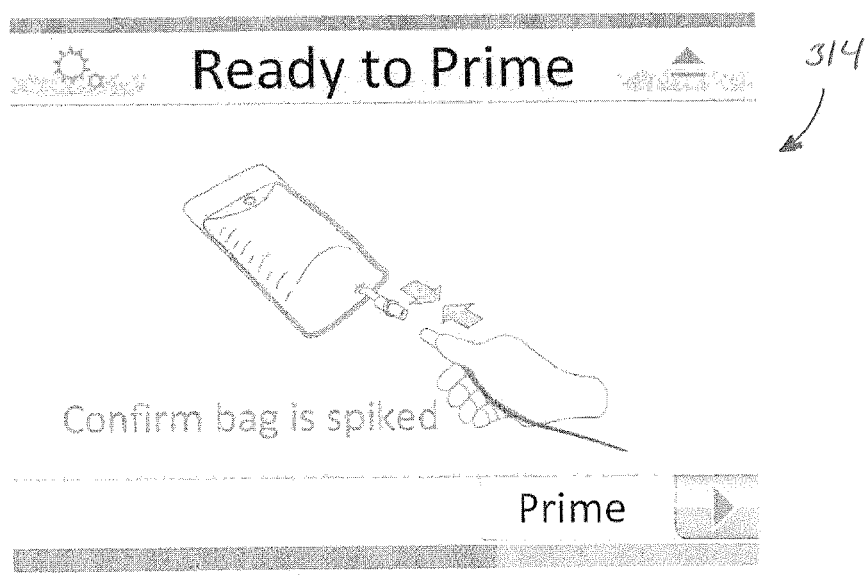
FIG. 39 is a display screen for the electrosurgical unit requesting priming of the electrosurgical tissue treatment device with fluid.

As shown in FIG. 39, after electrosurgical unit 300 senses the insertion of cartridge member 18, a display 314 is presented to the user to confirm that that fluid source 500 has been spiked, and to initiate priming of device 10 with fluid 502. Priming is desirable to inhibit radio-frequency power activation without the presence of fluid 502 in device 10.

Figure 40:
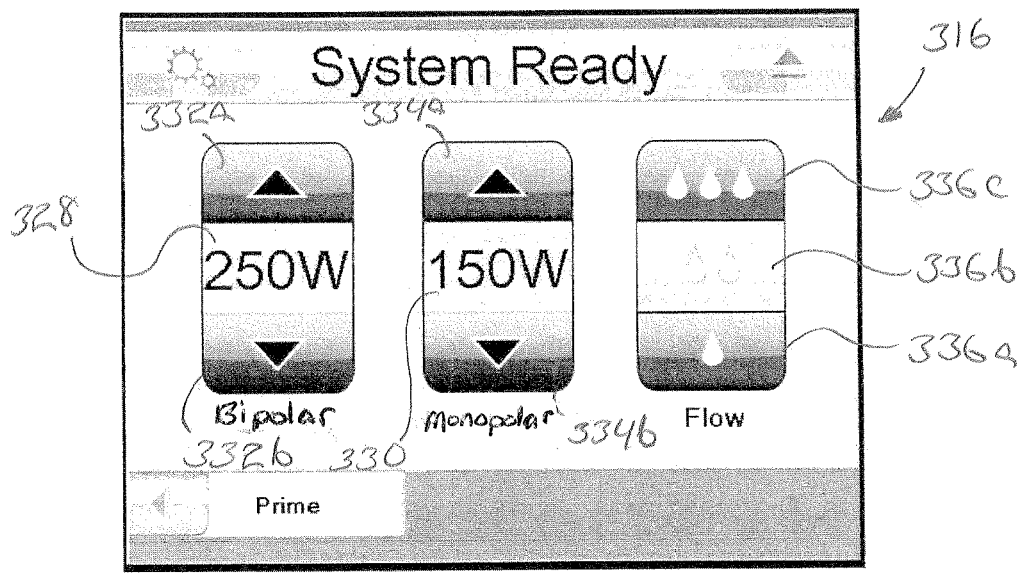
FIG. 40 is a display screen for the electrosurgical unit showing the electrosurgical unit and system is ready for operation.
Figure 41:
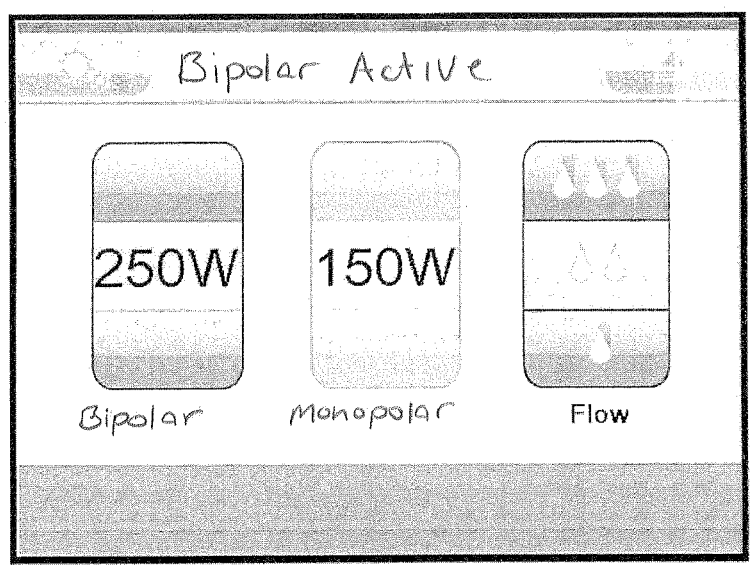
FIG. 41 is a display screen for the electrosurgical unit showing radio-frequency power is being provided from the unit.

After priming is complete, as shown in FIG. 40, display 316 is presented to the user indicating that the system is now ready for use. Additionally, display 316 presents the user with a default radio-frequency power level settings 328 and 330 numerically in watts, which may be thereafter increased or decreased by touching radio-frequency power level selectors 332a, 334a and 332b, 334b, respectively. RF power output may be set in 1 watt increments in the range of 1 to 40 watts, 5 watt increments in the range of 40 to 100 watts and 10 watt increments in the range of 100 to 300 watts. When radio-frequency power is activated, the system ready portion of the display will change to visually indicate that radio-frequency power is active as shown in FIG. 41.

In addition to display 316 presenting a user with a default radio-frequency power level setting, display 316 also presents the user with a plurality of fluid flow settings 336a, 336b and 336c, which correspond to fluid flow settings of low (represented by one fluid droplet), medium (represented by two fluid droplets) and high (represented by three fluid droplets), respectively. The appropriate setting will illuminate when selected to visual indication of such to the user, with the medium (or intermediate) setting generally being the default setting.

Controller 338 of electrosurgical unit 300 may also be programmed to obtain and read the default settings for radio-frequency power level and fluid flow level for device 10 which may be stored in memory 26 and thereafter set the unit 300 to these settings and present these default settings on display 316.

Controller 338 of electrosurgical unit 300 may be programmed to obtain and read a maximum power level for use of device 10 which is stored in memory 26. In this manner, electrosurgical unit 300 would not activate its radio-frequency power for device 10 should the user wish to select a radio-frequency power level greater than the maximum power level allotted.

Controller 338 of electrosurgical unit 300 may also be programmed to obtain and read data from memory 26 which relates a speed of the pump assembly 422, and therefore the throughput of fluid 502 expelled by fluid delivery apparatus 420, to a particular radio-frequency power level as well as a particular fluid flow setting. In this manner, the fluid flow from device 10 for a particular radio-frequency power level and fluid level may be better controlled and a greater power level would not be available for selection.

Figure 42:
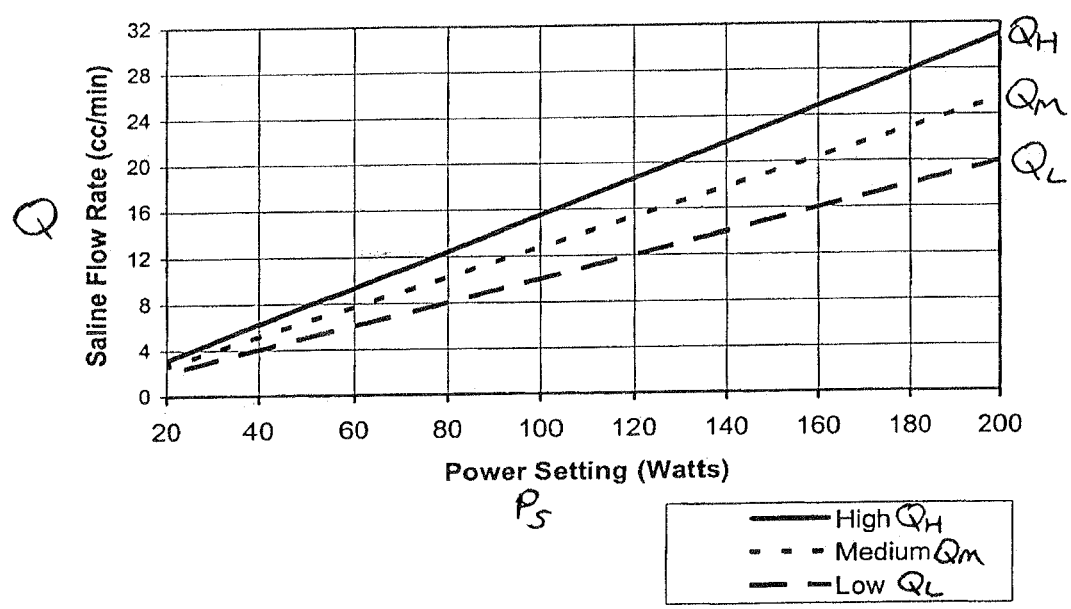
FIG. 42 is an exemplary graph showing a relationship of fluid flow rate Q in units of cubic centimetres per minute (cc/min) on the Y-axis, and the RF power setting $P_S$ in units of watts on the X-axis.

Exemplary functional relationships of fluid flow rate Q in units of cubic centimetres per minute (cc/min) on the Y-axis, and the bipolar RF power setting $P_S$ in units of watts on the X-axis as shown in FIG. 42. The relationships may be engineered to inhibit undesirable effects such as tissue desiccation, electrode sticking, smoke production and char formation, while at the same time not providing a fluid flow rate Q at a corresponding RF power setting $P_S$ which is so great as to provide too much electrical dispersion and cooling at the electrode/tissue interface. While not being bound to a particular theory, a more detailed discussion on how the fluid flow rate interacts with the radio frequency power, modes of heat transfer away from the tissue, fractional boiling of the fluid and various control strategies may be found in U.S. Publication No. 2001/0032002, published Oct. 18, 2001, assigned to the assignee of the present invention and hereby incorporated by reference in its entirety to the extent it is consistent.

As shown in FIG. 42, exemplary relationships $Q_L$, $Q_M$ and $Q_H$ are configured to increase the fluid flow rate Q linearly with an increasing radio-frequency power level setting $P_S$ for each of three fluid flow rate settings of low, medium and high, respectively. Conversely, the relationships $Q_L$, $Q_M$ and $Q_H$ are configured to decrease the fluid flow rate Q linearly with a decrease RF power setting $P_S$ for each of three fluid flow rate settings of low, medium and high, respectively. Accordingly, the data stored in the memory 26 of device 10 is to set a speed of the pump assembly 422 for a particular radio-frequency power level and a particular fluid flow level such that the throughput of fluid delivery apparatus 420 corresponds to the relationships provided in FIG. 42. The data may be stored in the form of equations, or as numerical data points as part of a database look-up table.

Figure 43:
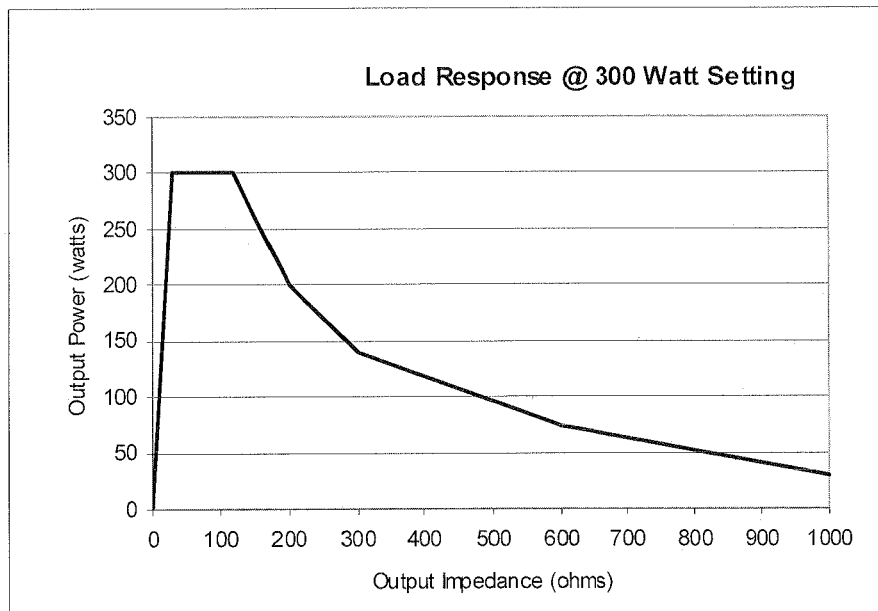
FIG. 43 is an exemplary graph of the bipolar RF power output versus impedance for the electrosurgical unit.

An exemplary bipolar radio-frequency power output curve of electrosurgical unit 300 is shown in FIG. 43. Impedance Z, shown in units of ohms on the X-axis and output power $P_O$ is shown in units of watts on the Y-axis. In the illustrated embodiment, the bipolar electrosurgical power (RF) is set to 300 watts. As shown in the figure, for an RF power setting $P_S$ of 300 watts, the output power $P_O$ will remain constant with the set RF power $P_S$ as long as the impedance Z stays between the low impedance cut-off of 30 ohms and the high impedance cut-off of 120 ohms. Below an impedance Z of 30 ohms, the output power $P_O$ will decrease as shown by the low impedance ramp. Above an impedance Z of 120 ohms, the output power $P_O$ will also decrease as shown by the high impedance ramp.

Figure 44:
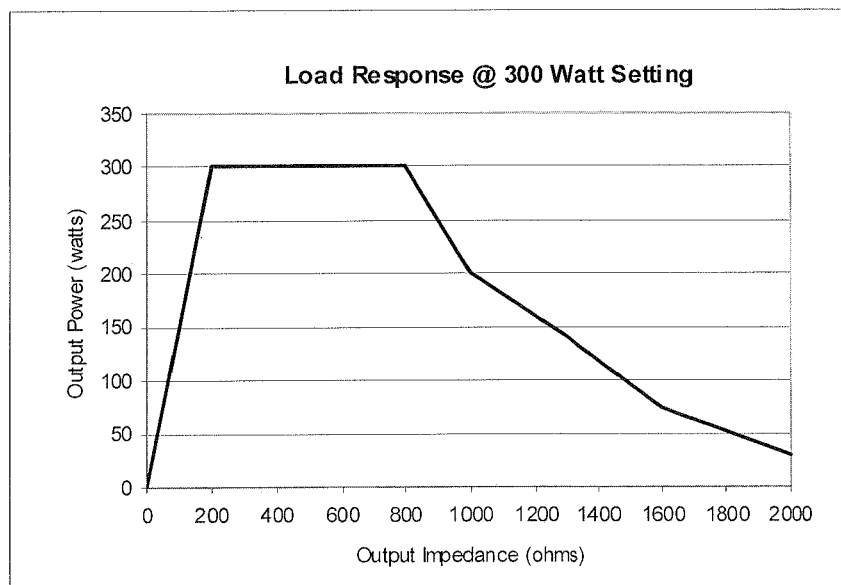
FIG. 44 is an exemplary graph of the monopolar RF power output versus impedance for the electrosurgical unit.

With respect to monopolar power output, an exemplary monopolar radio-frequency power output curve of electrosurgical unit 300 is shown in FIG. 44. Impedance Z, shown in units of ohms on the X-axis and output power $P_O$ is shown in units of watts on the Y-axis. In the illustrated embodiment, the bipolar electrosurgical power (RF) is set to 300 watts. As shown in the figure, for an RF power setting $P_S$ of 300 watts, the output power $P_O$ will remain constant with the set RF power $P_S$ as long as the impedance Z stays between the low impedance cut-off of 200 ohms and the high impedance cut-off of 800 ohms. Below an impedance Z of 200 ohms, the output power $P_O$ will decrease as shown by the low impedance ramp. Above an impedance Z of 800 ohms, the output power $P_O$ will also decrease as shown by the high impedance ramp.

In another embodiment, hand-piece 12 and electrosurgical unit 300 may be connected by cartridge assembly 16a as shown in FIG. 47-50. As with prior embodiments, electrosurgical unit 300 is configured to connect with cartridge assembly 16a, and in particular cartridge member 18. As shown, cartridge member 18 may again comprise a cartridge body 20 having mating cartridge body portions 20a, 20b. Furthermore, to facilitate proper installation of cartridge member 18 with electrosurgical unit 300, cartridge body 20 may include a directional indicator 30 to show the direction in which cartridge member 18 is to be installed in electrosurgical unit 300.

As shown, fluid delivery tubing segment 46 extends through a tubular aperture 52 formed in cartridge body 20. Fluid delivery tubing segment 46 then may be connected with a first end of fluid delivery tubing segment 78, which is configured to operate specifically with fluid delivery apparatus 420 (which again may comprise a peristaltic pump assembly 422, and more specifically a rotary peristaltic pump assembly), using a barbed fluid line connecter 53 at the end thereof (shown in phantom). In turn, the opposing end of fluid delivery tubing segment 78 may be connected to fluid delivery tubing segment 106 of cable 42 using a barbed fluid line connecter 53 at the end thereof. Fluid delivery tubing segment 106 then extends through tubular aperture 54.

To connect with radio-frequency power delivery apparatus 440, the electrical contacts for cartridge member 18 now comprise male connectors 56 (e.g. pins or other type prongs as opposed to electrical contact pads) which are configured to mate with female connectors 58 (in lieu of pogo pins 446) located in rectangular protrusion 66 of the electrosurgical generator 300. As shown, male connectors 56 are located within a rectangular recess 68 formed in cartridge body 20 to better protect them and lessen their exposure to being inadvertently bent or otherwise damaged.

Cartridge assembly 16a is made operable with electrosurgical unit 300 by first installing cartridge body 20 with the radio-frequency power delivery apparatus 440 of electrosurgical unit 300. More particularly, rectangular protrusion 66 is configured to mate with rectangular recess 68, particularly using an interference fit, and connect male connectors 56 with female connectors 58.

After the electrical connections have been completed, tubing segment 78 may be loaded into fluid delivery apparatus 420 which, as shown, may comprise a peristaltic pump assembly 422. As shown, the tubing segments 46/78/106 form an enclosed loop 88 with cartridge body 20. With the semi-circular anvil or compression member 432 of the peristaltic pump assembly 422 in a raised or non-use position as understood in the art, loop 88 may then be loaded into the confines of the open pump assembly 422 between arcuate support surface 430 and the pinch rollers 424.

During installation, if the size of loop 88 is too small or too large, the size of the loop 88 may be adjusted by moving tubing segment 46 relative to cartridge body 20 in an appropriate direction (i.e. by moving the tubing segment 46 into the tubular aperture 52 of cartridge body 20 to make loop 88 smaller or out of the cartridge body 20 to make loop 88 larger). Thereafter, once the size of loop 88 is appropriate, the anvil or compression member 432 may be lowered into its use position. In this manner, rollers 424 engage and compress pump tubing segment 78 in a known manner against opposing load bearing support surface 430 to pump fluid 502 from the fluid source 500 to the device 10.

With use of cartridge assembly 16a, the electrical contacts for electrosurgical unit 300 are not movable from a non-use to a use position as with the configuration of the electrosurgical unit for use of cartridge assembly 16, which may simplify the configuration of electrosurgical unit 300. Also, it should be understood that cartridge member 18 of cartridge assembly 16a may include any electrical components which may be used with cartridge member 16, including printed circuit board 24 and memory 26 within the confines of cartridge body 20.

Figure 51:
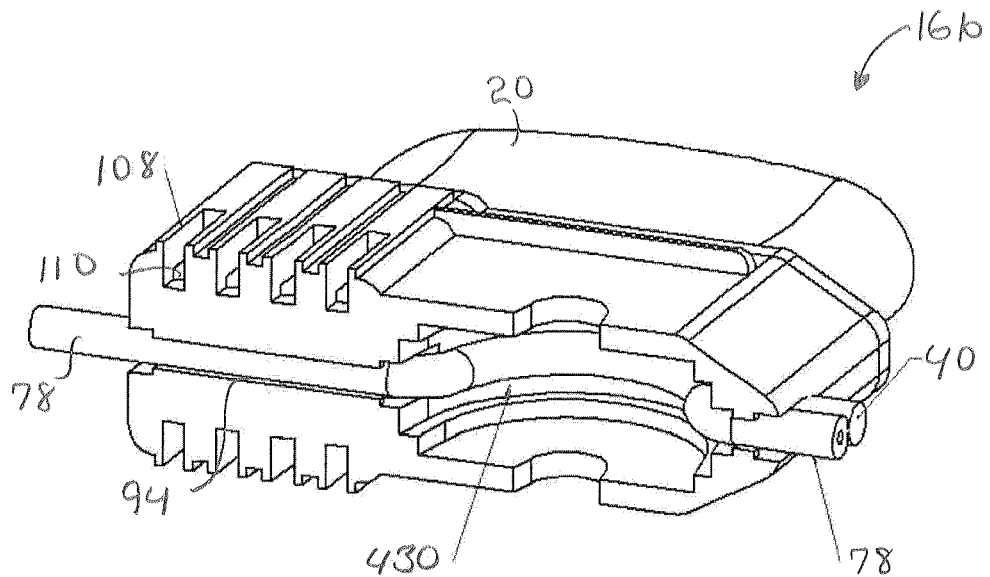
FIG. 51 is a bottom perspective view of a cartridge assembly according to another embodiment of the invention.
Figure 52:
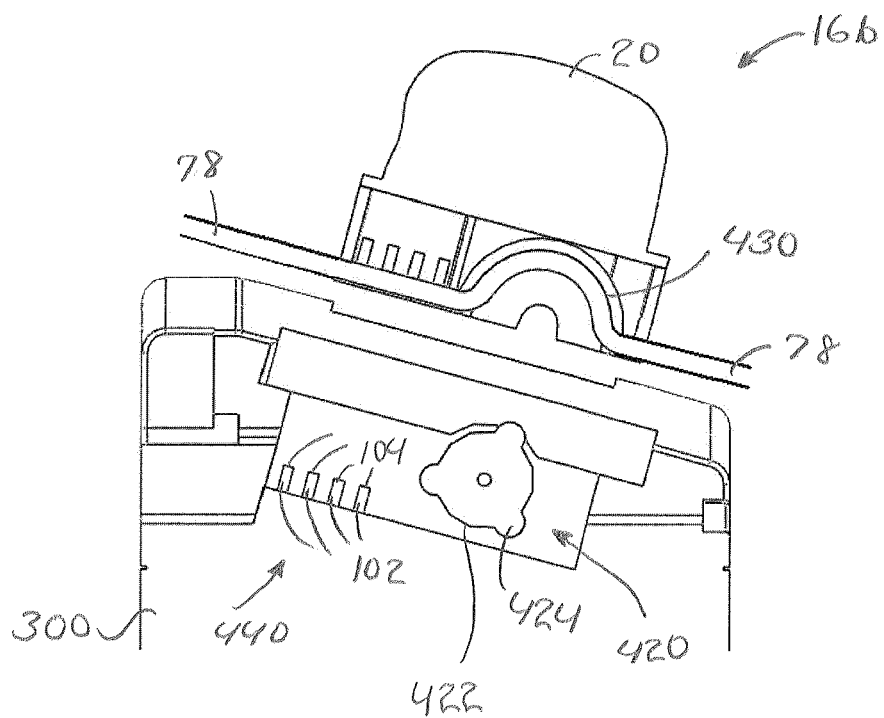
FIG. 52 is a side view of the cartridge assembly of FIG. 51 prior to being engaged with an electrosurgical unit.
Figure 53:
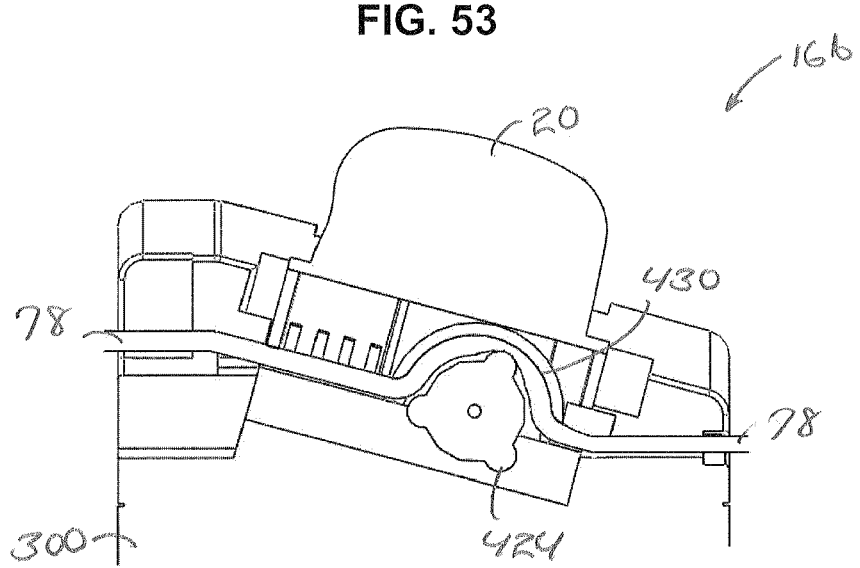
FIG. 53 is a side view of the cartridge assembly of FIG. 51 after being engaged with the electrosurgical unit.

In another embodiment, hand-piece 12 of device 10 and electrosurgical unit 300 may be connected by cartridge assembly 16b as shown in FIGS. 51-53. As with prior embodiments, electrosurgical unit 300 is configured to connect with cartridge assembly 16b, particular cartridge member 18, and vice-versa. As shown, cartridge member 18 may again comprise a cartridge body 20.

As shown, fluid delivery tubing segment 78 passes through a U-shaped passage 94 formed in cartridge body 20. Tubing segment 78 has a U-shaped portion which may rest against arcuate support surface 430. The electrical contacts for cartridge member 18 now comprise metal strips or blades 110 which are configured to mate with metal strips 102 on the electrosurgical generator 300. As shown, each metal strip 110 is located at the based of a rectangular slot 108 formed in cartridge body 20 to better protect them and lessen their exposure to being inadvertently bent or otherwise damaged. Each rectangular slot 108 is configured to mate with a rectangular protrusion 114 located on electrosurgical unit 300.

Cartridge assembly 16b is made operable with electrosurgical unit 300 by installing cartridge body 20 with radio-frequency power delivery apparatus 440 and fluid delivery apparatus 420 of electrosurgical unit 300. More particularly, rectangular protrusions 114 are configured to mate with rectangular slots 108, particularly using an interference fit and connect metal strips 102 with metal strips 110 as cartridge body 20.

As the electrical connections are completed with radio-frequency power delivery apparatus 440, tubing segment 78 is simultaneously made operable with fluid delivery apparatus 420 which, as shown, may comprise a peristaltic pump assembly 422. As shown, cartridge body 20 is configured to form tubing segment 78 into an arcuate, here semi-circular, shape which may be supported against arcuate support surface 430. In this manner, rollers 424 engage and compress pump tubing segment 78 in a known manner against opposing load bearing support surface 430 to pump fluid 502 from the fluid source 500 to device 10.

With use of cartridge assembly 16b, the electrical contacts for electrosurgical unit 300, as well as the fluid delivery apparatus 420 are stationary and not movable from a non-use to a use position as with the configuration of the electrosurgical unit for use of cartridge assembly 16, which may simplify the configuration of electrosurgical unit 300. Furthermore, with use of cartridge assembly 16b, the electrical and fluid connections are made almost simultaneously and without manual adjustment of the fluid delivery segment 78 as with cartridge assembly 16a.

Figure 45:
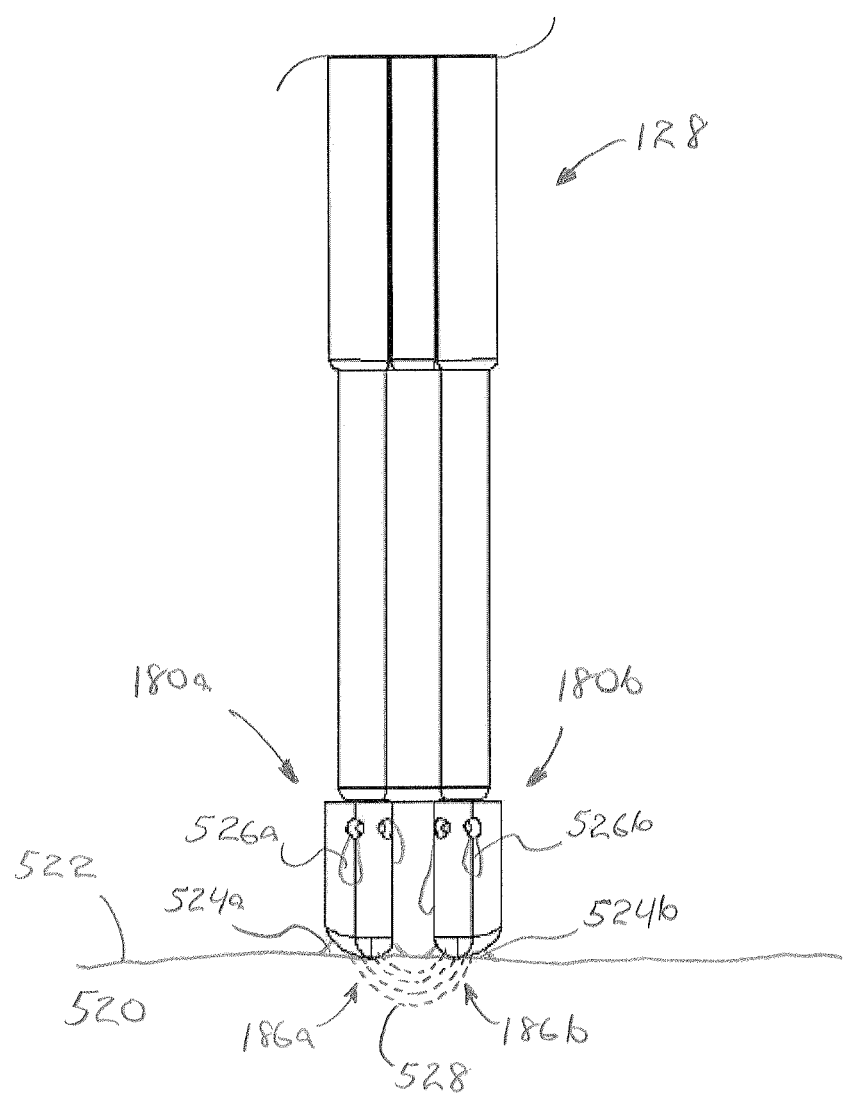
FIG. 45 is a close-up view of a distal end portion of the device of FIG. 1 with an exemplary fluid coupling to a tissue surface of tissue.

Having discussed a system in which device 10 and electrosurgical unit 300 may be arranged and used, attention will now focus on an application of device 10 to treating tissue. As shown in FIG. 45, one way in which device 10 may be used is with the longitudinal axis of electrodes 180a, 180b vertically orientated, and the distal end portion 186a, 186b of electrodes 180a, 180b laterally spaced adjacent tissue surface 522 of tissue 520. When device 10 is used in this manner, electrodes 180a, 180b are connected to electrosurgical unit 300 and receive bipolar radio frequency power which forms an alternating current electrical field 528 in tissue 520 located between electrodes 180a, 180b. In the presence of alternating current, the electrodes 180a, 180b alternate polarity between positive and negative charges with current flow from the positive to negative charge. Without being bound to a particular theory, heating of the tissue is performed by electrical resistance heating.

Fluid 502, in addition to providing an electrical coupling between the device 10 and tissue 520, lubricates surface 522 of tissue 520 and facilitates the movement of electrodes 180a, 180b across surface 522 of tissue 520. During movement of electrodes 180a, 180b, electrodes 180a, 180b typically slide across the surface 522 of tissue 520. Typically the user of device 10 slides electrodes 180a, 180b across surface 522 of tissue 520 back and forth with a painting motion while using fluid 502 as, among other things, a lubricating coating. The thickness of the fluid 502 between the distal end portions 186a, 186b of electrodes 180a, 180b and surface 522 of tissue 520 at the outer edge of couplings 524a, 524b is in the range between and including 0.05 mm to 1.5 mm. Also, in certain embodiments, the distal end portion 186a, 186b of electrodes 180a, 180b may contact surface 522 of tissue 520 without any fluid 502 in between.

As shown in FIG. 45, fluid 502 expelled from fluid outlets 208a/210a/212a/214a and 208b/210b/212b/214b may form into droplets 526a, 526b which flow distally on electrodes 180a, 180b. As shown in FIG. 45, droplets 526a, 526b may form at varying times from fluid 502 expelled from any one of the fluid outlets. Also, fluid 502 may be expelled in varying quantity from each of the fluid outlets, depending on, for example, device orientation, pressure, flow rate and varying fluid outlet sizes. With use of device 10, the size of droplets 526a, 526b may also vary due to changes in the surface finish of the electrodes 180a, 180b, for example, as a result of being contaminated by blood and tissue.

Figure 46:
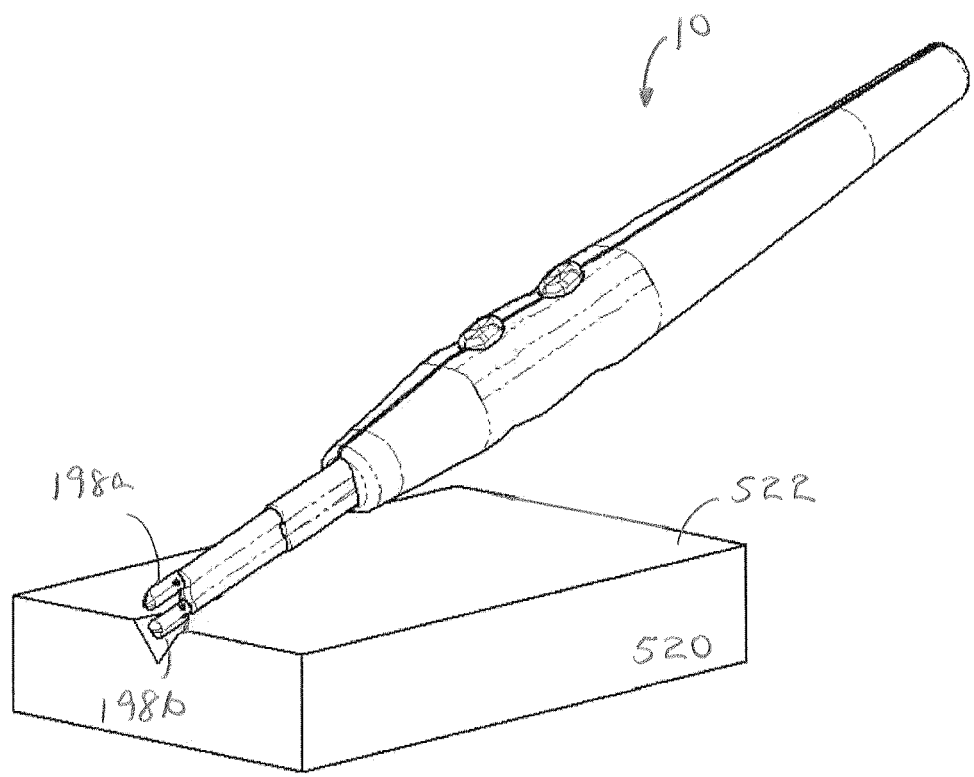
FIG. 46 is a perspective view of the device of FIG. 1 cutting tissue.
Figure 47:
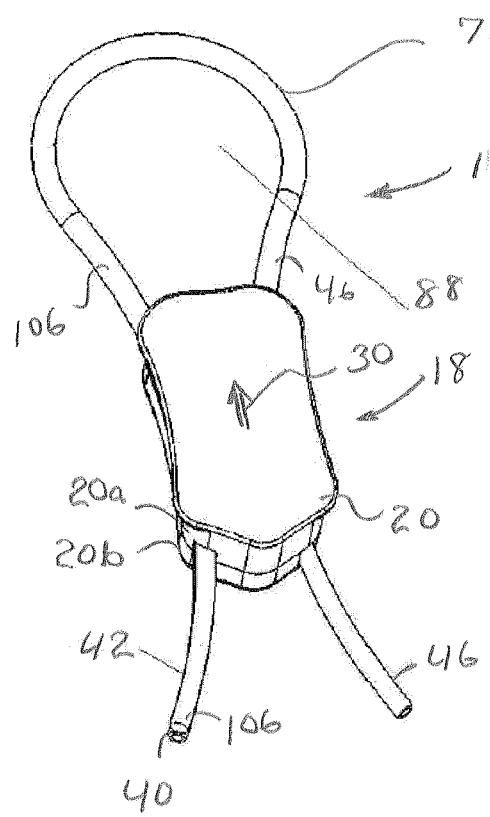
FIG. 47 is a front perspective view of a cartridge assembly according to another embodiment of the invention.
Figure 48:
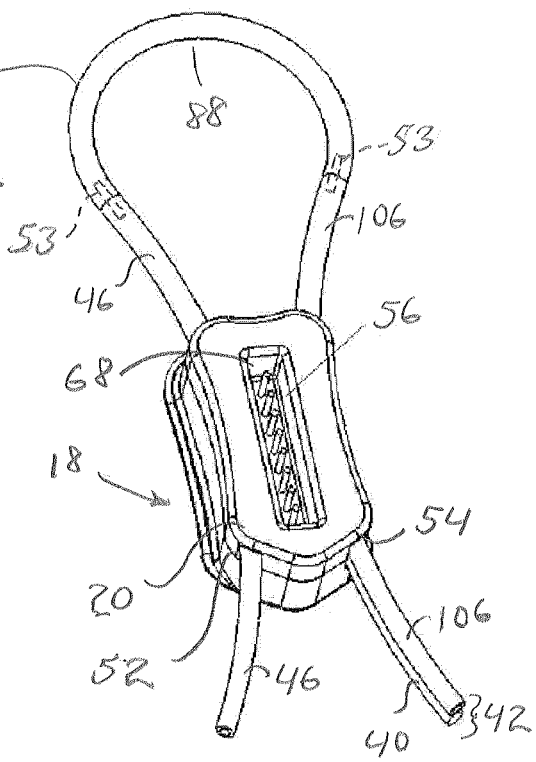
FIG. 48 is a rear view of the cartridge assembly of FIG. 47.
Figure 49:
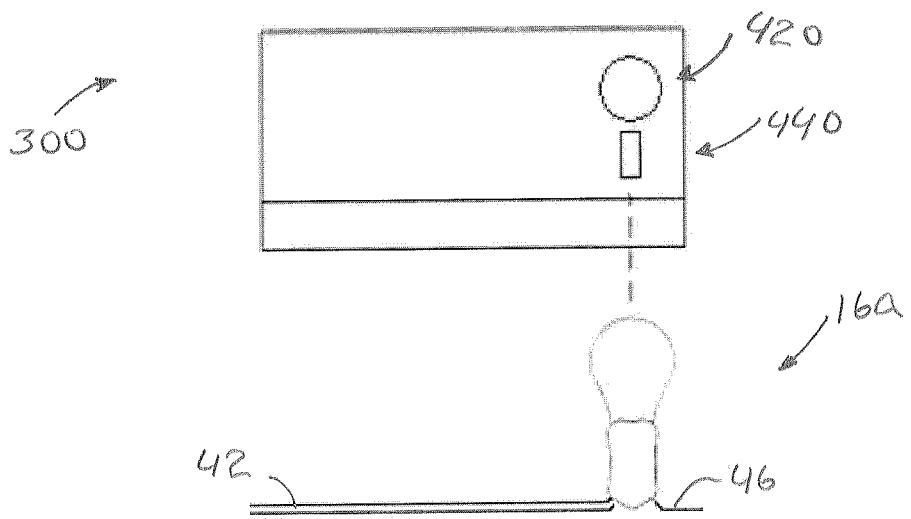
FIG. 49 is a front perspective view of the cartridge assembly of FIGS. 47-48 prior to being engaged to an electrosurgical unit.
Figure 50:
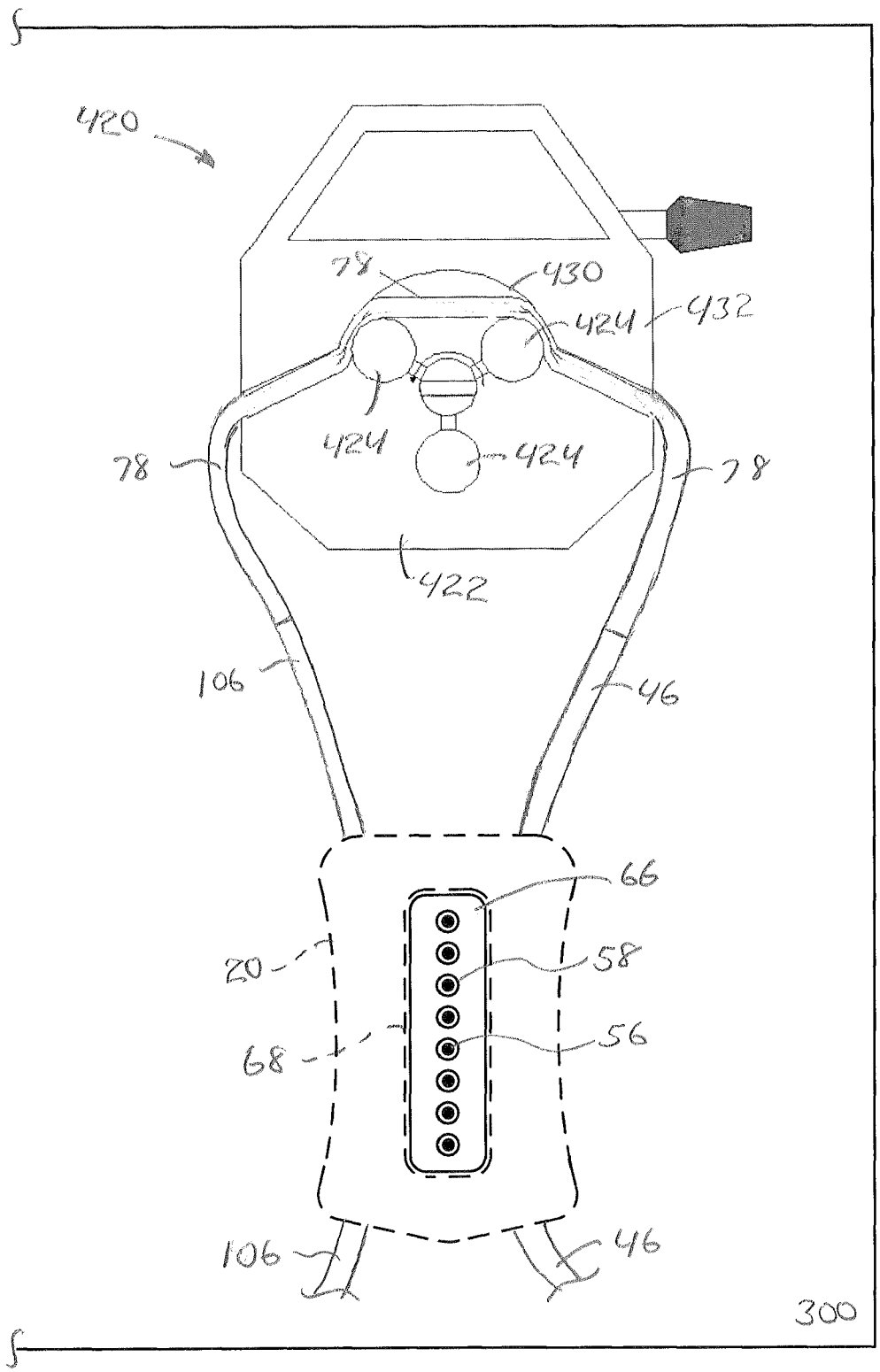
FIG. 50 is a close-up front view of the cartridge assembly of FIGS. 47-48 after being engaged to the electrosurgical unit.

As shown in FIG. 45, fluid couplings 524a, 524b comprise discrete, localized webs and more specifically comprise triangular shaped webs or bead portions providing a film of fluid 502 between surface 522 of tissue 520 and electrodes 180a, 180b. When the user of device 10 places electrodes 180*a*, 180*b* at a tissue treatment site and moves electrodes 180*a*, 180*b* across the surface 522 of the tissue 520, fluid 502 is expelled from fluid outlets 208*a*/210*a*/212*a*/214*a* and 208*b*/210*b*/212*b*/214*b* around the surfaces of electrodes 180*a*, 180*b* and onto the surface 522 of the tissue 520 via couplings 524*a*, 524*b*. At the same time, radio-frequency electrical energy, shown by electrical field lines 528, is provided to tissue 520 at tissue surface 522 and below tissue surface 522 into tissue 520 through fluid couplings 524*a*, 524*b*. As shown in FIG. 46, device 10 may be used to cut tissue by applying either cutting edge 198*a* or 198*b* to tissue 520, depending which electrode 180*a*, 180*b* is utilized.

Device 10 may be used to perform a solid organ resection such as a liver resection. Edge 198*a* or 198*b* may be first used to score the outer capsule of the liver along the planned line of resection. Thereafter, the distal end portions 186*a*, 186*b* of electrodes 180*a*, 180*b* may be moved back and forth along the line, with radio frequency power and the flow of fluid on, resulting in coagulation of the liver parenchyma beneath the scored capsule. As the tissue is coagulated under and around the electrode surfaces, the electrodes 180*a*, 180*b* may be used to separate and blunt dissect the coagulated parenchyma and enter the resulting crevice. As the distal end portions 186*a*, 186*b* of electrodes 180*a*, 180*b* treat the parenchyma, the treated parenchyma looses integrity and becomes easier to separate, either alone or in conjunction with separation force applied by electrodes 180*a*, 180*b* from the user of the device.

Blunt dissection of the coagulated parenchyma is performed by continuous abrading or splitting apart of the parenchyma with substantially the same back and forth motion as coagulation and with the device 10 being held substantially in the same orientation as for coagulation of the liver parenchyma. However, with blunt dissection, the surgeon typically applies more force to the tissue. In various embodiments, once the liver parenchyma is coagulated, blunt dissection may be performed with or without monopolar radio frequency power (i.e., on or off) and/or with or without the presence of fluid from device 10. Additionally or alternatively, the tissue on opposing sides of the line of resection may be placed into tension perpendicular to the line of resection to facilitate resection. Furthermore, resection may also be accomplished by sharp dissection with edge 198*a* or 198*b* of electrodes 180*a*, 180*b*. Thus, with device 10, a surgeon may perform a resection procedure in a number of different ways.

As the parenchyma is resected, blood vessels within the parenchyma may be uncovered which extend across or transverse the line of resection. Device 10 may be used to shrink and seal these vessels by heating and shrinking the collagen contained in the walls of the vessels thus decreasing the diameter of the lumen of these vessels. For vessels with a diameter too large to completely occlude the lumen, the vessels may be tied with suture on each side of the line of resection and thereafter severed therebetween. If such vessels are not first uncovered by removing the surrounding parenchyma tissue and without being severed, they may bleed profusely and require much more time to stop the bleeding. Consequently, it may be desirable to avoid separation by sharp dissection in situations where large vessels are not first uncovered and exposed.

This technique can also be used on other parenchymal organs such as the pancreas, the kidney, and the lung. In addition, it may also be useful on muscle tissue and subcutaneous fat. It's use can also extend to tumors, cysts or other tissue masses found in the urological or gynecological areas. It would also enable the removal of highly vascularized tumors such as hemangiomas.

The devices disclosed herein are particularly useful as non-coaptive devices that provide cutting of tissue, as well as coagulation, hemostasis and sealing of tissue to inhibit blood and other fluid loss during surgery. In other words, grasping of the tissue is not necessary to shrink, coagulate, cut and seal tissue against blood loss, for example, by shrinking collagen and associated lumens of blood vessels (e.g., arteries, veins) to provide the desired hemostasis of the tissue. Furthermore, the control system of the electrosurgical unit 300 is not necessarily dependent on tissue feedback such as temperature or impedance to operate. Thus, the control system of electrosurgical unit 300 may be open loop with respect to the tissue which simplifies use.

Device 10 disclosed herein are particularly useful to surgeons to achieve hemostasis after cutting through soft tissue, as part of hip or knee arthroplasty. The distal end portions 186*a*, 186*b* can be painted over the raw, oozing surface 522 of tissue 520 to seal the tissue 520 against bleeding, or focused on individual larger bleeding vessels to stop vessel bleeding. As part of the same or different procedure, device 10 is also useful to stop bleeding from the surface of cut bone, or osseous, tissue as part of any orthopedic procedure that requires bone to be cut.

As is well known, bone, or osseous tissue, is a particular form of dense connective tissue consisting of bone cells (osteocytes) embedded in a matrix of calcified intercellular substance. Bone matrix mainly contains collagen fibers and the minerals calcium carbonate, calcium phosphate and hydroxyapatite. Among the many types of bone within the human body are compact bone and cancellous bone. Compact bone is hard, dense bone that forms the surface layers of bones and also the shafts of long bones. It is primarily made of haversian systems which are covered by the periosteum. Compact bone contains discrete nutrient canals through which blood vessels gain access to the haversian systems and the marrow cavity of long bones. For example, Volkmann's canals which are small canals found in compact bone through which blood vessels pass from the periosteum and connect with the blood vessels of haversian canals or the marrow cavity. Devices 30*a*-30*e* disclosed herein may be particularly useful to treat compact bone and to provide hemostasis and seal bleeding vessels (e.g. by shrinking to complete close) and other structures associated with Volkmann's canals and Haversian systems.

In contrast to compact bone, cancellous bone is spongy bone and forms the bulk of the short, flat, and irregular bones and the ends of long bones. The network of osseous tissue that makes up the cancellous bone structure comprises many small trabeculae, partially enclosing many intercommunicating spaces filled with bone marrow. Consequently, due to their trabecular structure, cancellous bones are more amorphous than compact bones, and have many more channels with various blood cell precursors mixed with capillaries, venules and arterioles. Device 10 disclosed herein may be particularly useful to treat cancellous bone and to provide hemostasis and seal bleeding structures such as the above micro-vessels (i.e. capillaries, venules and arterioles) in addition to veins and arteries. Device 10 may be particularly useful for use during orthopedic knee, hip, shoulder and spine procedures (e.g. arthroplasty).

During a knee replacement procedure, the condyle at the distal epiphysis of the femur and the tibial plateau at the proximal epiphysis of the tibia are often cut and made more planer with saw devices to ultimately provide a more suitable support structure for the femoral condylar prosthesis and tibial prosthesis attached thereto, respectively. The cutting of these long bones results in bleeding from the cancellous bone at each location. In order to seal and arrest the bleeding from the cancellous bone which has been exposed with the cutting of epiphysis of each long bone, bipolar device 10 may be utilized. Thereafter, the respective prostheses may be attached.

Turning to a hip replacement procedure, the head and neck of the femur at the proximal epiphysis of the femur may be removed, typically by cutting with a saw device, and the intertrochantic region of the femur may be made more planer to provide a more suitable support structure for the femoral stem prosthesis subsequently attached thereto. With respect to the hip, a ball reamer may be used to ream and enlarge the acetabulum of the innominate (hip) bone to accommodate the insertion of an acetabular cup prosthesis therein, which will provide the socket into which the head of the femoral stem prosthesis fits. The cutting of the femur and reaming of the hip bone typically results in bleeding from the cancellous bone at each location. In order to seal and arrest the bleeding from the cancellous bone which has been cut and exposed, device 10 may be utilized. Thereafter, as with the knee replacement, the respective prostheses may be attached.

Device 10 may be utilized for treatment of connective tissues, such as for shrinking intervertebral discs during spine surgery. Intervertebral discs are flexible pads of fibro-cartilaginous tissue tightly fixed between the vertebrae of the spine. The discs comprise a flat, circular capsule roughly an inch in diameter and 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Device 10 may be utilized to shrink protruding and herniated intervertebral discs which, upon shrinking towards normal size, reduces the pressure on the surrounding nerves and relieves the pain and immobility. Device 10 may be applied via posterior spinal access under surgeon control for focal shrinking of the annulus fibrosus membrane.

Where an intervertebral disc cannot be repaired and must be removed as part of a discectomy, device 10 may be particularly useful to seal and arrest bleeding from the cancellous bone of opposing upper and lower vertebra surfaces (e.g. the cephalad surface of the vertebral body of a superior vertebra and the caudad surface of an inferior vertebra). Where the disc is removed from the front of the patient, for example, as part of an anterior, thoracic spine procedure, device 10 may also be particularly useful to seal and arrest bleeding from segmental vessels over the vertebral body.

Device 10 may be utilized to seal and arrest bleeding of epidural veins which bleed as a result of the removal of tissue around the dural membrane during, for example a laminectomy or other neurosurgical surgery. The epidural veins may start bleeding when the dura is retracted off of them as part of a decompression. Also during a laminectomy, device 10 may be used to seal and arrest bleeding from the vertebral arch and, in particular the lamina of the vertebral arch.

As established above, device 10 of the present invention may inhibit such undesirable effects of tissue desiccation, electrode sticking, char formation and smoke generation. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

Although the present disclosure has been described with reference to preferred embodiments, workers skilled in the art will recognize that changes can be made in form and detail without departing from the spirit and scope of the present disclosure.

What is claimed is:

1. A tissue treatment assembly configured to engage and disengage with an electrosurgical unit having a source of radio-frequency energy, the tissue treatment assembly, comprising:
   a shaft including an elongated conductor having a proximal end portion and a distal end portion, the distal end portion including an electrode, wherein at least a section of the elongated conductor is a hollow shaft;
   a handle operably coupled to the shaft to enable a user of the tissue treatment assembly to hold and manipulate the tissue treatment assembly by hand;
   a cartridge member formed from an electrically insulating material and associated with the proximal end portion of the shaft and the handle, the cartridge member including:
      an identifier circuit including a printed circuit board having a circuit element configured to afford communication of a signal from the tissue treatment assembly to the electrosurgical unit, wherein the signal is configured to identify a parameter of the tissue treatment assembly, an identifier number of the tissue treatment assembly, and an operating relationship between fluid flow settings and power delivery settings over a range of power delivery settings as tissue treatment information, the tissue treatment information stored on the identifier circuit, the signal may be received by the electrosurgical unit as a stream of data to the electrosurgical unit, wherein the tissue treatment information in the signal automatically configures the electrosurgical unit in a default power delivery and default fluid flow setting provided to the tissue treatment assembly; and
      a portion of a control circuit couplable to the elongated conductive portion, the control circuit having an electrical input configured to receive radio-frequency energy based on the parameter from the source of radio-frequency energy and configured to provide the radio-frequency energy to the elongated conductive portion; and
a switch disposed between the electrical input and the electrode, the switch transitionable between an open position and a closed position, wherein the closed position enables radiofrequency energy to reach the electrode, and wherein the open position prevents radio-frequency energy from reaching the electrode.

2. The tissue treatment assembly of claim 1 wherein the portion of the control circuit is disposed on the printed circuit board.

3. The tissue treatment assembly of claim 2 wherein the printed circuit board includes electrical contacts in electrical communication with the elongated conductor.

4. The tissue treatment assembly of claim 1 wherein the identifier circuit includes a tangible storage medium configured to store the parameter.

5. The tissue treatment assembly of claim 4 wherein the tangible storage medium includes an electronic memory device on the printed circuit board.

6. The tissue treatment assembly of claim 5 wherein the electronic memory device includes an electrically erasable programmable read only memory device storing operating parameters of the tissue treatment assembly.

7. The tissue treatment assembly of claim 3 wherein the identifier circuit is configured to provide the signal to identify the parameter in response to a signal from the electrosurgical unit.

8. The tissue treatment assembly of claim 1 wherein the assembly includes a second electrode and the control circuit is configured to provide radio-frequency energy in a bipolar mode in response to the parameter.

9. The tissue treatment assembly of claim 1 wherein the cartridge member and the hollow shaft are in fluid communication with a source of fluid.

10. The tissue treatment assembly of claim 1 wherein the tissue treatment assembly is in fluid communication with a source of suction.

11. The tissue treatment assembly of claim 1, wherein the cartridge member includes an elongated single piece cartridge body.

12. A tissue treatment device configured to selectively engage and disengage with an electrosurgical unit having a source of radio-frequency energy, the tissue treatment device comprising:
a shaft including an elongated conductive portion having a proximal end portion and a distal end portion, the distal end portion including an electrode, wherein at least a portion of the elongated conductive portion is a hollow shaft;
a handle operably coupled to the shaft to enable a user of the tissue treatment assembly to hold and manipulate the tissue treatment assembly by hand;
a cartridge member associated with the proximal end of the shaft and the handle, the cartridge member including,
an identifier circuit having a circuit element configured to afford communication of a parameter of the tissue treatment device, an identifier number of the tissue treatment device, and an operating relationship between fluid flow settings and power delivery settings over a range of power delivery settings as tissue treatment information stored on the identifier circuit the tissue treatment information that may be received by the electrosurgical unit from the tissue treatment assembly as a stream of data to the electrosurgical unit, wherein the tissue treatment information automatically configures the electrosurgical unit in a default power delivery and default fluid flow setting provided to the tissue treatment device; and
a portion of a control circuit coupled to the elongated conductor, the control circuit having an electrical input configured to receive radio-frequency energy from the source of radio-frequency energy based on the parameter and configured to selectively provide the radio-frequency energy to the elongated conductor.

13. The tissue treatment device of claim 12 wherein the identifier circuit is disposed on a printed circuit board.

14. The tissue treatment device of claim 13 wherein the identifier circuit includes an integrated circuit element having a tangible storage medium storing the parameter.

15. The tissue treatment device of claim 12 comprising a switch disposed between the electrical input and the electrode, the switch transitionable between an open position and a closed position, wherein the closed position enables radio-frequency energy to reach the electrode, and wherein the open position prevents radio-frequency energy from reaching the electrode.

16. The tissue treatment device of claim 12 comprising a second electrode.

17. The tissue treatment device of claim 16 wherein the parameter includes a power delivery setting for a bipolar mode.

18. The tissue treatment device of claim 12 wherein the cartridge member and the hollow shaft are in fluid communication with a source of fluid, and wherein the fluid flow settings include a rate of fluid flow to be provided to the assembly from the electrosurgical unit.

19. A bipolar tissue treatment assembly configured to engage an electrosurgical unit having a source of radio-frequency energy, the bipolar tissue treatment assembly comprising: a shaft including a plurality of elongated conductive portions each having a proximal end portion and a distal end portion, wherein each of the distal end portions includes an electrode; and a handle operably coupled to the shaft to enable a user of the tissue treatment assembly to hold and manipulate the tissue treatment assembly by hand:
a cartridge member associated with the proximal end portions of the elongated conductive portions and the handle, the cartridge member including,
an identifier circuit having a circuit element configured to afford communication of a signal from the bipolar tissue treatment assembly to the electrosurgical unit, wherein the signal is configured to identify a parameter including a bipolar configuration stored in the identifier circuit within the cartridge member, the bipolar configuration including an identifier number of the tissue treatment assembly and an operating relationship between fluid flow settings and power delivery settings over a range of power delivery settings as tissue treatment information that may be received by the electrosurgical unit as a stream of data to the electrosurgical unit, wherein the bipolar configuration automatically configures the electrosurgical unit in a default power delivery and default fluid flow setting provided to the bipolar tissue treatment assembly; and
a portion of a control circuit coupled to the elongated conductive portions, the control circuit having an electrical input configured to receive radio-frequency energy from the source of radio-frequency energy based on the parameter and configured to selectively provide the radio-frequency energy to the elongated conductive portions.

20. The bipolar tissue treatment assembly of claim 19 wherein each of the elongated electrical conductive portions includes electrically conductive hollow shafts.

21. The bipolar tissue treatment assembly of claim 20 wherein each of the electrically conductive hollow shafts includes stainless steel.

22. The bipolar tissue treatment assembly of claim 20 wherein the electrically conductive hollow shafts are electrically insulated from each other.

23. The bipolar tissue treatment assembly of claim 19 wherein the cartridge member and a hollow shaft of the hollow shafts is in fluid communication with a source of fluid, and wherein the parameter includes a fluid flow setting indicating a rate of fluid flow to be provided to the assembly from the electrosurgical unit.

24. The bipolar treatment assembly of claim 23 wherein each of the hollow shafts are in fluid communication with the source of fluid.

25. The bipolar tissue treatment assembly of claim 23 wherein the fluid flow settings include a rate of fluid flow to be provided to the assembly from the electrosurgical unit.

26. A tissue treatment assembly configured to selectively engage and disengage with a source of fluid and an electrosurgical unit having a source of radio-frequency energy, the tissue treatment assembly comprising:
   a shaft including an elongated conductor having a proximal end and a distal end, the distal end having an electrode, wherein at least a portion of the elongated conductor is a hollow shaft configured to be in communication with the source of fluid;
   a handle operably coupled to the shaft to enable a user of the tissue treatment assembly to hold and manipulate the tissue treatment assembly by hand:
   a cartridge member coupled to the proximal end of the shaft and the handle, the cartridge member in fluid communication with the shaft and configured to be in fluid communication with the source of fluid, the cartridge member including,
      an identifier circuit including a printed circuit board having a circuit element configured to afford communication of a signal from the tissue treatment assembly to the electrosurgical unit, wherein the signal is configured to identify parameters stored in the identifier circuit within the cartridge member, the parameters including an identifier number of the tissue treatment assembly and an operating relationship between fluid flow settings and power delivery settings over a range of power delivery settings as tissue treatment information that may be received by the electrosurgical unit, wherein the parameters automatically configure the electrosurgical unit in a default power delivery and default fluid flow setting provided to the tissue treatment assembly;
      a fluid input configured to receive a fluid from the source of fluid at a rate of fluid determined by the parameters and to provide the fluid to the hollow shaft; and
      a portion of a control circuit coupled to the elongated conductor, the control circuit configured to receive a radio-frequency energy based on the parameters from the source of radio-frequency energy and configured provide the radio-frequency energy to the elongated conductor; and
      a switch disposed between the electrical input and the electrode, the switch transitionable between an open position and a closed position, wherein the closed position enables radiofrequency energy to reach the electrode.

27. The tissue treatment assembly of claim 26 comprising a second electrode.

28. The tissue treatment assembly of claim 27 wherein the second electrode includes a hollow shaft.

29. The tissue treatment assembly of claim 28 where in the hollow shaft of the second electrode is in fluid communication with the fluid input.

30. The tissue treatment assembly of claim 26, wherein the cartridge member includes an elongated single piece cartridge body.

31. A bipolar tissue treatment assembly configured to engage and disengage with a source of fluid and an electrosurgical unit having a source of radio-frequency energy, the bipolar tissue treatment assembly comprising:
   a shaft assembly including,
      a first elongated conductor having a first proximal end portion and a first distal end portion, the first distal end portion including a first electrode, wherein at least a section of the first elongated conductor is a first hollow shaft;
      a second elongated conductor having a second proximal end portion and a second distal end portion, the second distal end portion including a second electrode, wherein at least a section of the second elongated conductor is a second hollow shaft;
   a handle operably coupled to the shaft assembly to enable a user of the bipolar tissue treatment assembly to hold and manipulate the bipolar tissue treatment assembly by hand:
   a cartridge member formed from an electrically insulating material and associated with the first and second proximal end portions of the first and second shafts and handle, the cartridge member including:
      an identifier circuit including a printed circuit board having a circuit element configured to afford communication of a signal from the bipolar tissue treatment assembly to the electrosurgical unit, wherein the signal is configured to identify parameters of the bipolar tissue treatment assembly to the electrosurgical unit and wherein the parameters are stored in the identifier circuit within the cartridge member wherein the parameters include an identifier number of the bipolar tissue treatment assembly and an operating relationship between power delivery settings and rate of fluid flow settings over a range of power delivery settings as tissue treatment information that may be received by the electrosurgical unit as a stream of data to the electrosurgical unit, wherein the parameters automatically configure the electrosurgical unit at a range of power levels and fluid flow levels in a default power delivery and default fluid flow setting provided to the bipolar tissue treatment assembly;
      a fluid input configured to receive a fluid from the source of fluid based on the rate of fluid flow settings and to provide the fluid to the first and second hollow shafts; and
      a portion of a control circuit couplable to the first and second elongated conductive portion, the control circuit having an electrical input configured to receive radio-frequency energy based on the power delivery setting from the source of radio frequency energy and configured to provide the radio-frequency energy to one of the first and second elongated conductors; and a switch disposed between the electrical input and one of the first and second electrodes, the switch transitionable between an open position and a closed position, wherein the closed position enables radio-frequency energy to reach the one of the first and second electrodes, and wherein the open position prevents radio-frequency energy from reaching the one of the first and second electrodes.

32. The bipolar tissue treatment assembly of claim 31 wherein the first and second electrodes are electrically insulated from each other.

33. The bipolar tissue treatment assembly of claim 32 wherein the first and second electrodes are spaced apart from each other.

34. The bipolar tissue treatment assembly of claim 31 wherein the bipolar tissue treatment assembly is in fluid communication with a source of suction.

35. A tissue treatment assembly configured to engage and disengage with an electrosurgical unit having a source of radio-frequency energy, the tissue treatment assembly comprising:
  a shaft including at least one elongated conductor portion, wherein the at least one elongated conductor portion comprises a proximal end portion and a distal end portion, the distal end portion, the distal end portion including an electrode, wherein at least a section of the elongated conductor portion is a hollow shaft; and
  a handle operably coupled to the shaft to enable a user of the tissue treatment assembly to hold and manipulate the tissue treatment assembly by hand;
  a cartridge member formed from an electrically insulating material and associated with the proximal end portion of the shaft and the handle, the cartridge member including:
    an identifier circuit including a circuit element configured to provide an identification signal from the tissue treatment assembly to the electrosurgical unit in response to an access signal from the electrosurgical unit, wherein the identification signal is configured to identify a parameter of the tissue treatment assembly stored in the identifier circuit within the cartridge member the parameter including an identifier number of the tissue treatment assembly and an operating relationship between fluid flow settings and power delivery settings over a range of power delivery settings as tissue treatment information that may be received by the electrosurgical unit as a stream of data to the electrosurgical unit, wherein the parameter automatically configures the electrosurgical unit in a default power delivery and default fluid flow setting provided to the tissue treatment assembly; and
    a portion of a control circuit couplable to the elongated conductive portion, the control circuit having an electrical input configured to receive radio-frequency energy from the source of radio-frequency energy based on the parameter and configured to provide the radio-frequency energy to the elongated conductive portion.

36. The tissue treatment assembly of claim 35 wherein the identification signal is provided to the electrosurgical unit upon engagement with the electrosurgical unit.

37. The tissue treatment assembly of claim 36 wherein the circuit element is a memory device and the electrosurgical unit is configured to access the memory device.

38. The tissue treatment assembly of claim 37 wherein the identification signal is a stream of serial data.

39. The tissue treatment assembly of claim 35 wherein the electrosurgical unit is configured to read a maximum power level for the tissue treatment assembly from the identification signal.

40. The tissue treatment assembly of claim 39 wherein the electrosurgical unit is programmed to provide a power level having an upper limit in accord with the maximum power level from the identification signal.

41. The tissue treatment assembly of claim 39 wherein the electrosurgical unit is configured to read a fluid throughput for the treatment assembly from the identification signal.

42. The tissue treatment assembly of claim 35 wherein the at least one elongated conductor portion comprises a plurality of elongated conductive portions each having a proximal end portion and a distal end portion, wherein each of the distal end portions includes an electrode,
  wherein the portion of a control circuit is coupled to the elongated conductive portions and configured to selectively provide the radio-frequency energy to the elongated conductive portions.

43. The tissue treatment assembly of claim 35 wherein the cartridge member includes a cartridge configured to selectively engage with the electrosurgical unit.

44. The tissue treatment assembly of claim 35 wherein the control circuit includes a switch disposed between the electrical input and the electrode, the switch transitionable to a closed position, wherein the closed position enables radio-frequency energy to reach the electrode.

* * * * *